(12) United States Patent
Badylak et al.

(10) Patent No.: US 10,286,119 B2
(45) Date of Patent: May 14, 2019

(54) EXTRACELLULAR MATRIX MESH COATING

(71) Applicant: University of Pittsburgh—Of the Commonwealth System of Higher Education, Pittsburgh, PA (US)

(72) Inventors: Stephen F. Badylak, Pittsburgh, PA (US); Matthew T. Wolf, Baltimore, MD (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 711 days.

(21) Appl. No.: 14/603,687

(22) Filed: Jan. 23, 2015

(65) Prior Publication Data

US 2015/0297798 A1 Oct. 22, 2015

Related U.S. Application Data

(60) Provisional application No. 61/931,056, filed on Jan. 24, 2014.

(51) Int. Cl.
| | |
|---|---|
| *A61L 27/36* | (2006.01) |
| *A61L 31/06* | (2006.01) |
| *A61L 31/14* | (2006.01) |
| *A61L 31/04* | (2006.01) |
| *A61L 31/10* | (2006.01) |
| *A61F 2/00* | (2006.01) |

(52) U.S. Cl.
CPC .............. *A61L 31/06* (2013.01); *A61L 31/048* (2013.01); *A61L 31/10* (2013.01); *A61L 31/145* (2013.01); *A61F 2/0063* (2013.01); *A61F 2/0077* (2013.01)

(58) Field of Classification Search
CPC .................................................... A61L 31/06
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,711,969 A | 1/1998 | Patel et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 6,099,567 A | 8/2000 | Badylak et al. |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 8,361,503 B2 | 1/2013 | Badylak et al. |
| 9,421,307 B2 | 8/2016 | Amoroso et al. |

OTHER PUBLICATIONS

Wolf et al. Society for Biomaterials, abstract #393, 2013, 1 page.*
Hong et al. Biomaterials, 2011, 32:3387-3394.*
Abed et al. Tissue Engineering, 2008, 14(4):519-527.*
Billiar et al., "Biaxial mechanical properties of the natural and glutaraldehyde treated aortic valve cusp—Part I: Experimental results", J Biomech Eng, Feb. 2000, p. 23-30, 122.
Faulk et al., "ECM hydrogel coating mitigates the chronic inflammatory response to polypropylene mesh", Biomaterials, (2014), p. 8585-8595, 35.
Keane et al., "Consequences of Ineffective Decellularization of Biologic Scaffolds on the Host Response," Biomaterials, (2012), p. 1771-81, 33.
Nadkarni et al., "Measurement of collagen and smooth muscle cell content in atherosclerotic plaques using polarization-sensitive optical coherence tomography", J Am. Coll. Cardiol, Apr. 3, 2007, p. 1474-1481, 49(13).
Reing et al., "The effects of processing methods upon mechanical and biologic properties of porcine dermal extracellular matrix scaffolds", Biomaterials, Nov. 2010, p. 8626-8633, 31(33).
Rich et al., "Collagen and picrosirius red staining: a polarized light assessment of fibrillar hue and spatial distribution", Braz J Morphol Sci, 2005, p. 97-104, 22(2).
Wolf et al., "A hydrogel derived from decellularized dermal extracellular matrix", Biomaterials, Oct. 2012, p. 7028-7038, 33.
Wolf et al., "Polypropylene surgical mesh coated with extracellular matrix mitigates the host foreign body response", J Biomed Mater Res A, Jan. 19, 2015, p. 1-22.
Wolf et al., "Macrophage polarization in response to ECM coated polypropylene mesh", Biomaterials, (2014), p. 6838-6849, 35.

* cited by examiner

*Primary Examiner* — Bin Shen
(74) *Attorney, Agent, or Firm* — The Webb Law Firm

(57) ABSTRACT

Provided are surgical meshes embedded in a gelled, solubilized extracellular matrix (ECM) composition, methods of making the same, and methods of using the same to repair defects in a body. The surgical mesh may be a synthetic polymer such as polypropylene, and the ECM coating reduces the foreign body response and scarring at the site of implantation. The device is useful for repairing hernias, pelvic floor disorders, and in breast reconstructions.

16 Claims, 37 Drawing Sheets

Day 3

BARD™ Mesh

ECM coated BARD™ Mesh

EXTRACELLULAR MATRIX MESH COATING

CROSS-REFERENCE TO RELATED APPLICATIONS

This application claims the benefit of U.S. Provisional Patent Application No. 61/931,056, filed Jan. 24, 2014, which is incorporated herein by reference in its entirety.

BACKGROUND

Meshes coated with extracellular matrix (ECM)-derived hydrogels, cell-growth scaffolds and related methods are described herein.

The host response to surgically implanted biomaterials is a complex, temporally regulated process that is a critical determinant of functional outcome. Biomaterial devices may be relatively simple, such as knitted mesh constructs used for hernia repair, pelvic floor repair, and/or breast reconstruction, or highly complex, such as pacemaker electrodes. The host tissue response to any implanted device occurs through a host-material surface interaction and resultant downstream tissue remodeling within and around the device. Non-degradable synthetic polymers used for long term implantation, such as polytetrafluoroethylene (PTFE), polyethylene terephthalate, and polypropylene, elicit a classic foreign body response following implantation.

The foreign body reaction has been well-characterized from a histopathologic perspective, and components of the innate immune response play a critical role. Innate immune cell involvement begins with an acute inflammatory phase dominated by polymorphonuclear cells, followed by peripheral blood monocyte recruitment, and monocyte differentiation to macrophages that accumulate at the biomaterial surface. Inability to eliminate the foreign material with resultant persistent exposure to a non-degradable or slowly degradable material results in chronic inflammation and a mature foreign body reaction. Macrophage fusion into multinucleated foreign body giant cells and eventual fibrotic scar tissue deposition are hallmarks of this response.

Alternatively, surgical mesh materials composed of naturally occurring extracellular matrix (ECM) typically result in a non-fibrotic response following implantation. ECM scaffolds are prepared via decellularization of various warm-blooded mammalian tissues including, but not limited to, dermis, small intestinal submucosa, pericardium, and urinary bladder. The decellularization process disrupts and removes the cellular components of the tissue, which would otherwise initiate a robust pro-inflammatory response, and ideally leaves the remaining ECM intact. The ECM is a highly-conserved and complex assembly of structural and biochemically functional molecules that represent a cell-friendly micro-environmental niche. The innate immune response to an implanted ECM scaffold is histologically similar to the response to synthetic materials and is characterized by an accumulation of macrophages within and around the implanted ECM. However, non-crosslinked ECM scaffolds that are sufficiently decellularized are rapidly degraded and replaced with site-appropriate host tissue rather than fibrotic scar (see, e.g., Keane et al., "Consequences of Ineffective Decellularization of Biologic Scaffolds on the Host Response," *Biomaterials* 33:1771-81 (2012)). The mechanisms of ECM scaffold remodeling are only partially understood, but studies have shown that immune activation processes are critical determinants of the downstream remodeling outcome. Despite the benefits of ECM-based products, a shortcoming to those products is their lack of mechanical strength. Thus, ECM-only products are not suitable solutions to the problem of the inflammatory response seen with synthetic meshes.

A robust and persistent macrophage infiltrate is found after implantation of both non-degradable synthetic polymers and degradable ECM, however, the remodeling outcome diverges considerably. A potential cause of the disparate host response is the effect of the biomaterial upon differential macrophage activation pathways. Macrophages may be polarized along a spectrum of two contrasting functional phenotypes: the classically activated pro-inflammatory M1 phenotype associated with host defense and the foreign body response, or the alternatively activated M2 phenotype associated with constructive tissue remodeling. Macrophage polarization has been studied in numerous biological contexts, including tumor growth, fetal development, and the host response to implanted biomaterials. Macrophages involved in constructive ECM remodeling present a greater proportion of the M2 phenotype compared to the phenotypic profile in the presence of non-degradable synthetic materials or chemically crosslinked, slowly degradable ECM, both of which show a dominant M1 response.

The gold standard for biomaterials used in ventral hernia repair are synthetic polymers, notably knitted polypropylene surgical mesh. Such synthetic materials have properties desirable for hernia repair such as high mechanical strength and efficient incorporation of the mesh into the surrounding host tissue. However, the inevitable foreign body reaction to polypropylene is associated with less desirable sequelae such as fibrosis, decreased tissue compliance, occasional fistula formation, and adhesions. Any of these events may result in patient discomfort and/or mesh explantation. Strategies to mitigate these events are of great interest. Accordingly, there is a need in the art for meshes suitable for implantation that have high mechanical strength and can be quickly incorporated into a site of injury, but that also have a lower propensity for chronic pain, contraction, restricted movement, and complications due to foreign body response and fibrosis.

SUMMARY

Provided herein are devices and methods utilizing a hydrogel form of ECM as a coating for a mesh to reduce the intensity of the foreign body reaction. The ECM coating markedly attenuates the short term foreign body responses after implantation of the mesh, including a reduction in both the number of foreign body giant cells and the density of host deposited collagen, while not negatively affecting the strength of the implanted mesh.

Provided herein is a surgical mesh including a synthetic polymer mesh embedded within a reverse-gelling hydrogel prepared from decellularized, intact ECM. In one embodiment, the synthetic polymer mesh is one or more of polytetrafluoroethylene, polyethylene terephthalate, and polypropylene. In a further embodiment, the synthetic polymer mesh is polypropylene. In an embodiment, the hydrogel forms a gel when the temperature of the gel is raised above 10° C.

In another embodiment, the ECM used in the hydrogel is derived from warm-blooded mammalian tissue. In further embodiments, the mammalian tissue is derived from a pig, cow, monkey, or human. In some embodiments, the mammalian tissue is derived from one or more of urinary bladder, spleen, liver, heart, pancreas, ovary, small intestine, or dermis. In a further embodiment, the ECM is derived from dermis.

In another embodiment, the ECM used in the hydrogel is not dialyzed. In other embodiments, the ECM contains less than 50 ng DNA/mg ECM. In still other embodiments, the ECM contains less than 750 nmol phospholipids/g ECM.

Also provided herein is a method of preparing a surgical mesh for implantation including the steps of (i) solubilizing decellularized, intact ECM by digestion with an acid protease in an acidic solution to produce a digest solution; (ii) raising the pH of the digest solution to a pH between 7.2 and 7.8 to produce a neutralized digest solution; (iii) immersing a synthetic polymer mesh in the neutralized digest solution; and (iv) gelling the solution at a temperature greater than 10° C., thereby producing a synthetic polymer mesh embedded in an ECM-derived hydrogel.

In certain embodiments, the ECM utilized in the method is not subjected to a cross-linking process prior to the solubilizing step. In some embodiments, the ECM is derived from mammalian tissue. In further embodiments, the mammalian tissue is derived from a pig, cow, monkey, or human. In some embodiments, the mammalian tissue is derived from one or more of urinary bladder, spleen, liver, heart, pancreas, ovary, small intestine, or dermis. In a further embodiment, the ECM is derived from dermis.

In some embodiments, the method further includes a step of freezing the embedded mesh. In some embodiments, the embedded mesh is snap frozen in liquid nitrogen. In other embodiments, the embedded mesh is frozen at −20° C. for at least eight hours. In additional embodiments, the method further includes a step of lyophilizing the frozen mesh.

In some embodiments of the method, the ECM utilized in the hydrogel is comminuted and/or lyophilized prior to solubilizing the ECM by digestion with the acid protease. In some embodiments, the ECM contains less than 50 ng DNA/mg ECM. In other embodiments, the ECM contains less than 750 nmol phospholipids/g ECM.

In some embodiments, the concentration of ECM in the hydrogel is at least 4 mg/ml. In further embodiments, the concentration of ECM in the hydrogel is at least 8 mg/ml. In some embodiments, the digest solution is poured into a mold holding the mesh and then gelled. In other embodiments, one or more of a cell, a drug, a cytokine and at least one growth factor are integrated into the gel.

In some embodiments of the method, the synthetic polymer mesh is one or more of polytetrafluoroethylene, polyethylene terephthalate, and polypropylene. In further embodiments, the synthetic polymer mesh is polypropylene. In other embodiments, the acid protease used is pepsin and/or trypsin.

Also provided herein is a method of repairing a defect in a body, including the step of integrating a surgical mesh as substantially described above at a site of a defect in a patient in need thereof. In some embodiments the defect is a hernia. In other embodiments the defect is a pelvic floor defect. In still other embodiments the defect is in breast tissue. In additional embodiments, the defect is a wound.

Figure 20A:
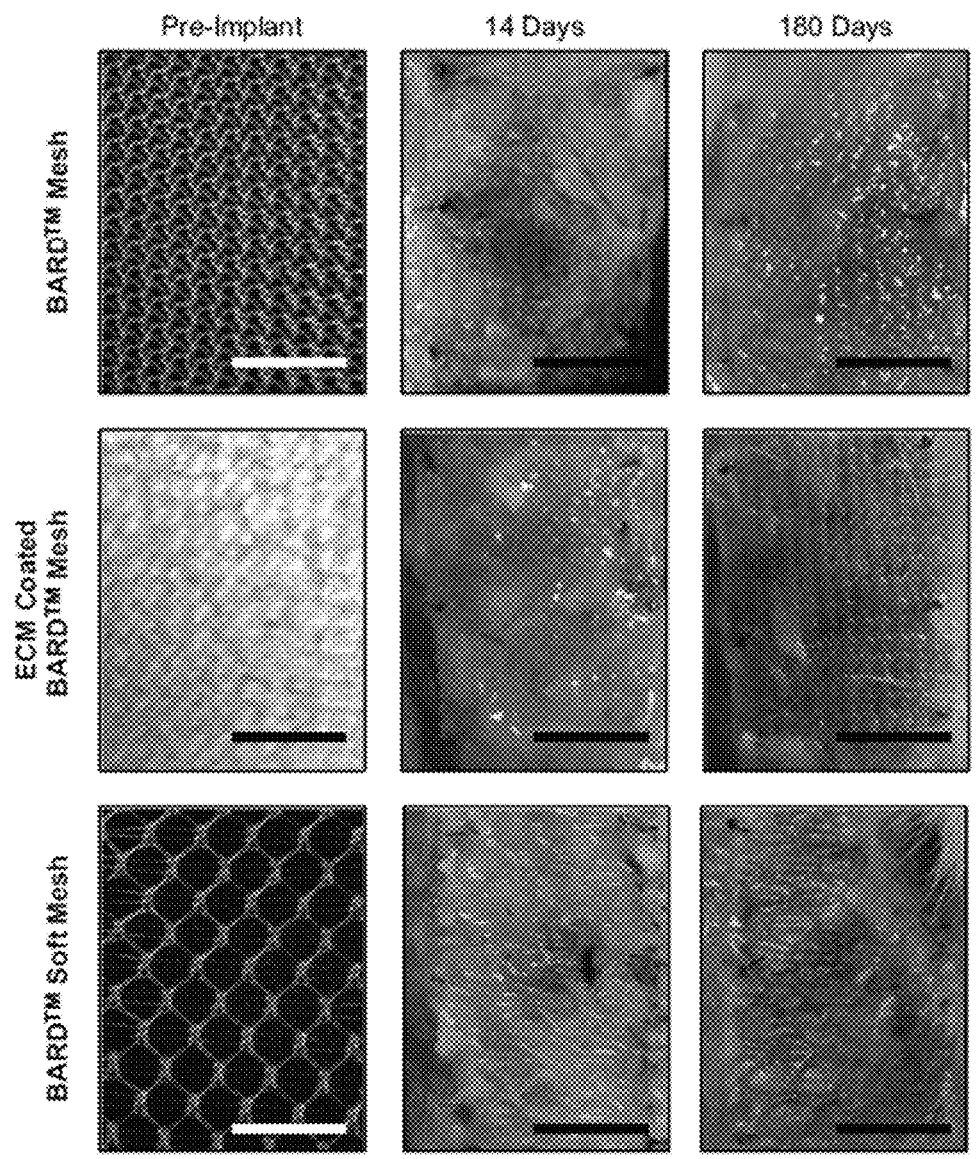
Figure 20B:
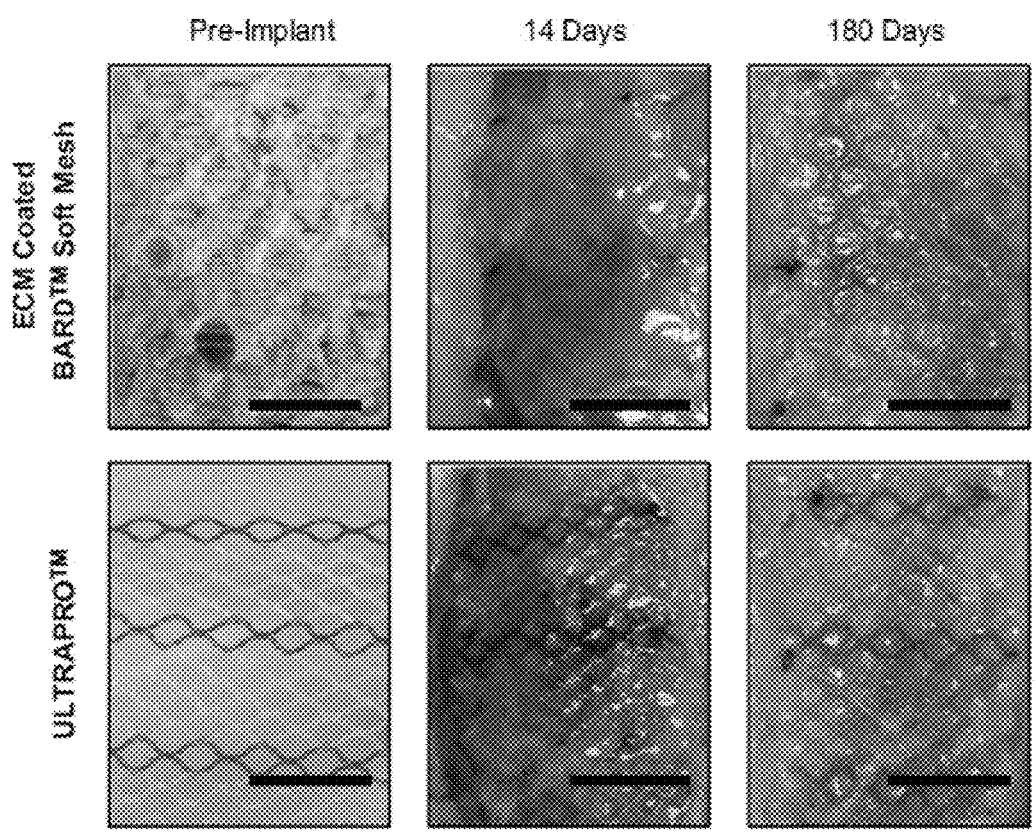

FIG. 20A-20B shows macroscopic images of each mesh device pre-implant (left column), 14 days post implantation (middle column), and 180 days post implantation (right column). Scale bar=1 cm.

Figure 21A:
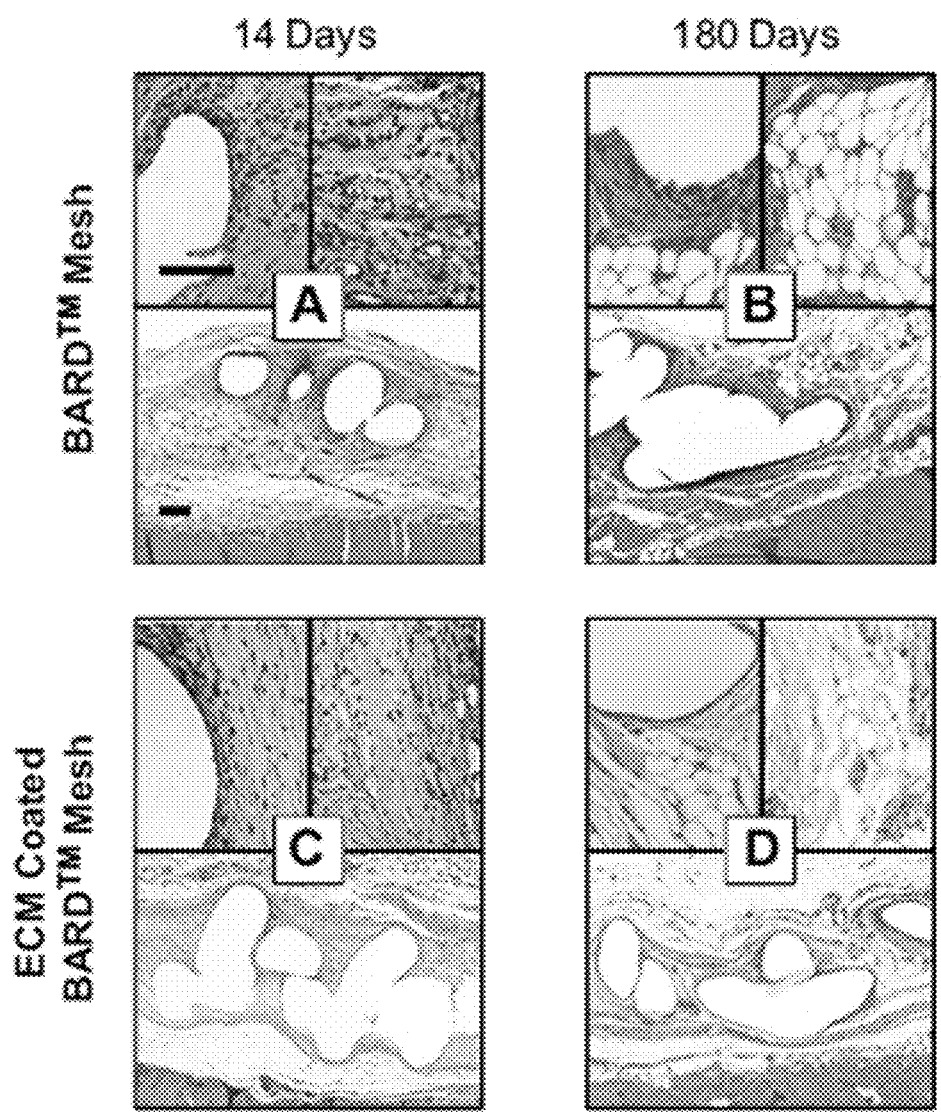
Figure 21B:
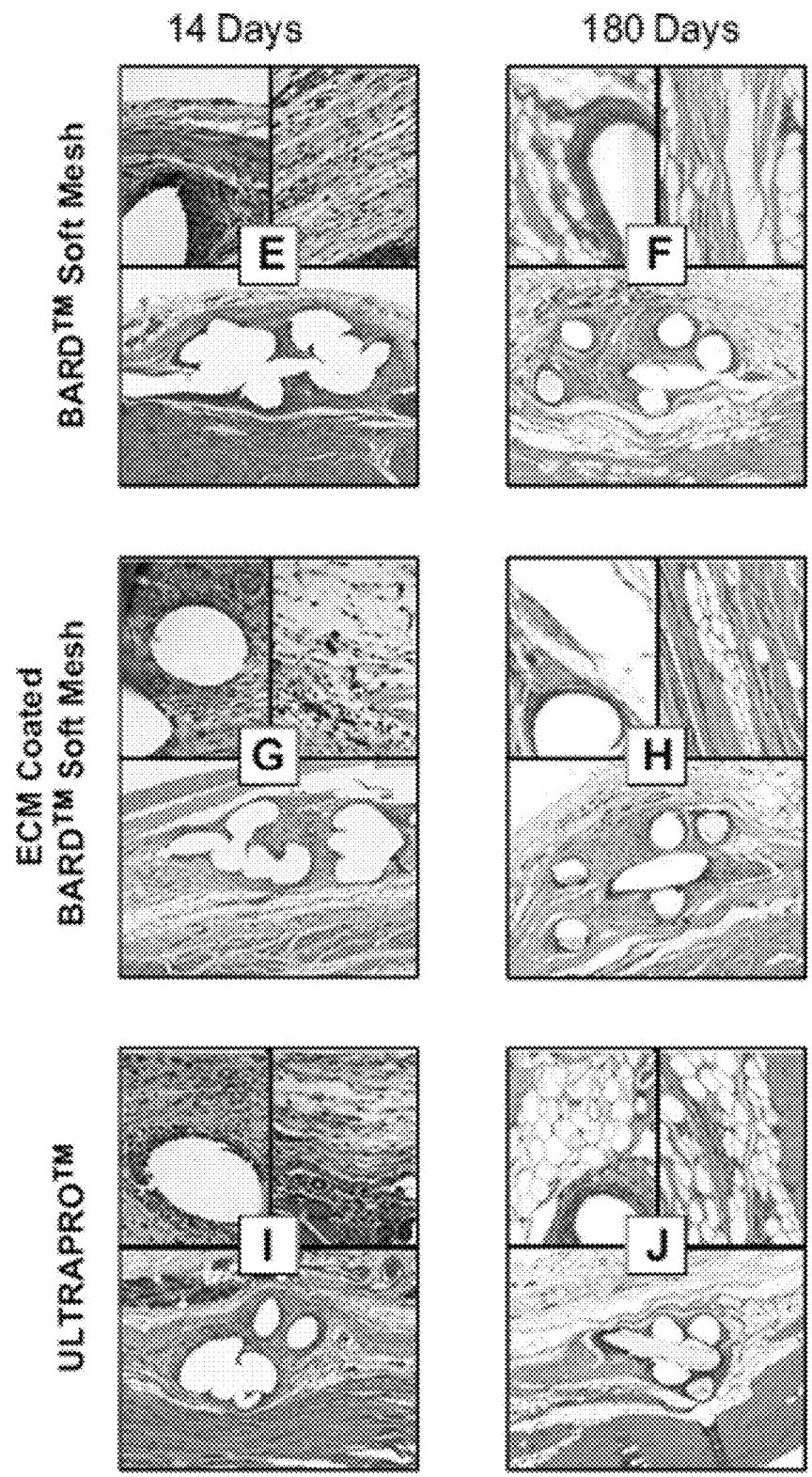

FIG. 21A-21B shows histologic appearance of mesh devices after 14 and 180 days of in vivo implantation. Representative H&E stained histologic cross sections of each mesh/time point were imaged at 100× magnification (bottom of each figure panel) and 400× magnification (top two images of each figure panel) Scale bars represent 100 mm.

Figure 22A:
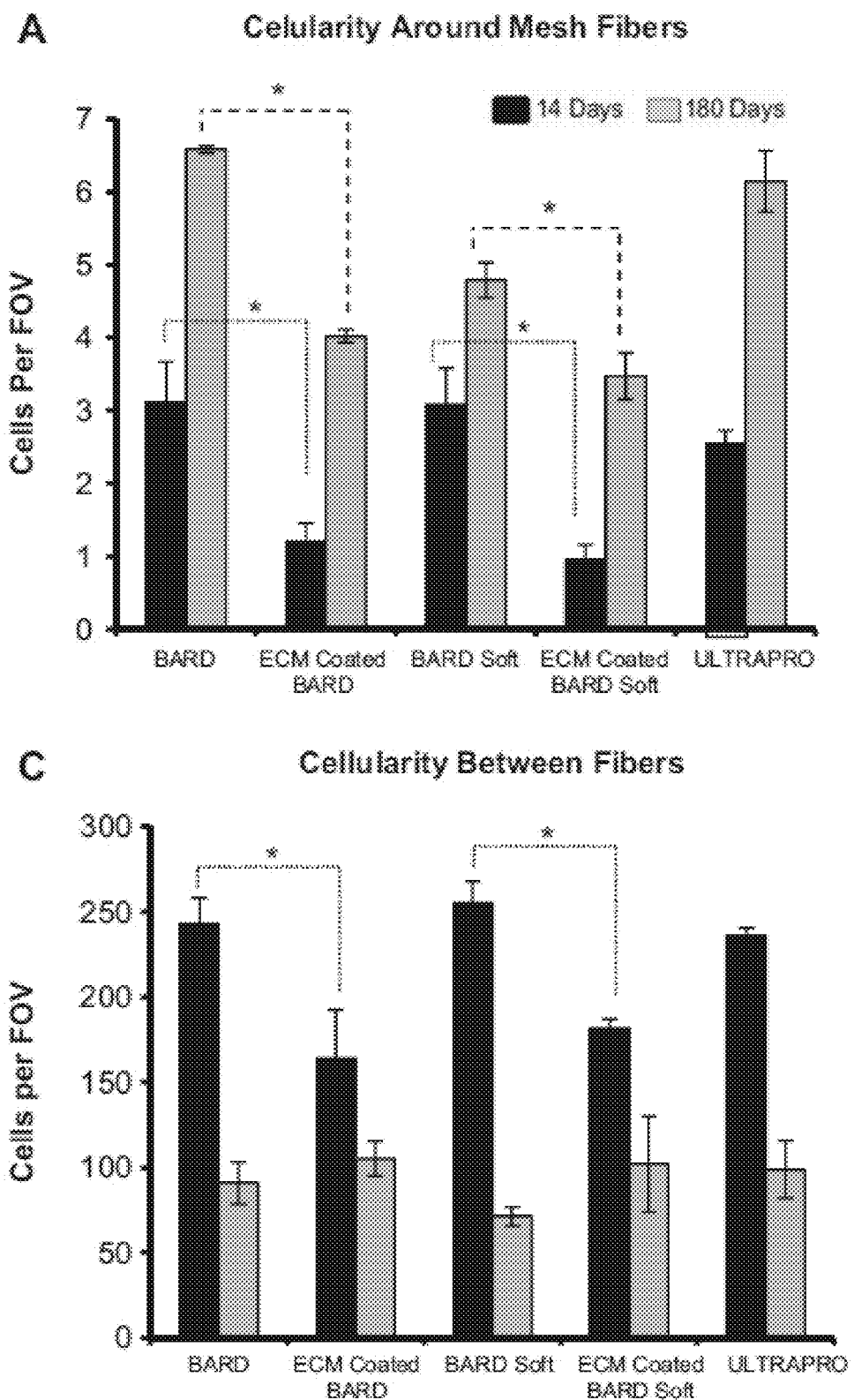
Figure 22B:
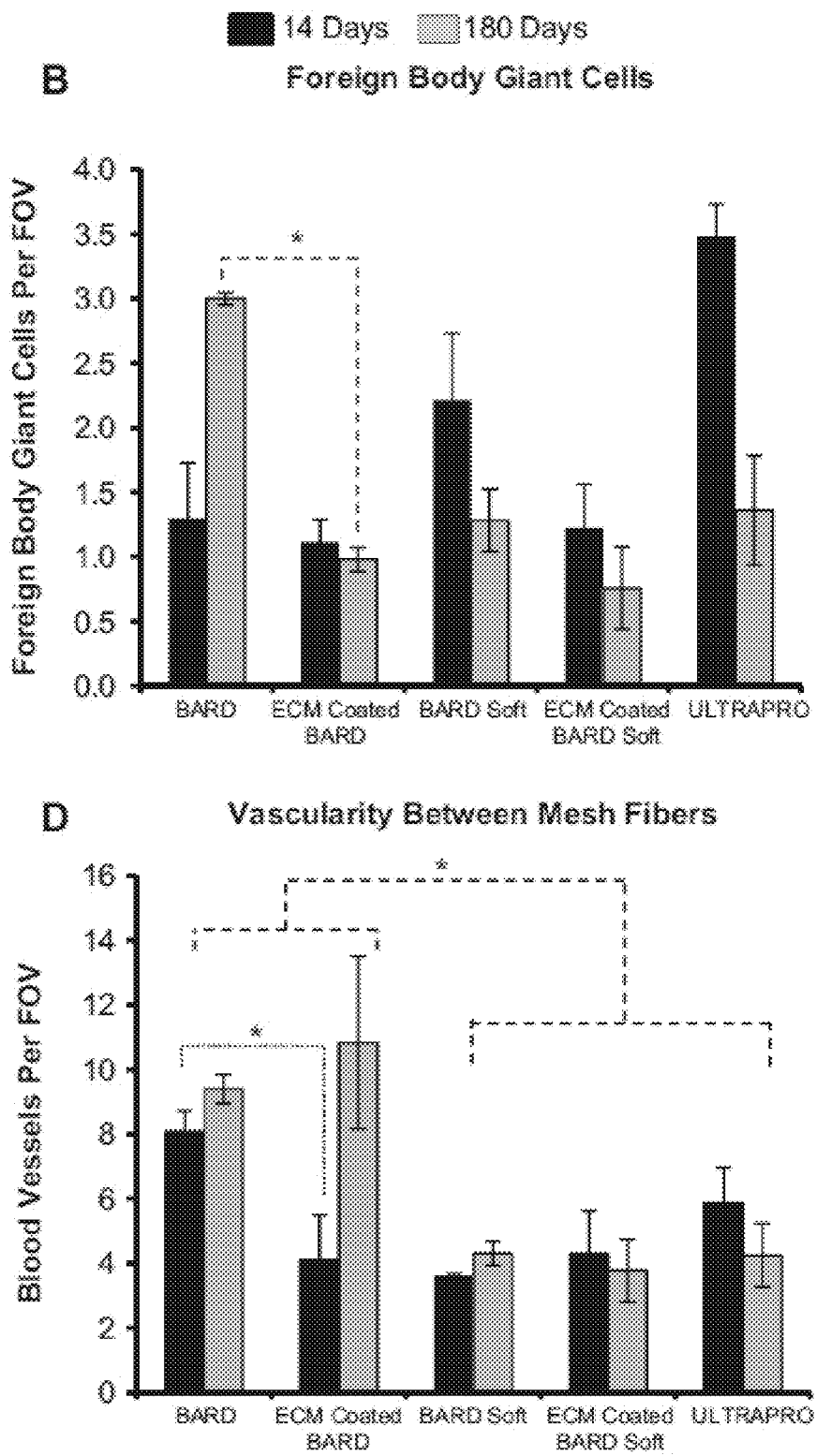

FIG. 22A-22B shows histomorphometric analysis of the histologic inflammatory response to mesh fibers and tissue remodeling in the area between mesh fibers from H&E stained histologic cross sections after 14 and 180 days post-implantation. (A) The mesh fiber cellularity and (B) number of foreign body giant cells for each device were counted to characterize the inflammatory response to mesh fibers. Tissue remodeling between mesh fibers was analyzed as the (C) number cells and (D) number of blood vessels. Significant differences (p<0.05) between devices within each time point are denoted as (*).

Figure 23A:
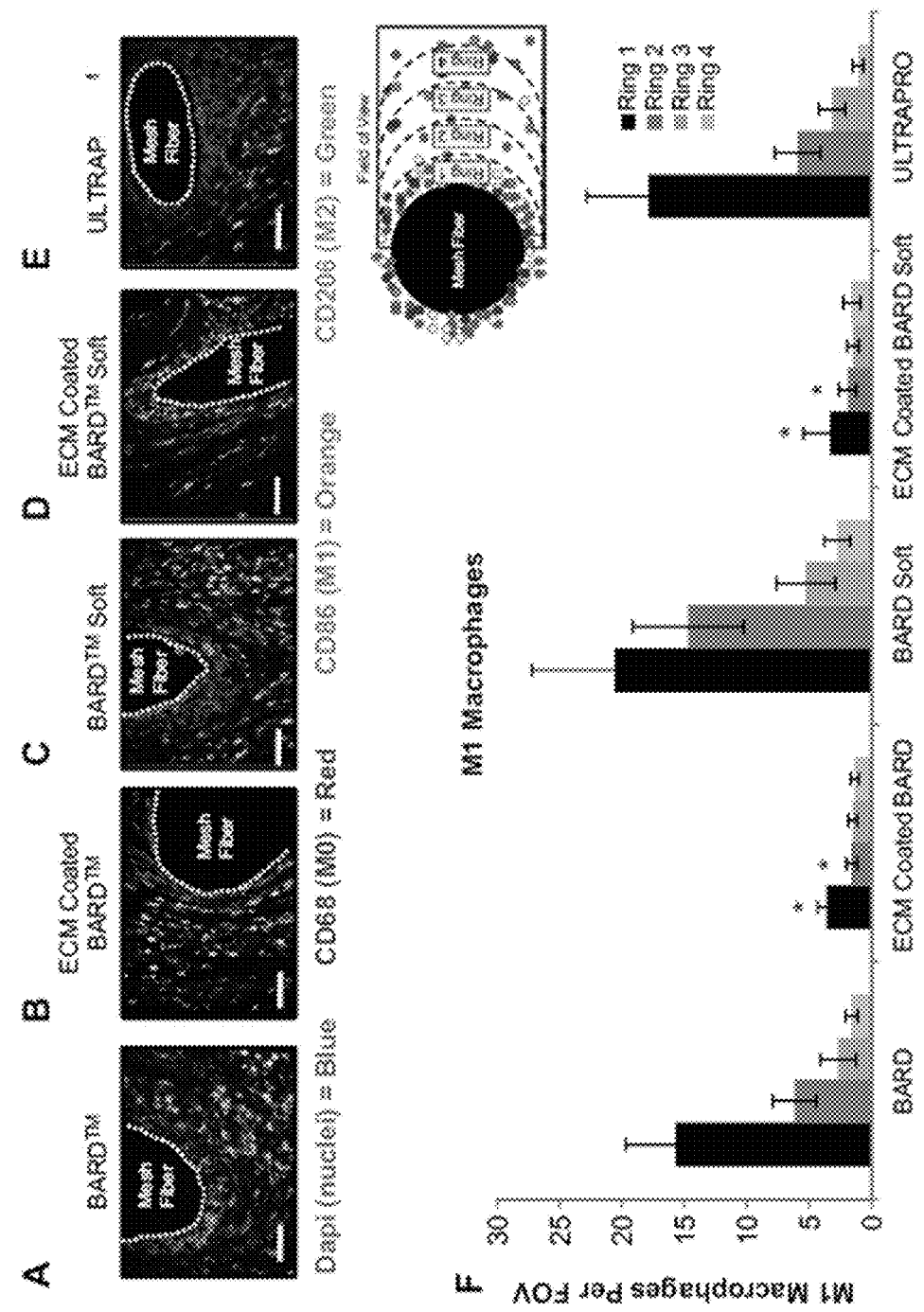
Figure 23B:
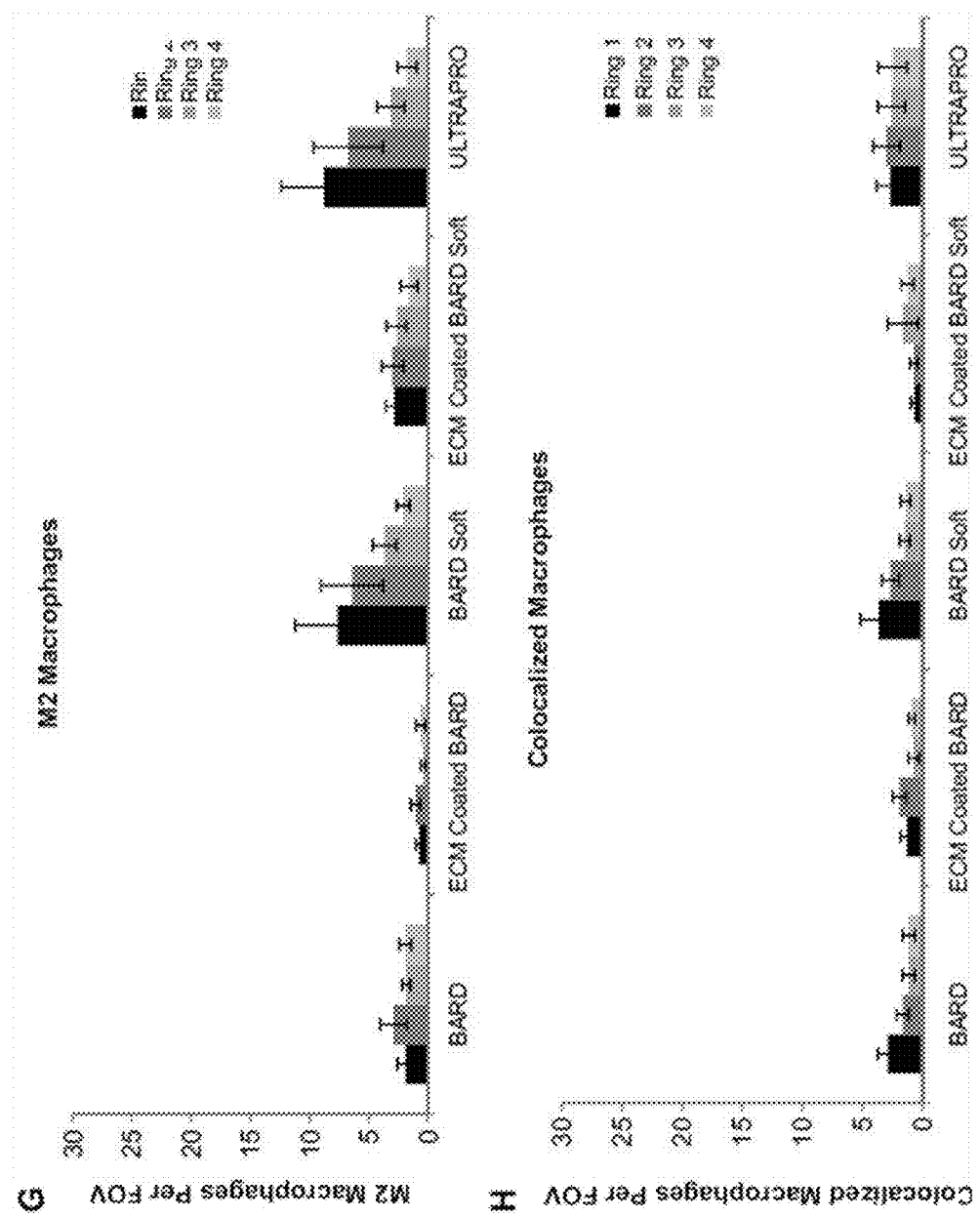

FIG. 23A-23B shows representative immunofluorescent images of the host macrophage response to mesh materials at 14 days post-implantation. Dapi (nuclei), CD68 (M0), CD86 (M1), CD206 (M2). Quantification of the (F) pro-inflammatory M1 (CD86+/CD68+) macrophages, (G) constructive remodeling M2 (CD206+/CD68+) macrophages, and (H) co-localized (CD86+/CD206+/CD68+) near mesh fibers. Each ring (1-4) represents increasing distance from the mesh fiber surface. Scale bar=50 mm.

Figure 24:
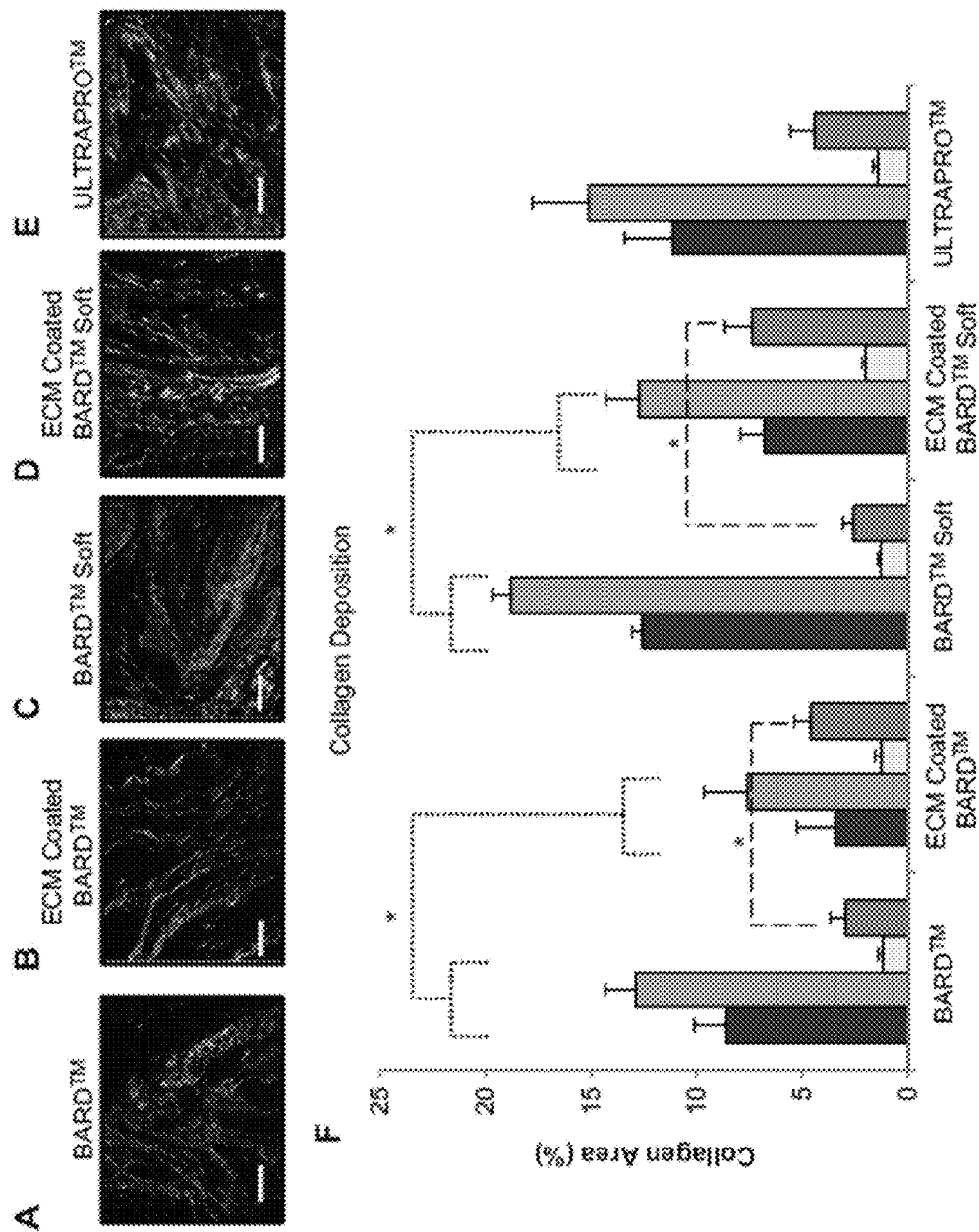

FIG. 24 shows Picrosirius red staining and quantification of collagen area between mesh fibers using polarized light microscopy. (A-E) Collagen fibers between the mesh fibers of each device after 180 days. The color hue of the fibers represents the relative collagen thicknesses (in order of thinnest to thickest). (F) Quantification of the total area and proportion of collagen (defined by color hue) in each mesh after 180 days. Significant differences (p<0.05) are denoted (*). Scale bar represents 50 mm.

Figure 25A:
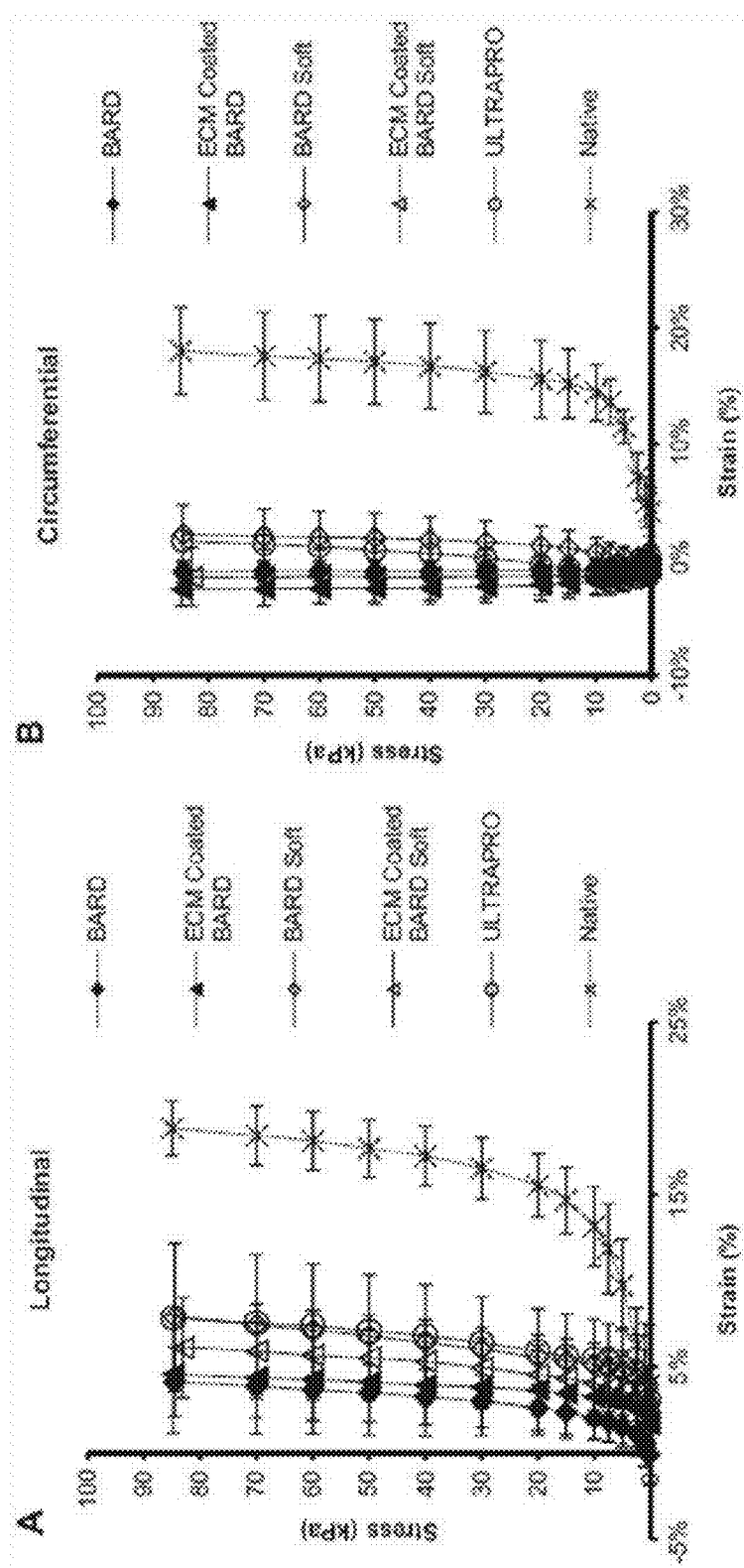
Figure 25B:
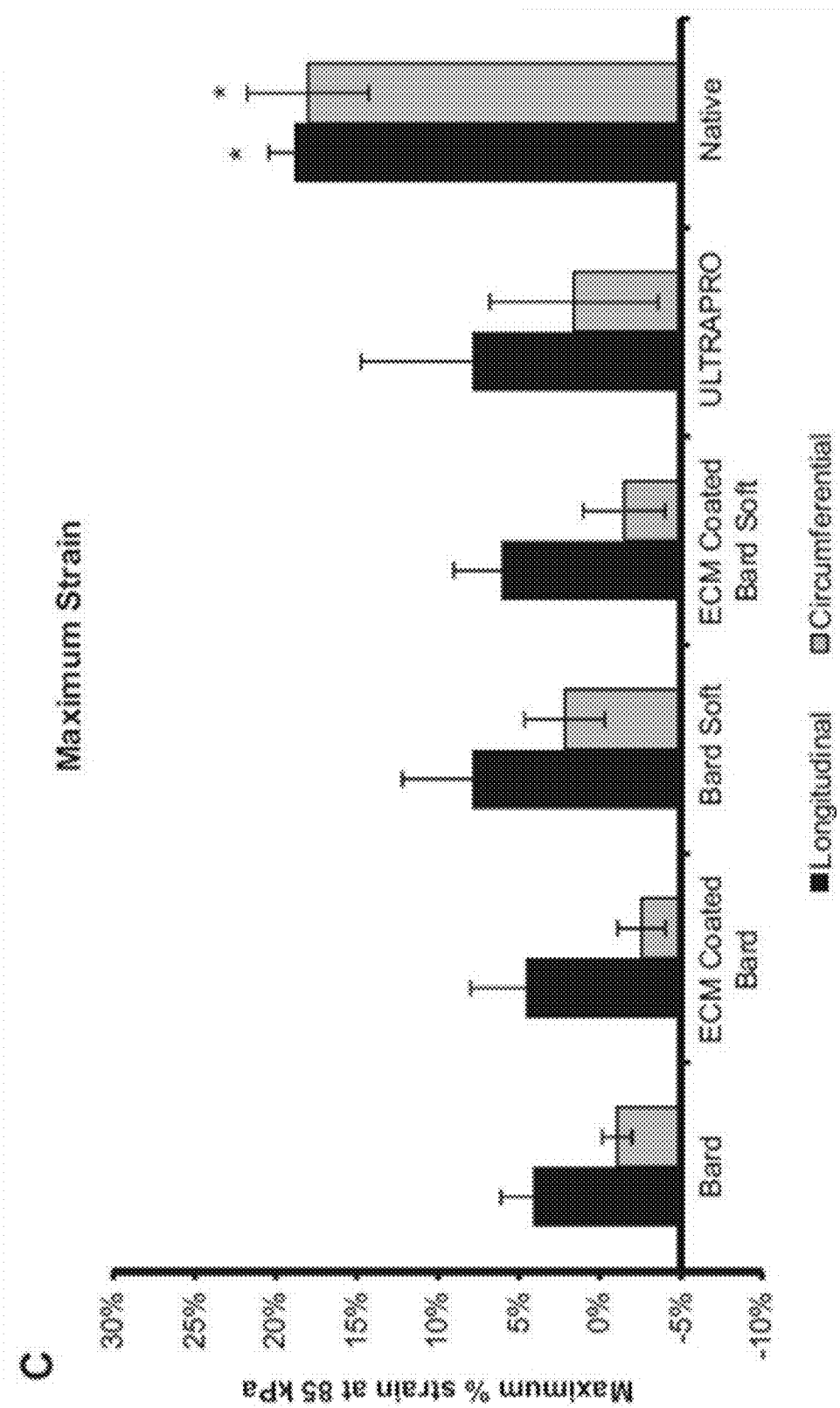

FIG. 25A-25B shows mesh explants equibiaxial mechanical characterization after 180 days. (A) The equibiaxial stress response of the explanted mesh devices were characterized along the circumferential and (B) longitudinal axes. (C) The maximum strain defined at a stress of 85 kPa for both circumferential and longitudinal axes. Significant differences (p<0.05) are denoted (*).

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

Provided herein are surgical meshes comprising a surgical mesh embedded within an extracellular matrix (ECM)-derived gel, methods of producing the same, and methods of repairing defects using the same. The ECM-derived gel is reverse gelling, or can be said to exhibit reverse thermal gelation, in that it forms a gel (sol to gel transition) upon an increase in temperature. The lower critical solution temperature (LCST) in a reverse gel is a temperature below which a reverse-gelling polymer is soluble in its solvent (e.g. water or an aqueous solvent). As the temperature rises above the LCST in a reverse gel, a hydrogel is formed. The general concept of reverse gelation of polymers and its relation to LCST are broadly known in the chemical arts. The devices described herein are prepared from decellularized, intact ECM as described below, by digestion of the ECM material with an acid protease, neutralization of the material to form a pre-gel, inserting a polymeric mesh into the pre-gel and then raising the temperature of the pre-gel above the LCST of the pre-gel to cause the pre-gel to gel. As used herein, the term "gel" includes hydrogels.

As used herein, the terms "extracellular matrix" and "ECM" refer to a natural scaffolding for cell growth. Natural ECMs (ECMs found in multicellular organisms, such as mammals and humans) are complex mixtures of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, small intestine submucosa (SIS), urinary bladder matrix (UBM), liver stroma ECM, and dermal ECM each differ in their overall structure and composition due to the unique cellular niche needed for each tissue.

As used herein, the terms "intact extracellular matrix" and "intact ECM" refers to an extracellular matrix that retains activity of at least a portion of its structural and non-structural biomolecules, including, but not limited to, collagens, elastins, laminins, glycosaminoglycans, proteoglycans, antimicrobials, chemoattractants, cytokines, and/or growth factors, such as, without limitation comminuted ECM as described herein. The activity of the biomolecules within the ECM can be removed chemically or mechanically, for example, by cross-linking and/or by dialyzing the ECM. Intact ECM essentially has not been cross-linked and/or dialyzed, meaning that the ECM has not been subjected to a dialysis and/or a cross-linking process, or conditions other than decellularization processes or processes that occur as part of storage and handling of ECM prior to solubilization, as described herein. Thus, ECM that is substantially cross-linked and/or dialyzed (in anything but a trivial manner which does not substantially affect the gelation and functional characteristics of the ECM in its uses described herein) is not considered to be "intact".

ECM, for example intact ECM is typically prepared by the decellularization of tissues prior to use. As indicated above, decellularization is performed to prevent a pro-inflammatory response. As such, a decellularized ECM product or a decellularized intact ECM product is used herein to refer to ECM material that is decellularized to the extent that a pro-inflammatory response, and thus growth of fibrotic tissue is not is not elicited to any substantial degree in favor of constructive remodeling; for example and without limitation, resulting in a M2 macrophage phenotype rather than an M1 macrophage phenotype, responses characteristic of the M2 phenotype rather than responses characteristic of an M1 phenotype, and/or resulting in a greater proportion of M2 macrophage as compared to M1 macrophage in response to implantation of the ECM material in a mammal.

By "bio compatible", it is meant that a device, scaffold composition, etc. is essentially, practically (for its intended use) and/or substantially non-toxic, non-injurous or non-inhibiting or non-inhibitory to cells, tissues, organs, and/or organ systems that would come into contact with the device, scaffold, composition, etc.

In general, the method of preparing an ECM-derived gel requires the isolation of ECM from an animal of interest and from a tissue or organ of interest. In certain embodiments, the ECM is isolated from mammalian tissue. As used herein, the term "mammalian tissue" refers to tissue derived from a mammal, wherein tissue comprises any cellular component of an animal. For example and without limitation, tissue can be derived from aggregates of cells, an organ, portions of an organ, or combinations of organs. In certain embodiments, the ECM is isolated from a vertebrate animal, for example and without limitation, human, monkey, pig, cattle, and sheep. In certain embodiments, the ECM is isolated from any tissue of an animal, for example and without limitation, urinary bladder, liver, small intestine, esophagus, pancreas, dermis, and heart. In one embodiment, the ECM is derived from a urinary bladder. The ECM may or may not include the basement membrane portion of the ECM. In certain embodiments, the ECM includes at least a portion of the basement membrane. The ECM may or may not retain some of the cellular elements that comprised the original tissue such as capillary endothelial cells or fibrocytes. In one embodiment, the ECM is derived from dermal tissue.

As used herein, the term "derive" and any other word forms or cognates thereof, such as, without limitation, "derived" and "derives", refers to a component or components obtained from any stated source by any useful method. For example and without limitation, an ECM-derived gel refers to a gel comprised of components of ECM obtained from any tissue by any number of methods known in the art for isolating ECM. In another example, mammalian tissue-derived ECM refers to ECM comprised of components of a particular mammalian tissue obtained from a mammal by any useful method.

As stated above, provided herein are surgical meshes embedded within an ECM-derived gel. The surgical mesh may be any suitable mesh that is useful for implantation in surgery. Those of skill in the art will understand that any mesh that is suitable for implantation into an animal or human for repairing a defect will be useful in the present devices and methods. Suitable polymeric surgical meshes may be formed from any bio compatible and/or FDA-approved material, for example and without limitation, PLA (polylactic acid), PGA (polyglycolide), PLGA (poly(lactic-co-glycolic) copolymers, polyethylene, polyurethanes, polyester urethane urea (PEUU), poly(ether ester urethane)urea (PEEUU), silicones, polyaryl ether ketones, polyether ketone ketones, polyether block amides, polytetrafluoroethylene (PTFE, e.g., TEFLON™), polyoxymethylene, polyethylene terephthalate, polypropylene polycaprolactone (PCL), poly-4-hydroxybutyrate, polycarbonate, poly(ester carbonate urethane)urea (PECUU), and/or copolymers or block copolymers thereof and meshes that consist of fibers composed of different polymers, for example and without limitation a mesh with discrete knitted fibers of PEUU and polypropylene. Non-polymeric surgical meshes comprise compositions including, for example and without limitation: stainless steel, gold, silver, platinum, titanium and titanium alloys, tantalum, cobalt chrome alloys, carbon fibers (graphite or diamond), hydroxyapatite and other calcium phosphate materials (e.g., BIOGLASS™) Additionally, the mesh may be fabricated from combinations of any of the above materials. Surgical meshes may also be purchased from commercial suppliers. For example, meshes are commercially available from manufacturers such as C.R. Bard-Davol (Providence, R.I.) under the trade names BARD™ Mesh and BARD™ Soft Mesh, and from Ethicon (San Angelo, Tex.) under the trade name ULTRAPRO™. In one embodiment, the mesh is a synthetic polymer. In further embodiments, the mesh is polypropylene.

Meshes suitable for use in the present devices and methods may have any suitable pore size, that is, the size of the gaps or "holes" between fibers of the mesh. Meshes with larger gaps or "holes" are referred to as lightweight meshes, and those with smaller gaps or "holes" are referred to as heavyweight meshes. Suitable pore size for use in the present devices and methods are those with a pore size greater than 0 µm. In some embodiments, the pore size of the mesh ranges from 0.01 µm to 5 mm and increments therebetween. In one embodiment, the mesh is a lightweight mesh. A suitable mesh for use in the present devices and methods may be lightweight, heavyweight, or any combination of both. Individual mesh fibers may be monofilament or braided multifilament, and may be manufactured to possess diverse weaves or knit structures.

Also provided herein are methods of preparing a surgical mesh for implantation. The method includes the steps of producing or providing an ECM-derived pre-gel (digest solution), immersing a surgical mesh in the digest solution, and gelling the solution to produce a mesh embedded in the ECM-derived gel. The ECM-derived pre-gel is a solution that becomes more viscous as it is warmed. In one embodiment, the pre-gel solution is warmed to 10° C. In another embodiment, the pre-gel solution is warmed to room temperature (approximately 20° C. to 25° C.) to form the hydrogel. In another embodiment, the pre-gel solution is warmed to at least about 37° C. to form the hydrogel. According to one embodiment, the ECM-derived composition is a solution at temperatures lower than 37° C., but a hydrogel at a physiological temperature of 37° C. or higher.

Tissue for preparation of ECM and ECM-derived pre-gel solutions and gels can be harvested in a large variety of ways and once harvested, a variety of portions of the harvested tissue may be used. For example and without limitation, in one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa can be removed mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa can also be dissociated by soaking the tissue in a de-epithelializing solution, for example and without limitation, hypertonic saline. The resulting UBM comprises basement membrane of the tunica mucosa and the adjacent tunica propria, which is further treated with peracetic acid, lyophilized and powdered.

In another embodiment, dermal tissue is used as the source of ECM. Dermal tissue may be obtained from any mammalian source, such as human, monkey, pig, cow and sheep. In one embodiment, the source is porcine. Porcine skin from the dorsolateral flank of market weight pigs immediately can be harvested and processed by soaking in water or distilled water. All samples were then delaminated to remove subcutaneous fat, connective tissue and the epidermis. The harvested sheets of porcine dermis are immediately frozen at −80° C.

Dermis sections may be decellularized with 0.25% Trypsin/1% Triton X-100 (i.e. no SDS) on a vortex shaker at 300 RPM at room temperature in the following solutions: 0.25% trypsin for 6 hours, 1×; deionized water, 15 minutes, 3×; 70% ethanol, 10 to 12 hours, 1×; 3% $H_2O_2$, 15 minutes, 1×, deionized water, 15 minutes, 2×; 1% Triton X-100 in 0.26% EDTA/0.69% Tris, 6 hours, 1× and then overnight, 1×; deionized water, 15 minutes, 3×; 0.1% peracetic acid/4% ethanol, 2 hours, 1×; PBS, 15 minutes, 2×; and finally deionized water, 15 minutes, 2×. Dermis sheets are then lyophilized and subsequently reduced to particulate form using a Waring blender and a Wiley Mill with a #20 mesh screen.

In another embodiment, the epithelial cells can be delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

In one embodiment, the ECM is prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM consists mainly of the tunica submucosa.

Following isolation of the tissue of interest, decellularization is performed by various methods, for example and without limitation, exposure to hypertonic saline, peracetic acid, Triton-X or other detergents. Sterilization and decellularization can be simultaneous. For example and without limitation, sterilization with peracetic acid, described above, also can serve to decellularize the ECM. As indicated above, decellularized ECM is decellularized to an extent that avoids elicitation of a pro-inflammatory (e.g., M1 macrophage phenotype) response, and means that there is a sufficiently low concentration or amounts of DNA, phospholipid, and/or mitochondrial material in the resulting solution. In certain embodiments, the ECM is considered decellularized when there is less than 50 ng DNA/mg ECM in the decellularized ECM, digest solution and/or resulting pre-gel solution. In other embodiments, the ECM is considered decellularized when there is less than 750 nmol phospholipids/g ECM in the solution and/or resulting pre-gel solution.

Decellularized ECM can then be dried, either lyophilized (freeze-dried) or air dried. The ECM is optionally comminuted at some point prior to enzymatic digestion, for example prior to or after decellularization and/or drying. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state.

As used herein, the term "comminute" and any other word forms or cognates thereof, such as, without limitation, "comminution" and "comminuting", refers to the process of reducing larger particles into smaller particles, including, without limitation, by grinding, blending, shredding, slicing, milling, cutting, shredding. ECM can be comminuted while in any form, including, but not limited to, hydrated forms, frozen, air-dried, lyophilized, powdered, sheet-form.

In order to prepare solubilized ECM tissue, comminuted ECM is digested with an acid protease in an acidic solution to form a digest solution. As used herein, the term "acid protease" refers to an enzyme that cleaves peptide bonds, wherein the enzyme has increased activity of cleaving peptide bonds in an acidic pH. For example and without limitation, acid proteases include pepsin and trypsin and mixtures thereof.

The digest solution of ECM typically is kept at a constant stir for a certain amount of time at room temperature. The ECM digest can be used immediately or be stored at −20° C. or frozen at, for example and without limitation, −20° C. or −80° C. In certain embodiments, the ECM digest is snap frozen in liquid nitrogen. To form a "pre-gel" solution, the pH of the digest solution is raised to a pH between 7.2 and 7.8. The pH can be raised by adding one or more of a base or an isotonic buffered solution, for example and without limitation, NaOH or PBS at pH 7.4. The method typically does not include a dialysis step prior to gelation, yielding a more-complete ECM-like matrix that typically gels at 37° C. more slowly than comparable collagen or dialyzed ECM preparations. In certain embodiments, dialysis, or similar methods, are not used. The gel is therefore is more amenable to use with an implantable surgical mesh, and further also retains more of the qualities of native ECM due to retention of many native soluble factors, such as, without limitation, cytokines. These factors contribute to chemoattraction of cells and proper rearrangement of tissue at the site of injury, rather than fibrous response that leads to unwanted scarring.

As used herein, the term "isotonic buffered solution" refers to a solution that is buffered to a pH between 7.2 and 7.8, e.g., pH 7.4, and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain embodiments, the base is NaOH or NaOH in PBS.

Figure 1:
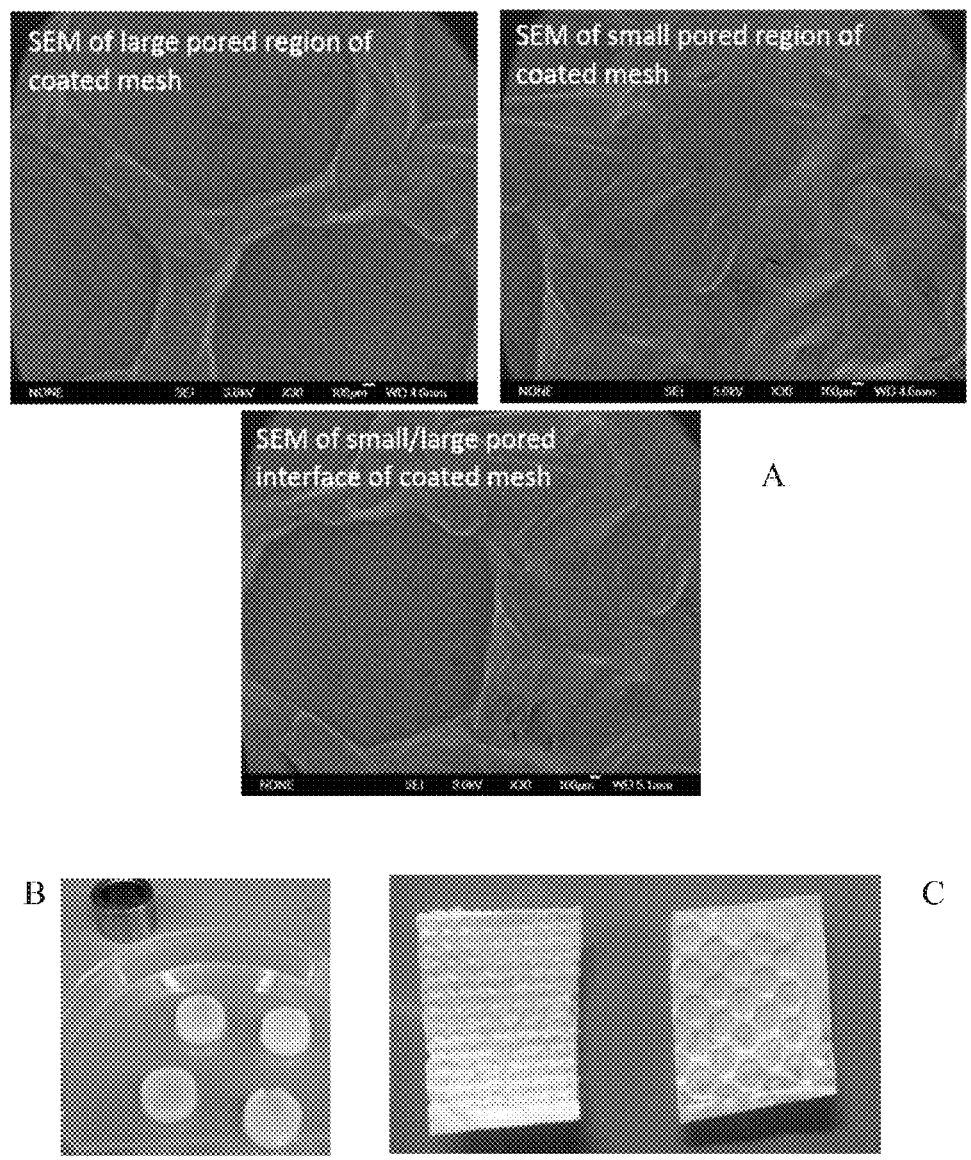
FIG. 1 shows A. scanning electron microscopy (SEM) images of a surgical mesh coated with an ECM-derived gel; B. meshes embedded in an ECM-derived gel; and C. meshes coated with an ECM-derived gel according to one embodiment of the present invention.

This "pre-gel" solution can, at that point be incubated at a suitably warm temperature, for example and without limitation, at about 37° C. to gel. The mesh is immersed in the pre-gel solution prior to gelation, and then the gel is raised to the gelling temperature (e.g., above 25° C., 37° C. or above 37° C.). As shown in FIG. 1, the gel coats the mesh, which is embedded therein. FIG. 1(B) shows four meshes embedded within gels after the pre-gel solution is gelled at 37° C. The excess ECM-derived gel can be scraped or cut away, providing the embedded/coated meshes shown in FIG. 1(C). The left mesh in FIG. 1(C) is a heavyweight mesh (smaller pore sizes) and the right mesh is a lightweight mesh (larger pore sizes). FIG. 1 shows SEM images of both lightweight (upper left) and heavyweight (upper right) meshes, as well as at the interface of large and small pores in a combination mesh (bottom).

Alternately, the pre-gel can be frozen and stored at, for example and without limitation, −20° C. or −80° C., for eight or more hours. As used herein, the term "pre-gel solution" or "pre-gel" refers to a digest solution wherein the pH is increased. For example and without limitation, a pre-gel has a pH between 7.2 and 7.8, for example 7.4. The gel, once formed around the mesh, can be further frozen and/or lyophilized to form a foam. For example, the embedded mesh may be frozen and stored at, −20° C. or −80° C., or any temperature therebetween for eight or more hours. The embedded mesh may also be snap frozen in liquid nitrogen. Lyophilization may occur at room temperature or at below room temperature, for example at 0° C., −10° C., −20° C., −30° C., and lower.

The concentration of ECM in the pre-gel solution, or in the final gel, may be any concentration that allows for formation of a gel that is effective for the uses described herein. In some embodiments, the concentration of ECM in the pre-gel solution and/or gel is at least 1 mg/ml, at least 2 mg/ml, at least 3 mg/ml, at least 4 mg/ml, at least 5 mg/ml, at least 6 mg/ml, at least 7 mg/ml, at least 8 mg/ml, at least 9 mg/ml, at least 10 mg/ml, at least 20 mg/ml, or at least 30 mg/ml.

According to certain embodiments, the gel is bioactive because the intact, decellularized ECM is solubilized and is not dialyzed, cross-linked and/or otherwise treated to remove or otherwise inactivate ECM structural or functional components, resulting in a highly bioactive gel scaffold that is functionally superior to earlier-described matrices. A general set of principles for preparing an ECM-derived gel is provided along with specific protocols for preparing gels from numerous tissues, including dermis, urinary bladder, spleen, liver, heart, pancreas, ovary and small intestine.

Any useful cytokine, chemoattractant or cells can be mixed into the composition prior to gelation or diffused, absorbed and/or adsorbed by the gel after it is gelled. For example and without limitation, useful components include growth factors, interferons, interleukins, chemokines, monokines, hormones, angiogenic factors, drugs and antibiotics. Cells can be mixed into the neutralized solubilized gel or can be placed atop the molded composition, having the mesh embedded therein, once it is gelled. In either case, when the gel is seeded with cells, the cells can be grown and/or adapted to the niche created by the molded ECM gel by incubation in a suitable medium in a bioreactor or incubator for a suitable time period to optimally/favorably prepare the composition for implantation in a patient. The molded composition can be seeded with cells to facilitate in-growth, differentiation and/or adaptation of the cells. For example and without limitation, the cells can be autologous or allogeneic with respect to the patient to receive the composition/device comprising the gel. The cells can be stem cells or other progenitor cells, or differentiated cells. In one example, a layer of dermis obtained from the patient is seeded on a mold, for use in repairing damaged skin and/or underlying tissue.

As used herein, the term "mold" refers to a cavity or surface used to form the gel around the mesh, and into a three-dimensional shape. For example and without limitation, the mold can be a well plate, cell culture dish or a tube or can be shaped into any useful shape. The mesh is provided in the mold, and the pre-gel is then delivered to the mold to envelop the mesh, in a variety of possible methods, including, but not limited to, injection and deposition, for gelation and formation of the gel/hydrogel.

As used herein, the terms "drug" and "drugs" refer to any compositions having a preventative or therapeutic effect, including and without limitation, antibiotics, peptides, hormones, organic molecules, vitamins, supplements, factors, proteins and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

The pre-gel solution may be pre-seeded with cells, or any other useful factor for promoting proper tissue reorganization and growth, as described above. In another non-limiting embodiment, the composition is gelled and then the gel, with the mesh embedded therein, is seeded with cells or any other useful factor as described above.

The ECM-coated mesh can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. More typically, the ECM-coated mesh is disinfected by immersion in 0.1% (v/v) peracetic acid (σ), 4% (v/v) ethanol, and 96% (v/v) sterile water for 2 h. The ECM-coated mesh is then washed twice for 15 min with PBS (pH=7.4) and twice for 15 min with deionized water.

Non-limiting examples of extracellular matrix preparations are described in U.S. Pat. Nos. 4,902,508; 4,956,178; 5,281,422; 5,352,463; 5,372,821; 5,554,389; 5,573,784; 5,645,860; 5,711,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666. In certain embodiments, the ECM is isolated from a vertebrate animal, for example and without limitation, from a warm-blooded mammalian vertebrate animal including, but not limited to, human, monkey, pig, cow and sheep. The ECM can be derived from any organ or tissue, including without limitation, urinary bladder, intestine, liver, esophagus and dermis. In one embodiment, the ECM is isolated from a urinary bladder. The ECM may or may not include the basement membrane portion of the ECM. In certain embodiments, the ECM includes at least a portion of the basement membrane. In other embodiments, the ECM is isolated from dermal tissue.

In addition to producing ECM as described above, commercially-available ECM preparations can also be used in the devices and methods described herein. In one embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton Mass.). In another embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (Acell Corporation; Jessup, Md.).

One favorable aspect of the use of pre-molded tissue is that a layered composition can be produced into which the mesh is embedded. For example, a core portion of the composition to be implanted can be prepared with a first ECM hydrogel, obtained from a first source, and a surrounding layer can be with a second ECM hydrogel, obtained from a second source different from the first, or the same source as the first, but containing different constituents, such as cytokines or cells.

In another embodiment of the pre-molded composition, the ECM hydrogel into which the mesh is embedded is contained within a laminar sheath of non-comminuted and non-digested decellularized ECM, such as SIS or UBM, to add physical strength to the gel. In this embodiment, sheets of decellularized ECM, prepared in any manner known in the art, can be placed into the mold prior to filling the mold with the solubilized ECM material for producing the gel. The sheets of decellularized ECM may be used as the mold, so long as they are formed and sewn or cross-linked into a desired shape. In this manner, a solid composition can be produced that has greater physical strength than is the case of a hydrogel, alone.

In a further embodiment, a commercial kit is provided comprising a composition described herein. A kit comprises suitable packaging material and the composition. In one non-limiting embodiment, the kit comprises a pre-gel in a vessel, which may be the packaging, or which may be contained within packaging. In this embodiment, the pre-gel typically is frozen or kept at near-freezing temperatures, such as, without limitation, below about 4° C. In another non-limiting embodiment, the kit comprises a first vessel containing an acidic solution comprising digest solution of ECM as described herein, a second vessel comprising a neutralizing solution comprising a base and/or buffer(s) to bring the acidic solution of the first vessel to physiological ionic strength and pH, to form a pre-gel, and a mesh. This kit also optionally comprises a mixing needle and/or a cold-pack. The vessel may be a vial, syringe, tube or any other container suitable for storage and transfer in commercial distribution routes of the kit.

In yet another embodiment of the kit, a pre-gel composition is molded around a mesh and pre-gelled prior to packaging and distribution. In one embodiment, the molded gel is packaged in a blister-pack comprising a plastic container and a paper, plastic and/or foil sealing portion, as are well-known in the art. The molded structure and packaging typically is sterilized prior to or after packaging, for example and without limitation, by gamma irradiation. The molded structure may be packaged in any suitable physiological solution, such as PBS or saline. If the molded gel contains live cells, the mold can be transported in a suitable cell-culture medium in a sealed jar or other vessel. Of course, the cell-containing molded gel would have to be shipped in an expedited manner to preserve the cells.

In addition to a pure ECM-derived gel, a hybrid inorganic/ECM gel and/or scaffold may be utilized in the devices and methods of the present invention. As used herein, the term "hybrid inorganic/ECM scaffold" refers to an ECM-derived gel that includes a synthetic component, such as PEUU and/or PEEUU.

Also provided herein are methods of repairing a defect in a body, such as a wound or congenital defect, including the steps of integrating a surgical mesh embedded in an ECM-derived gel at the site of a defect in a patient. As used herein, "patient" may refer to any mammal. In some embodiments, the mammal is a human being. The ECM gel-embedded mesh may be used to repair and/or treat any defect that would benefit from the implantation or integration of a surgical mesh. For example, breast reconstruction, hernias, and defects in the pelvic floor including pelvic floor dysfunction, pelvic organ prolapse, postpartum pelvic floor dysfunction, pelvic pain, incontinence (including urinary and fecal incontinence), abdominal wall injuries, and the like. Those of skill are aware of the typical applications for surgical meshes, and the devices described herein will be useful for reducing the inflammatory/immunologic response in those applications. Mesh fixation may occur using sutures, staples, or any other means for integrating or attaching a mesh known to those of skill in the art. In some embodiments, single interrupted sutures are used at the corners of a square or rectangular-shaped mesh with two additional sutures utilized at the midpoint of the long edge(s) of a rectangular mesh. In other embodiments, uninterrupted sutures applied along the perimeter of the mesh may be utilized.

EXAMPLES

Example 1—Preparation of Porcine Extracellular Matrix (ECM) (UBM)

The preparation of UBM has been previously described. In brief, porcine urinary bladders were harvested from 6-month-old 108-118 kg pigs (Whiteshire-Hamroc, Ind.) immediately following euthanasia. Connective tissue and adipose tissue were removed from the serosal surface and any residual urine was removed by repeated washes with tap water. The tunica serosa, tunica muscularis externa, the tunica submucosa, and majority of the tunica muscularis mucosa were mechanically removed. The urothelial cells of the tunica mucosa were dissociated from the luminal surface by soaking the tissue in 1.0 N saline solution yielding a biomaterial composed of the basement membrane plus the subjacent tunica propria, which is referred to as urinary bladder matrix (UBM).

The UBM sheets were disinfected for two hours on a shaker in a solution containing 0.1% (v/v) peracetic acid, 4% (v/v) ethanol, and 95.9% (v/v) sterile water. The peracetic acid residue was removed by washing with sterile phosphate-buffered saline (pH=7.4) twice for 15 minutes each and twice for 15 minutes each with sterile water. The UBM sheets were then lyophilized using an FTS Systems Bulk Freeze Dryer Model 8-54 and powdered using a Wiley Mini Mill.

One gram of lyophilized UBM powder and 100 mg of pepsin were both mixed in 100 ml of 0.01 M HCl. The solution was kept at a constant stir for ~48 hrs at room temperature (25° C.). After pepsin digestion, the digest solution was aliquoted and stored at −20° C. until use. After completion, the solution is referred to as digest solution or ECM digest or ECM stock solution.

Example 2—Preparation of Porcine Spleen ECM

Fresh spleen tissue was obtained. Outer layers of the spleen membrane were removed by slicing, where remaining tissue was cut into uniform pieces. Remnants of outer membrane were trimmed, then rinsed three times in water. Water was strained by using a sieve. Splenocytes were lysed by massaging. Spleen slices were incubated in a solution of 0.02% trypsin/0.05% EDTA at 37° C. for 1 hour in a water bath. If necessary, splenocytes were further lysed by massaging. After rinsing, slices were soaked in 3% Triton X-100 solution and put on a shaker for 1 hour. If necessary, splenocytes were further lysed by massaging. Slices were then soaked in 4% deoxycholic acid solution and put on a shaker for 1 hour. After thoroughly rinsing, the purified spleen ECM was stored for further processing. This tissue was next disinfected with peracetic acid treatment and dried.

One gram of dry porcine spleen ECM and 100 mg of pepsin were both mixed in 100 ml of 0.01 M HCl. The solution was kept at a constant stir for ~72 hrs at room temperature (25° C.). If there are no visible pieces of the ECM floating in the solution, aliquot the sample and freeze (−20° C.) or use immediately.

Example 3—Preparation of Porcine Liver Stroma ECM

Fresh liver tissue was obtained. Excess fat and tissue were trimmed. Outer layers of the liver membrane were removed by slicing, where remaining tissue was cut into uniform pieces. Remnants of outer membrane were trimmed using a scalpel or razor blade, then rinsed three times in water. Water was strained by using a sieve. Cells were lysed by massaging. Liver slices were incubated in a solution of 0.02% trypsin/0.05% EDTA at 37° C. for 1 hour in a water bath. If necessary, cells were further lysed by massaging. After rinsing, slices were soaked in 3% Triton X-100 solution and put on a shaker for 1 hour. If necessary, cells were further lysed by massaging. Slices were then soaked in 4% deoxycholic acid solution and put on a shaker for 1 hour. After thoroughly rinsing, the purified liver stroma was stored in deionized water for further processing. This tissue was next disinfected with peracetic acid treatment and dried.

One gram of dry porcine liver stroma ECM and 100 mg of pepsin were both mixed in 100 ml of 0.01 M HCl. The solution was kept at a constant stir for ~24-48 hrs at room temperature (25° C.). If there are no visible pieces of the ECM floating in the solution, aliquot the sample and freeze (−20° C.) or use immediately.

Example 4—Preparation of Human Liver Stroma ECM

Fresh liver tissue was obtained. Excess fat and tissue were trimmed. Outer layers of the liver membrane were removed by slicing, where remaining tissue was cut into uniform pieces. Remnants of outer membrane were trimmed using a scalpel or razor blade, then rinsed three times in water. Water was strained by using a sieve. Cells were lysed by massaging. Liver slices were incubated in a solution of 0.02% trypsin/0.05% EDTA at 37° C. for 1 hour in a water bath. If necessary, cells were further lysed by massaging. After rinsing, slices were soaked in 3% Triton X-100 solution and put on a shaker for 1 hour. If necessary, cells were further lysed by massaging. Slices were then soaked in 4% deoxycholic acid solution and put on a shaker for 1 hour. After thoroughly rinsing, the purified liver stroma was stored in deionized water for further processing. This tissue was next disinfected with peracetic acid treatment and dried.

One gram of dry human liver stroma ECM and 200 mg of pepsin were both mixed in 50 ml of 0.01 M HCl. The solution was kept at a constant stir for ~3-5 days at room temperature (25° C.). The solution will need to be monitored every day. If there are no visible pieces of the ECM floating in the solution, aliquot the sample and freeze (−20° C.) or use immediately.

Example 5—Preparation of Porcine Cardiac ECM

One gram of dry porcine cardiac ECM with 100 mg of pepsin were both mixed in 50 mL of 0.01 M HCl. The solution was kept at a constant stir for ~48 hours at room temperature (25° C.).

Example 6—Preparation of Porcine Pancreatic ECM

One gram of dry de-fatted porcine pancreatic ECM with 100 mg of pepsin were both mixed in 50 mL of 0.01 M HCl. The solution was kept at a constant stir for ~48 hours at room temperature (25° C.).

Example 7—Preparation of Porcine Ovarian ECM

Fresh ovarian tissue is obtained within 6 hours of harvest. Ovaries were removed and stored in physiological saline tissue until ready for dissection and residual uterine tissue was removed. Longitudinal incisions were made through the hilum of the ovary and the follicles were disrupted. Once all the follicles have been disrupted, the ECM has been harvested from the ovaries. Rinse three times in filtered water and strain the water using a sieve. Cells were lysed by gentle massaging. ECM was incubated in a solution of 0.02% trypsin/0.05% EDTA at 37° C. for 1 hour in a water bath and then rinsed. If necessary, cells were further lysed by massaging. ECM was soaked in 3% Triton X-100 solution and put on a shaker for 1 hour. After rinsing, cells were further lysed by massaging if necessary. Slices were then soaked in 4% deoxycholic acid solution and put on a shaker for 1 hour. After thoroughly rinsing to remove residual surfactant, the ECM was stored in sterile/filtered water until further use. This tissue was next disinfected with peracetic acid treatment and dried.

One gram of lyophilized ovarian ECM powder and 100 mg of pepsin were both mixed in 100 ml of 0.01 M HCl. The solution was kept at a constant stir for ~48 hrs at room temperature (25° C.). After pepsin digestion, the digest solution was aliquoted and stored at −20° C. until use.

Example 8—General Method of Preparation of Gels from ECM

UBM gel was formed into a gel by mixing 0.1 N NaOH (1/10 of the volume of digest solution) and 10×PBS pH 7.4 (1/9 of the volume of digest solution) in appropriate amounts at 4° C. The solution was brought to the desired volume and concentration using cold (4° C.) 1×PBS pH 7.4 and placed in a 37° C. incubator for gelation to occur.

The ECM was able to form a matrix after 40 minutes in solution. The ECM-derived gel was liquid at temperatures below 20° C. but turn into a gel when the temperature is raised to 37° C.

In preparing gels from ECM, all of the following solutions should be kept on ice and the following variables must be determined:

$C_f$=concentration of the final gel in mg/ml
$C_s$=concentration of the ECM digest solution in mg/ml
$V_f$=volume of the final gel solution needed for the experiments
$V_d$=volume needed from the ECM digest solution in ml
$V_{10X}$=volume of 10×PBS needed in ml
$V_{1X}$=volume of 1×PBS needed in ml
$V_{NaOH}$=volume of 0.1 N NaOH needed in ml First, determine the final concentration ($C_f$) and volume ($V_f$) of ECM gel required. Then, calculate the mass of ECM needed by multiplying $C_f$ (mg/ml)*$V_f$ (ml). This value will give you the volume needed from the ECM digest solution ($V_d$), where $V_d$=[$C_f$ (mg/ml)*$V_f$(ml)]/$C_s$.

Calculate the volume of 10×PBS needed by dividing the calculated volume $V_d$ by 9 ($V_{10X}$=$V_d$/9). Calculate the volume of 0.1 N NaOH needed by dividing the calculated volume $V_d$ by 10 ($V_{NaOH}$=$V_d$/10). Calculate the amount of 1×PBS needed to bring the solution to the appropriate concentration/volume as follow: $V_{1X}$=$V_f$−$V_d$−$V_{10X}$−$V_{NaOH}$. Add all the reagents ($V_{1X}$+$V_d$+$V_{10X}$+$V_{NaOH}$) to an appropriate container (usually 15 or 50 ml centrifuge tubes) without the ECM digest ($V_d$). Place solutions on ice and keep on ice at all times.

Add the appropriate volume from the ECM digest solution ($V_d$) to the PBS/NaOH mixture prepared above and mix well with a 1 ml micropipette while being careful and avoiding the creation of air bubbles in the solution. Depending on the viscosity of the ECM digest solution, there might be some significant volume loss during the transfer. Monitor the total volume and add appropriate amounts until the final volume is achieved. Measure the pH of the pre-gel solution, where pH should be around 7.4.

Add the pre-gel solution to a mold or to appropriate wells. Place the mold or wells in 37° C. incubator for a minimum of 40 minutes. Avoid using an incubator with $CO_2$ control. If water evaporation is a concern, place the mold inside a plastic zip-lock bag before placing in the incubator. After gelation, the gel can be removed from the mold and placed on 1×PBS. If the gels were made in tissue culture plates, 1×PBS can be placed on top of the gels until use to maintain the gels hydrated.

Sample calculation: Make 6 ml of gel with a final concentration of 6 mg/ml from the 10 mg/ml stock solution.
GIVEN: $C_s$=10 mg/ml; $C_f$=6 mg/ml; $V_f$=6 ml
$V_d$=[6 mg/ml*6 ml]/10 mg/ml=3.600 ml
$V_{10X}$=3.6/9=0.400 ml
$V_{NaOH}$=3.6/10=0.360 ml
$V_{1X}$=6 ml−3.6 ml−0.400 ml−0.360=1.640 ml Example 9—Coating BARD™ Mesh and BARD™ Soft Mesh with Dried Dermal ECM Hydrogel for Implantation Methods 100 ml of 0.01 M HCl was prepared and sterile filtered, and 100 mg of porcine pepsin was added in sterile beaker and stirred. 1 g of dermal ECM powder was added to solution at high stir rate (vortex just reaching stirbar). The dermal ECM powder was digested for 48 hours at room temperature and then transferred to 50 ml conical tubes stored at 4° C. The gelation capacity of the digest was verified by making 8 mg/ml gels in cell seeding rings as shown in Example 8. Two 45 ml, 8 mg/ml pre-gel solutions were then prepared the following day on ice using sterile, filtered 10×PBS, 0.1 M NaOH, and 1×PBS. In brief, 36 ml of ECM digest was neutralized with filtered reagents on ice and with extensive mixing: 4 ml of 10×PBS, 3.6 ml of 0.1M NaOH, and 1.4 ml of 1×PBS.

The digest was then added over mesh devices in 2 plates, as follows: Square petri dishes were lined with non-stick foil (all wrinkles in foil pressed out) and meshes were placed in foil lined dishes. Ten 2 cm×3 cm mesh devices were laid flat with no overlap, and 1×1 cm square of Tropicana added in unoccupied corner; ~42 ml of pre-gel evenly was added over the mesh devices in each plate, and all bubbles were pressed out from underneath the mesh devices. Meshes were positioned approximately ⅓ distance from the bottom of plate to the surface of pre-gel, so that an equivalent amount of digest was on each side, evenly, after the meshes started to rise during gelation.

Petri dishes containing the digest and meshes were placed in a non-humidified incubator for 1 hour at 37° C. to gel. After gelation was confirmed, the dishes remained in the incubator for ~30 hours (loosely covered). After the gels completely dried, the meshes were removed from the dish and excess ECM coating was cut away. The coated meshes were then sterilized with ethylene oxide (EtO) for implantation.

Results

The digest increased in viscosity after the first day, but did not increase to the point where the stir bar had any trouble spinning in the digest. The digest was able to gel effectively in rings and around the mesh devices in the dish. The ECM gel coatings appeared even around and between mesh fiber pores for all devices.

Example 10—Coating Polypropylene Mesh with 8.0 mg/ml Porcine Dermal ECM Digest Method A pre-gel solution (2 ml), having a final ECM concentration of 8 mg/ml, was prepared with the following components: 1.6 ml porcine dermal ECM pepsin digest; 0.178 ml 10×PBS; 0.160 ml 0.1 N NaOH; and 0.062 ml 1×PBS. The mesh utilized was a 15 cm×15 cm BARD™ monofilament knitted polypropylene mesh, and two 2.5 cm×2.5 cm squares were cut from the mesh. Tissue culture rings were placed on top of the squares in a petri dish and 0.5 ml of pre-gel was pipetted in each of the two rings. A ~1 cm diameter mesh circle was cut and placed inside of a ring with 0.5 ml of digest. Pre-gel solutions were placed in 37° C. non-humidified incubator for 1.5 hours. After 1.5 hours, the gels were examined, and the mesh coated with gel solution was left overnight for the water to evaporate and stored in a petri dish.

Results

The pre-gel spread out onto the gel after 1.5 hours and the meshes were fully coated.

Conclusions

Porcine dermal digest can be used to coat polypropylene BARD™ mesh. Under gross inspection, there appeared to be dried digest around the fibers of all of the meshes, as well as between fiber gaps. Two different gels were then tested.

Method

A pre-gel solution (2 ml), having a final ECM concentration of 8 mg/ml, was prepared with the following components: 1.6 ml porcine dermal ECM pepsin digest (A1 or B2 processes); 0.178 ml 10×PBS; 0.160 ml 0.1 N NaOH; and 0.062 ml 1×PBS. The A1 and B2 dermal ECM processing methods are described in Reing et al. 2012. In brief, A1 processed dermis has been mechanically split and limed, and decellularized with a single SDS exposure as the primary detergent step. B2 processed dermis was split but not limed, and included acetone and hydrogen peroxide during decellularization and incorporated 2 separate detergent exposures (a 6 hour exposure followed by an overnight exposure). The mesh utilized was a 15 cm×15 cm BARD™ monofilament knitted polypropylene mesh, and two 2.5 cm×2.5 cm squares were cut from the mesh. 0.5 ml of digest was put on the plate, the mesh was placed on top of the digest, and then another 0.5 ml of digest was added. Digests with mesh were then frozen and placed in a lyophilizer for 24 hours. Upon removal, the vacuum was released too quickly and the A mesh was blown out of its plate, no disruption in architecture was observed, however.

Results and Conclusion

Lyophilized porcine dermal digest can be used to coat polypropylene BARD™ mesh. Both A1 and B2 digest preparations appeared to have formed a fluffy coat around the mesh. SEM is needed to view this microscopically, and cell interaction must be determined as well to determine usefulness of this technique. Porcine dermal digest coated BARD™ mesh was then visualized using scanning electron microscopy (SEM).

Method

Coated BARD™ mesh samples as described above were taken for SEM preparation. Dried and lyophilized samples as described above were used. The dried (in a 37 C incubator) samples were fixed/washed and the lyophilized samples were divided into fixed/not fixed groups. The fixation procedure was as follows: Immersion in 2.5% glutaraldehyde for 1 hour; 3×15 min PBS washes; 15 min wash in 50% ethanol; and 3×15 min washes in 100% ethanol. Samples were then cut into 8 mm×8 mm squares and a 3.5 nm sputter coat applied.

Results and Conclusion

SEM analysis showed some digest adherence on all samples, but the most significant coating appeared on the (washed) lyophilized B2 digest and air dried A1 digest. The lyophilized images confirmed the highly porous digest matrix around the fibers. It was shown that the fixation/wash procedure is not required (i.e. there were no salt crystals visible on the unwashed lyophilized samples), only a sputter coating is needed for preparation. Various dermal ECM digest coating methods on BARD™ polypropylene mesh were visualized using SEM.

Method

A pre-gel solution (2 ml), having a final ECM concentration of 8 mg/ml, was prepared with the following components: 1.6 ml porcine dermal ECM pepsin digest (B2—described above); 0.178 ml 10×PBS; 0.160 ml 0.1 N NaOH; and 0.062 ml 1×PBS. The mesh utilized was a 15 cm×15 cm BARD™ monofilament knitted polypropylene mesh, and twenty-two 0.8 mm×0.8 mm squares were cut from the mesh. Three different coating methods were then attempted:

Air Drying: approximately 1 ml of pre-gel was placed in a petri dish. Mesh squares were then placed on top of the pre-gel, and then pushed down so that the mesh was in suspension. The pre-gel was then placed in a 37° C. non-humidified incubator for 24 hours until it was dry. A picture was taken after ~2 hours of incubation, where it had gelled with the mesh inside, as seen in results.

Lyophilization: approximately 1 ml of pre-gel was placed in each of two petri dishes. The mesh squares were then put in suspension in the pre-gels, as in the air drying method and frozen at −20° C. They were then lyophilized for 24 hours, until dry.

Vacuum Press: 2 ml of pre-gel was placed in each well of the vacuum press mold lined with parafilm. The mesh squares were than placed in suspension and allowed to gel at 37° C. in a non-humidified incubator for 1.5 hours, as seen in results. Cheesecloth was then placed over it, as well as a metal plate and layers of cotton, as per the vacuum press procedure. It was then pressed overnight, and removed.

Following the drying procedures, mesh from each method was washed in order to determine how strongly the digest adhered to the mesh. Also included was a digest-free piece of mesh and a pepsin only (ECM free) digest coated as per the air drying procedure. Three different wash treatments were performed for each preparation: 1. No wash; 2. A brief 2 min rinse in PBS; and 3. A 2 min rinse followed by a 15 min wash in PBS. After the washes, each mesh was allowed to air dry the samples were then sputter coated with palladium for SEM. Each sample was then imaged with SEM at 25×, 500×, and 5,000× magnification.

Results and Conclusions

The air-drying method of digest coating provided the strongest bulk adherence of digest to the BARD™ mesh. Even after 2 short washes, there was good adherence with only a few areas lacking coverage (mostly in gaps of mesh). The lyophilized mesh showed very significant losses after washes, probably due to the low density of the digest around the mesh. The PBS was able to quickly saturate and dissolve the mesh. The vacuum pressed mesh showed low adherence even before washes. This was probably due to the vacuum press procedure where much of the mesh adhered to the cloth used to remove water. The simplest method is also the most effective; as the digest dries, it is laminated onto the mesh. BARD™ polypropylene mesh pieces were coated with B2 dermal ECM and UBM for comparison.

Method 28 pieces of BARD™ mesh were cut into 0.8 mm×0.8 mm squares with a handle to determine sidedness. 5 ml of UBM and B2 pre-gel solutions were prepared having the following components: 4 ml of 10 mg/ml ECM pepsin digest; 0.4 ml of 0.1 N NaOH; 0.44 ml of 10×PBS; and 0.16 ml of 1×PBS. Mesh pieces were arranged in the lids of 50 mm tissue culture dishes so that there is no mesh overlap, and 5 ml of digest added per dish lid (each with 14 pieces of mesh). The mesh pieces were pushed down into suspension using forceps, and the dish lids were placed in 37° C. non-humidified incubator overnight. The mesh pieces were then cut out from the dried digest and sterilized with gamma rad.

Results and Conclusions

Both dermal and UBM digests effectively coated the meshes using this method. Coating appears even over most mesh pieces and both sides; though the bottom face was flat with ECM digest whereas the top was contoured.

Example 11

Methods

AVITENE™ flour was obtained from BARD-Davol. 50 ml of 10 mg/ml AVITENE™ solutions were prepared via two methods.

Pepsin solubilized: 50 ml 0.01 M HCl prepared and 50 mg of porcine pepsin was dissolved in the HCl solution. 500 mg AVITENE™ added and kept on a stir plate at high stir rate for 48 hours Acid solubilized: 50 ml 0.01 M HCl prepared and 500 mg of AVITENE™ added and kept on a stir plate at high stir rate for 48 hours.

After 48 hours, aliquots were taken of each kept in refrigerator at 4° C. 2 ml of each digest was used immediately to test gel formation by adding: 2 ml digest (pepsin or acid); 0.22 ml of 10×PBS; 0.2 ml of 0.1 M NaOH; and 0.08 ml of 1×PBS. Mixed components (1 ml/ring) were added to the center of seeding rings in 6-well plate and 0.5 ml of leftover solution was mixed and added to one ring. Rings and plate were placed in non-humidified incubator for 2 hours at 37° C. and rings were removed to determine gel formation.

Results

After 24 hours, the pepsin method had clarified the AVITENE™ solution, with a slight yellow hue. The acid solution was opaque with small visible particulate in the mixture even after 48 hours at high stir. The acid digest particulate partially aggregated in center of the ring, but broke with plate agitation.

Conclusions

AVITENE™ cannot be formed into a hydrogel using the ECM digestion protocol. Pepsin seems to completely digest all protein. The acid treatment appears to solubilize some of the AVITENE™. The proprietary AVITENE™ processing method or sterilization may damage collagen and prevent gelation.

Example 12—Evaluation of Methods of Coating Polypropylene Meshes with Dermal ECM and AVITENE™

Methods

Dermal ECM was utilized (10 mg/ml pepsin digest spun hard for 48 hours at RT). All meshes were placed in square cryomolds that hold approximately 1 ml of solution. All lyophilization conducted in a small lyophilizer (Labconco FreeZone 1 base with shelf manifold; Labconco, Kansas City, Mo.). Mesh coatings were manufactured using three different methods.

Lyophilized D-ECM hydrogel coated mesh—1 cm×1 cm meshes were embedded in hydrogels. The concentration of digest was 4 mg/ml and 8 mg/ml. Dishes were incubated for 1 hour at 37° C. at neutral pH to induce gelation. A 4 mg/ml and an 8 mg/ml gel-covered mesh were frozen by placing the meshes in a −20° C. freezer overnight. Frozen gel-embedded meshes were lyophilized with pieces of dry ice to keep frozen.

Lyophilized D-ECM hydrogel coated mesh—1 cm×1 cm meshes were embedded in hydrogels. The concentration of digest was 4 mg/ml and 8 mg/ml. Dishes were incubated for 1 hour at 37° C. at neutral pH to induce gelation. A 4 mg/ml and an 8 mg/ml gel-covered mesh were frozen by placing the meshes in a −20° C. freezer overnight. A 4 mg/ml and an 8 mg/ml gel-covered mesh were frozen by floating over liquid $N_2$ for 15 min and placing the meshes on dry ice for 30 min, then placing the meshes in a −80° C. freezer overnight. Frozen gel-embedded meshes were lyophilized with pieces of dry ice to keep frozen.

Lyophilized AVITENE™ slurry coated mesh—1 cm×1 cm meshes were placed in two different AVITENE™ slurries following acid dispersion at 10 mg/ml: AVITENE™ in Type I water at 10 mg/ml concentrations; and AVITENE™ in Type I water at 40 mg/ml concentrations. AVITENE™ (C.R. BARD-Davol, Providence, R.I.) is a Type I collagen product, which contrasts with intact ECM as utilized in the present devices and methods. In both slurries the meshes were shaken vigorously every 30 min for 2 hours at RT. Slurry-embedded meshes were then frozen as described above for the dermal ECM meshes: One of each AVITENE™ group was frozen by placing in −20° C. freezer overnight and one of each group was frozen by floating the meshes over liquid $N_2$ for 15 min and placing the meshes on dry ice for 30 min, then placing the meshes in −80° C. freezer overnight. Frozen slurry-embedded meshes were lyophilized with pieces of dry ice to keep frozen.

Thermal induced phase separation AVITENE™ coated mesh—AVITENE™ was added to different EtOH/$H_2O$ solutions at 40 mg/ml in the following ratios: 20:80 EtOH:$H_2O$; 35:65 EtOH:$H_2O$; and 50:50 EtOH:$H_2O$. Meshes were placed in a 37° C. water bath and shaken vigorously every hour for about 4 hours. 1×1 cm meshes were then placed in these AVITENE™-ethanol slurries and frozen. Two of each group of mesh were frozen by floating over liquid $N_2$ for 15 min and placing on dry ice for 30 min, then placing the meshes in a −80° C. freezer overnight. Frozen slurry-embedded meshes were lyophilized with pieces of dry ice to keep frozen.

Results

Acid digests from the refrigerator were almost completely in solution/suspension, there was no precipitate, and the digests were mostly homogeneous. All other dispersions were "chunky", though they were not spun for two days: ethanol solutions only in water bath at 37° C. for 4 hours, ones in water only at room temperature for 2 hours (and was maybe slightly chunkier than ethanol). $H_2O$ ones sedimented if left alone for 15 min. Acid dispersions did not sediment. Ethanol solutions did not appear to sediment. The ethanol solutions boiled rapidly when lyophilization began, which was most rapid for the higher ethanol ratios. The 20:80 EtOH/water solution maintained structure, though 'popped out' of the mold. The ECM gels maintained structure during the lyophilization. AVITENE™ was ineffective for forming a gel around the mesh; when washed in PBS, AVITENE™ was sloughed away.

Example 13

Method

D-ECM and AVITENE™ were prepared as described above. All meshes were placed in square cryomolds that hold approximately 1 ml of solution. The dispersion solutions were prepared as follows.

Air dried AVITENE™ slurry coated mesh—1 cm×1 cm BARD™ meshes were placed in AVITENE™ slurries as follows: 1. Acid dispersion at 10 mg/ml; 2. AVITENE™ in Type I water at 10 mg/ml concentrations; and 3. AVITENE™ in Type I water at 40 mg/ml concentrations. Slurry-embedded meshes were then placed in non-humidified incubator at 37° C. overnight, very loosely covered with foil.

EtOH/$H_2O$ AVITENE™ slurry air dried coated mesh—AVITENE™ added to different EtOH/$H_2O$ solutions at 40 mg/ml in the following ratios: 20:80 EtOH:$H_2O$; 35:65 EtOH:$H_2O$; and 50:50 EtOH:$H_2O$. 1 cm×1 cm BARD™ meshes were placed in AVITENE™ ethanol slurries, and ethanol slurry-embedded meshes were then placed in non-humidified incubator at 37° C. overnight very loosely covered with foil.

Results

All of the samples completely dried. All of the slurry samples at 40 mg/ml completely covered the mesh fibers and spaces between fibers. The 10 mg/ml slurry was a thinner coating that didn't' completely fill all holes. The acid solution was the thinnest coating, with many spaces between fibers.

Example 14

Evaluation of methods of coating polypropylene meshes with dermal ECM and AVITENE™ in a small and large lyophilizer.

Methods

Dermal ECM and AVITENE™ as described above were utilized. BARD™ meshes were utilized and placed in square cryomolds that hold approximately 1 ml of solution. The following articles were tested.

D-ECM hydrogel coated mesh (−20° C.)—1 cm×1 cm meshes were embedded in hydrogels. The concentration of digest was 4 mg/ml and 8 mg/ml. Dishes were incubated for 1 hour at 37° C. at neutral pH to induce gelation. A 4 mg/ml and an 8 mg/ml gel-covered mesh were frozen by placing the meshes in a −20° C. freezer overnight.

D-ECM hydrogel coated mesh (−80° C.)—1 cm×1 cm meshes were embedded in hydrogels. The concentration of digest was 4 mg/ml and 8 mg/ml. Dishes were incubated for 1 hour at 37° C. at neutral pH to induce gelation. A 4 mg/ml and an 8 mg/ml gel-covered mesh were frozen by placing the meshes in a −20° C. freezer overnight. A 4 mg/ml and an 8 mg/ml gel-covered mesh were frozen by floating over liquid $N_2$ for 15 min and placing the meshes on dry ice for 30 min, then placing the meshes in a −80° C. freezer overnight.

AVITENE™ slurry coated mesh—1 cm×1 cm meshes were placed in two different AVITENE™ slurries following acid dispersion at 10 mg/ml: AVITENE™ in Type I water at 10 mg/ml concentrations; and AVITENE™ in Type I water at 40 mg/ml concentrations. In both slurries the meshes were shaken vigorously every 30 min for two hours at room temperature. Slurry-embedded meshes were then frozen as described above for the dermal ECM meshes: Meshes were frozen by placing in −20° C. freezer overnight.

Frozen gel-embedded meshes were lyophilized in a large lyophilizer (Dura-Top/Dura-Dry MP combination FTS Systems, SP Industries/SP Scientific, Warminster, Pa.), which had shelves cooled to −30° C., or a small lyophilizer (Labconco FreeZone 1 base with shelf manifold; Labconco, Kansas City, Mo.), in which the shelves were not cooled. Only the samples frozen at −20° C. (D-ECM and AVITENE™) were lyophilized in this device.

Results

The −20° C. frozen samples underwent a brief thaw/boil/freeze immediately after the start of lyophilization, which was not seen for the −80° C. samples. Soon after this thaw/boil/freeze phase, samples froze and lyophilized normally. This was not observed for the larger lyophilizer. There was a bubble on the surface of the 8 mg/ml D-ECM gel that was not the result of drying.

Conclusions

BARD™ polypropylene mesh was successfully coated with D-ECM hydrogels and AVITENE™ dispersions and dried via lyophilization. The smaller lyophilizer does not have cooled shelves, so as the vacuum builds there may be some boiling, which may disrupt structure. SEM structural analysis before and after PBS washes showed that AVITENE™ was not effectively gelled on the meshes, and was sloughed off.

Example 15—Determination of Differences in D-ECM Gel and AVITENE™ Coated Mesh after PBS Washes Methods Coated mesh materials and devices are as produced as described above. Each device was divided in half, so that half could be used for SEM pre-wash and half could be used for washing.

Each device was placed in a 12-well plate. AVITENE™ UltraFoam and UltraWrap (C.R. BARD-Davol (Providence, R.I.)) were placed in a 6-well plate). 3 ml of PBS was pre-heated to 37° C. and added to each well with a transfer pipette, and incubated for 15 min. Devices were imaged and the PBS was removed.

3 ml of PBS was pre-heated to 37° C. and added to each well with a transfer pipette, and incubated for 15 min. Devices were imaged and the PBS was removed.

Devices were then dried using the same methodology in which they were originally dried, except that all were subsequently lyophilized in the small lyophilizer (without cooled shelves):

Air dried: PBS was removed and the meshes were placed in a non-humidified incubator for 24 hours.

Liquid Nitrogen ($N_2$): Samples were placed in a 12 well plate floating on liquid nitrogen then placed in a −80° C. freezer overnight. The plate was then placed in the small lyophilizer on shelf cooled with dry ice.

−20° C.: Samples were frozen with a small amount of PBS in wells in a −20° C. freezer then placed on a non-chilled shelf of the small lyophilizer.

Results

All coatings mostly adhered to the mesh devices. D-ECM-coated meshes changed shape on hydration; an opaque white potion would shrink and conform to the mesh. The outermost coating was clear. All of the $N_2$ frozen coated meshes were removed for refreezing; all of the coatings completely adhered except for the EtOH solvent-coated samples, where excess coating around the edge of the mesh remained. The coating on the mesh itself adhered, but was very loose and appeared as though it would fall off on handling. The higher the concentration of EtOH, the looser the coating. The UltraFoam and UltraWrap shrunk a little on hydration. Air-dried samples became more pliable after hydration (were previously very rigid when dry). All re-dried samples appeared similar to the pre-hydration devices.

Conclusion

All coatings effectively adhered to the mesh devices and did not simply dissolve away, though there was loss of excess coating for lyophilized EtOH samples only. The highest concentrations of AVITENE™ (40 mg/ml) were densest and most opaque, though the 10 mg/ml acid AVITENE™ coating was similar. It was difficult to assess differences between the D-ECM samples, except that the higher concentration of 8 mg/ml appeared more stable and adherent than 4 mg/ml. The D-ECM samples were also made in PBS, so the salt concentration left after drying may have affected rehydration (AVITENE™ was in water or dilute acid); the effect of salt concentration or washing the salt away after gelation may also be tested.

Example 16—Polypropylene Surgical Mesh Coated with ECM Mitigates the Host Foreign Body Response Methods Overview of Experimental Design and Test Articles BARD™ Mesh, a heavy-weight polypropylene surgical mesh, was coated with a hydrogel composed of dermal ECM. The mechanical properties and host soft tissue response following implantation in a rat partial abdominal wall defect were compared to those of a non-coated heavy-weight polypropylene surgical mesh and two light-weight surgical mesh devices. The light-weight meshes used in this study were Ethicon ULTRAPRO™, a polypropylene/monocryl composite mesh, and BARD™ Soft Mesh, a polypropylene mesh.

Dermal ECM Preparation and Polypropylene Mesh Coating

Dermal ECM was prepared as previously described from full thickness skin harvested from market weight (~110 kg) pigs. In brief, subcutaneous fat and epidermis were removed by mechanical delamination followed by treatment with 0.25% trypsin (Thermo Fisher Scientific, Waltham, Mass.) for 6 hours, 70% ethanol for 10 hours, 3% H2O2 for 15 min, 1% Triton X-100 (Sigma-Aldrich, St. Louis, Mo.) in 0.26% EDTA/0.69% Tris for 6 hours with a solution change for an additional 16 hours, 0.1% peracetic acid/4% ethanol (Rochester Midland, Rochester, N.Y.) for 2 hours. Water washes were performed between each chemical change with alternating water and phosphate buffered saline (PBS) washes following the final step. All chemical exposures were conducted under agitation on an orbital shaker at 300 rpm. Dermal ECM was then frozen, lyophilized, and comminuted into a 40 mesh powder. The dermal ECM powder was solubilized as previously described by partial enzymatic digestion in a 1 mg/mL pepsin (Sigma-Aldrich) solution in 0.01 N HCl for 48 h at a concentration of 10 mg ECM/mL solution (dry wt/vol). Solubilized dermal ECM was brought to physiologic pH and salt concentration while on ice by adding ⅑ the digest volume of 10×PBS, ¹⁄₁₀ the volume of 0.1 N NaOH, and then further diluted to 8 mg ECM/ml with 1×PBS. The neutralized dermal ECM digest was immediately added to a square plastic dish and 2 cm×3 cm pieces of pre-cut polypropylene mesh were suspended in the solution. The viscosity of the digest was sufficient for the mesh to remain in suspension until gelation had occurred. The neutralized digest and polypropylene mesh were then placed in a non-humidified incubator at 37° C. for approximately 30-45 min until the dermal ECM digest formed a hydrogel (~4.5 mm total thickness) around the mesh (~0.66 mm mesh thickness) and between the fibers of the polypropylene mesh. The dermal ECM hydrogel embedded mesh was then air dried at 37° C. overnight to complete the coating process (~0.68 mm ECM-coated mesh thickness). Stability of the ECM coating was determined by placing ECM coated meshes in PBS at 37° C. for 3×15 min washes followed by immersion for 24 h in PBS and subsequent examination for evidence of delamination of the ECM from the polypropylene. All devices used for in vivo implantation were terminally sterilized with ethylene oxide.

Scanning Electron Microscopy

Mesh fiber geometry and surface characteristics were evaluated with scanning electron microscopy (SEM). The ECM coated mesh was hydrated in PBS and fixed in 2.5% glutaraldehyde for scanning electron microscopy. ECM coated meshes were then washed with PBS, dehydrated in a graded series of ethanol, and dried in hexamethyldisilazane (Thermo-Fisher Scientific). The non-coated polypropylene mesh materials did not require fixation or dehydration. The ECM coated mesh, uncoated BARD™, ULTRAPRO™, and BARD™ Soft, meshes were mounted onto aluminum stubs and then sputter coated (Sputter Coater 108 Auto, Cressington Scientific Instruments, Watford, UK) with a 3.5 nm thick gold/palladium alloy. The meshes were then imaged with a scanning electron microscope (JEOL JSM6330f, JEOL, Peabody, Mass.) at a 3.0 kV accelerating voltage.

Mesh In Vivo Implantation

Figure 2:
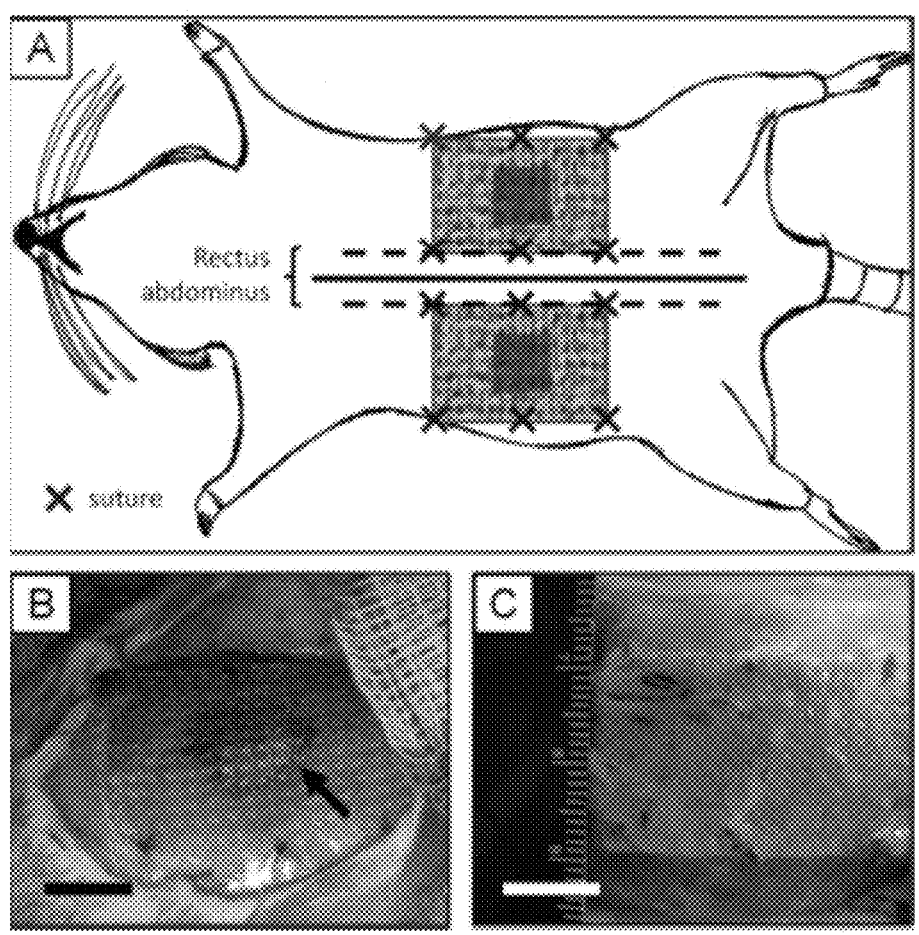
FIG. 2 shows A. a schematic of the anatomy of a rat, including the rectus abdominus and a surgical model of mesh implantation, Mesh devices were fixed to the abdominal using six single interrupted sutures (dark "X" s) along the edge of the mesh; B. mesh during implantation surgery over a partial thickness defect (visible through the mesh pores, arrow) and fixed to the abdominal wall with six sutures around the edge of the mesh; C. mesh in situ 35 days after implantation (scale bar represents 1 cm).

Mesh materials were used to repair an in vivo model of abdominal wall injury to evaluate mesh remodeling response and biomechanical properties. Female Sprague-Dawley rats (250-300 g) were anesthetized with 2-3% isofluorane and ventral midline skin incision was made. A 1 cm×1 cm partial thickness paramedian defect was created by removing the internal and external oblique muscles and leaving the transversalis fascia and peritoneum intact. The defects were either left untreated as controls or were overlaid with 2 cm×3 cm mesh test articles centered over the defect area, with the 3 cm edge of the mesh parallel to midline along the edge of the rectus abdominus as shown in FIG. 2, panel A and B. Mesh placement was consistent by aligning the stiffer axis perpendicular to the midline (i.e., along the abdominal wall circumferential direction), and the more compliant axis parallel to the midline (i.e., along the rostral to caudal, or longitudinal direction). Each mesh possessed anisotropic mechanical behavior, in which the mesh was stiffer in one direction compared to the perpendicular direction under uniaxial loads (as shown in the "Results" section). Mesh fixation to the abdominal wall was achieved using single interrupted 4-0 Prolene sutures (Ethicon) at the 4 corners of the mesh with 2 additional sutures at the midpoint of the 3 cm edge of the mesh. Each rat was implanted with 2 randomly assigned mesh devices, one per side. The skin incision was then closed with 4-0 Vicryl (Ethicon) suture and the animals were allowed to recover and ambulate normally. Animals were sacrificed after 3, 7, 14, or 35 days of implantation (FIG. 3, panel C), after which time, the mesh and associated muscle tissue was explanted for either histologic (n=4 animals per device and time point) or biomechanical characterization (n=8 animals per device at the 35 day time point).

Quantitative Histologic Analysis and Immunolabeling

A quantitative histomorphometric scoring system was used to evaluate the host response to the implanted mesh materials at each time point as summarized in Table 1 below.

TABLE 1

| Region | Category | Description of Quantitative Analysis |
|---|---|---|
| Mesh fiber/ tissue Interface | Cellularity | Number of cell layers of dense cellular accumulation immediately adjacent to fibers per FOV |
|  | Foreign Body Giant Cells | Number of foreign body giant cells per FOV |
| Tissue Between Mesh Fibers | Cellularity | Number of mononuclear cells per FOV in increments of 50 cells |
|  | Vascularity | Number of blood vessels per FOV |
|  | Collagen Fiber Density and Thickness | Collagen density as % area of collagen per FOV Collagen fiber thickness as color hue (in order of increasing thickness) |

Mesh-tissue explants were immediately fixed with formalin, embedded in paraffin, sectioned (5 μm), mounted onto microscope slides, and stained with hematoxylin and eosin (H&E). A total of 6 high magnification images (400×) were acquired by blinded observers for each H&E stained section; three images of the mesh fiber/tissue interface and three images of the deposited tissue between mesh fibers. The mesh fiber/tissue interface images were positioned at the edge of mesh fiber bundles such that the inflammatory response to the mesh was visible within the field of view. The mesh fiber/tissue interface images were quantified for two criteria: the thickness of the dense cell accumulation at the fiber surface (reported as number of cell layers away from the mesh fiber) and the total number of multinucleate foreign body giant cells surrounding the mesh fiber in each image. The images of the tissue between mesh fibers were acquired at the midpoint between adjacent mesh fiber bundles and were quantified for two criteria; the total number of mononuclear cells per image (rounded to the nearest 50) and the total number of blood vessels (with identifiable lumen and red blood cells).

All quantitative analysis was conducted by three independent blinded observers. The area of collagen fibers as a function of their color hue was quantified from tissue sections stained with picrosirius red and imaged with circularly polarized light microscopy (200× magnification).

The color hue corresponds to relative fiber thickness from thin fibers to increasingly thick fibers. Following a previously published protocol (Rich L et al. Collagen and picrosirius red staining: a polarized light assessment of fibrillar hue and spatial distribution. Braz J Morphol Sci 2005; 22:97-104; Nadkarni S K et al. Measurement of collagen and smooth muscle cell content in atherosclerotic plaques using polarization-sensitive optical coherence tomography. J Am Coll Cardiol 2007; 49: 1474-1481) a custom algorithm was constructed with Matlab software (The Mathworks, Natick, Mass.) that: (1) cropped each image to only connective tissue directly between mesh fibers removing all subcutaneous connective and underlying muscle tissue; (2) transformed each image from the RGB to the HSV color model; (3) separated each color component as a function of hue; (4) applied a threshold to remove noise from an average of a global threshold using Otsu's method (intensity value of 50/256); and (5) expressed the collagen content for each color component as a percentage of the area of each image. The infiltrating cell population both adjacent to and in the space between mesh fibers was characterized for expression of the monocyte/macrophage marker CD68. Tissue sections were de-paraffinized, subjected to epitope retrieval in 10 mM citrate (pH=6) at 95° C. for 20 min, blocked with 1% bovine serum albumin/10% horse serum for 1 h at room temperature, and labeled with a mouse anti-rat CD68 primary antibody (1:100, clone ED1, MCA341R, AbD Serotec, Raleigh, N.C.) diluted in 1% bovine serum albumin overnight at 4° C. Endogenous peroxidase activity was quenched with 0.3% (v/v) hydrogen peroxide in distilled water for 15 min at room temperature, and then incubated in a HRP conjugated goat anti-mouse secondary antibody (1:200, Vector, Burlingame, Calif.) diluted in 1% bovine serum albumin for 1 h at room temperature. Staining developed with the addition of a diaminobenzadine substrate (DAB peroxidase substrate kit, SK4100, Vector) for approximately 6 min followed by counterstaining with hematoxylin, dehydration, and coverslipping.

Ex Vivo Mesh Biaxial Mechanical Properties

The passive biaxial mechanical properties were characterized for the various mesh materials prior to implantation (n=3), and after 35 days for the mesh-tissue explants, unrepaired defect controls (n=8), and the uninjured native abdominal wall (n=5). Immediately following explanation, samples were placed in Ringer's solution supplemented with 0.5 mM verapamil (Sigma) chilled on ice for at least 1 hour prior to testing. The mesh-tissue explants were trimmed to 1.5 cm×1.5 cm centered over the partial thickness defect region where tissue thickness was measured with a caliper for use in biaxial testing. Biaxial mechanical testing applies a load to a sample along two perpendicular axes simultaneously compared to a uniaxial test were only one axis is loaded. A detailed description of the testing device and methods used for planar biaxial testing has been previously reported (Billiar K L et al. Biaxial mechanical properties of the natural and glutaraldehyde treated aortic valve cusp—Part I: Experimental results. J Biomech Eng 2000; 122: 23-30). Samples were affixed to 250 g load cells (Model 31, Honeywell, Columbus, Ohio) with two loops of suture attached to each side with four hooks, and deformation was measured from a four marker array centered on the ventral surface after the removal of excess loose connective tissue.

Samples were tested in a Ringers saline solution at room temperature under an equibiaxial stress protocol from a 0.5 g tare load to 85 kPa after 10 cycles of preconditioning with a cycle time of 30 s. All data were referenced to the post-preconditioned free-float state. The maximum strain for each sample was then defined as the strain at the maximum tested stress of 85 kPa. Each mesh device was tested prior to implantation using a modified biaxial protocol. The edges of the porous mesh samples were heat sealed with polypropylene strips to create a uniform edge for hook attachment. The samples were then formed into a cross-hair shape with each heat sealed edge decoupled from neighboring edges to minimize the boundary condition effect. The center of each sample measured approximately 1.5 cm×1.5 cm, with an additional 0.25 cm heat sealed edge where hooks were attached. Adding conventional strain markers, as was done for the tissue samples, would have introduced a non-trivial constraint on the mesh fiber deformation and kinematics, and therefore, strain was defined as total motor displacement over initial sample length. The initial reference state was defined where no slack remained in the suture line. This slack, which would contribute to a false strain measurement, was removed with a 2.5 g tare load. The preimplant mesh devices do not have a uniform thickness so the load was normalized by sample width to calculate tension, rather than thickness used to calculate stress. Samples were tested under a biaxial and uniaxial load (n=3) after preconditioning to a maximum tension of 100 N/m, which was approximately the tension applied to the mesh-tissue explants using an 85 kPa stress protocol. Maximum strain for the pre-implant mesh devices was defined as the strain at this maximum tension.

Statistical Analysis

The histologic response to mesh materials was compared within time points using a one-way analysis of variance (ANOVA) and Tukey post-hoc analysis to determine significance ($p<0.05$) with SPSS software (IBM SPSS Statistics, IBM, Armonk, N.Y.). Each histologic remodeling criterion was analyzed independently from the mean values of three blinded observers, and this mean value for each image was used for statistical analysis. The biaxial mechanics stress versus strain and tension versus strain curves were averaged after a three-point linear interpolation at representative stress or tension values with MATLAB software (Mathworks, Natick, Mass.). A one-way ANOVA and post-hoc Tukey analysis was also used to (significance as $p<0.05$) to compare maximum strain values All histologic scoring and mechanical analysis values are reported as the mean±standard error of the mean (SEM).

Results

Mesh Macroscopic Appearance and Scanning Electron Microscopy

Figure 3:
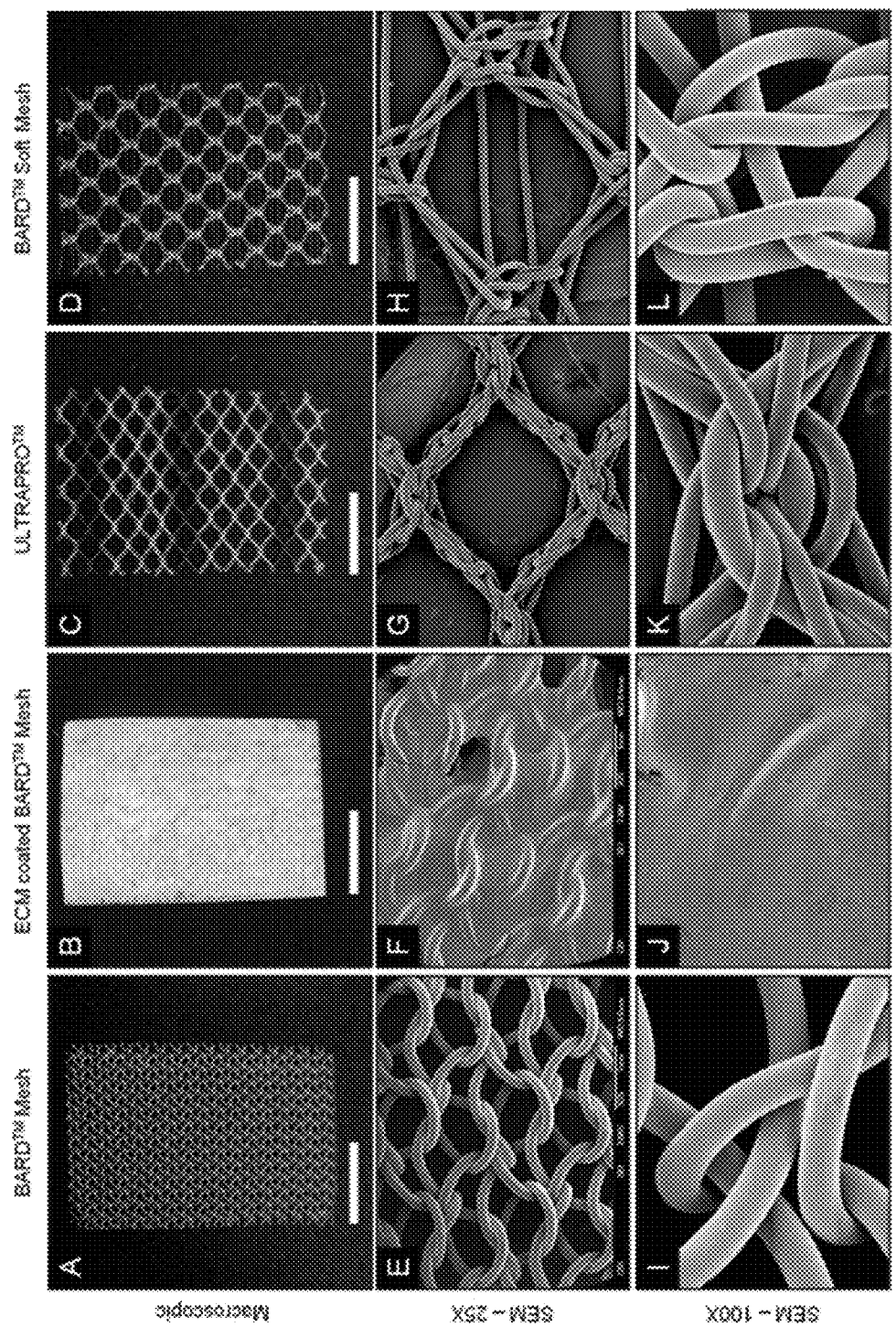
FIG. 3 shows macroscopic (top row) appearance and SEM (middle and bottom rows) images of mesh devices, including BARD™ Mesh (A, E, I), ECM-coated BARD™ Mesh (B, F, J), ULTRAPRO™ (C, G, K), and BARD™ Soft Mesh (D, H, L). Scale bars represent 1 cm.

The heavy-weight BARD™ Mesh possessed a greater fiber density per area (corresponding to smaller pore size) than both light-weight meshes, ULTRAPRO™ and the BARD™ Soft Mesh, as shown both macroscopically (FIG. 3, panels A-D) and with scanning electron microscopy (FIG. 3, panels E-L). The ECM coating completely covered and adhered to the BARD™ Mesh fibers and knots. The ECM coating was also continuous between mesh fibers and across the pores as a thin coating layer, which remained adherent to the mesh after a 24 h wash in PBS at 37° C. (FIG. 3, panels B, F, and J). The BARD™ Soft Mesh had the largest pore size, which was reinforced by two small fibers running in parallel across each pore (FIG. 3, panel G), and along with ULTRAPRO™ (FIG. 3, panels K and L) had larger knots than BARD™ Mesh (FIG. 3, panel I).

Mesh In Vivo Implantation and Quantitative Histologic Analysis

Figure 4A:
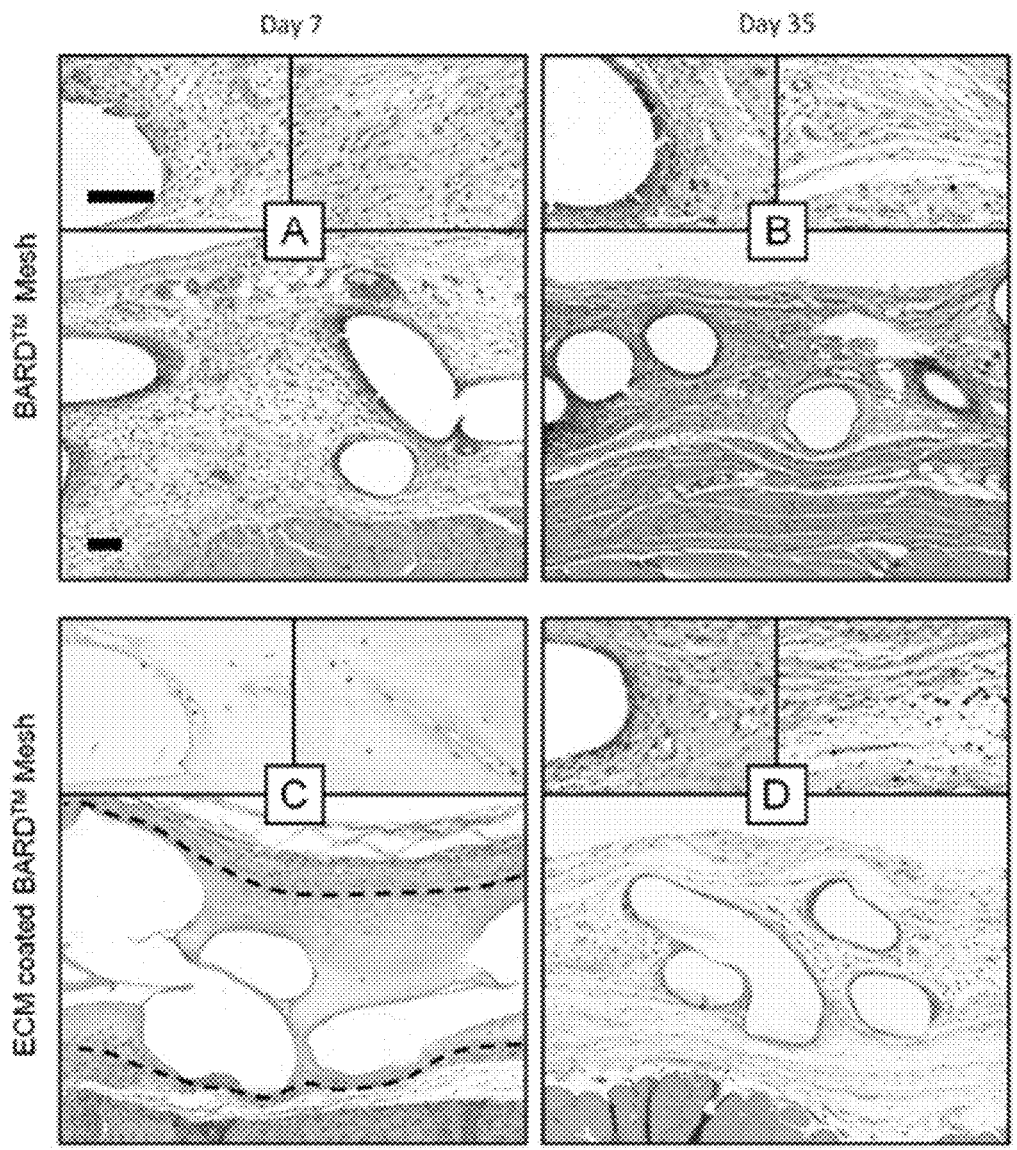
FIG. 4A-4B shows histologic appearance of mesh devices 7 (left column) and 35 (right column) days after implantation. Shown are H&E stained histologic cross-sections of BARD™ Mesh (A, B), ECM-coated BARD™ Mesh (C, D), ULTRAPRO™ (E, F), and BARD™ Soft Mesh (G, H) at 100×. The upper image of each panel is a 400× magnification immunolabeled for CD68 in the areas adjacent to mesh fibers (upper left panel) and between mesh fibers (upper right panel). The dotted line in panel C encloses the ECM coating surrounding the mesh fibers. Scale bars represent 100 µm.
Figure 4B:
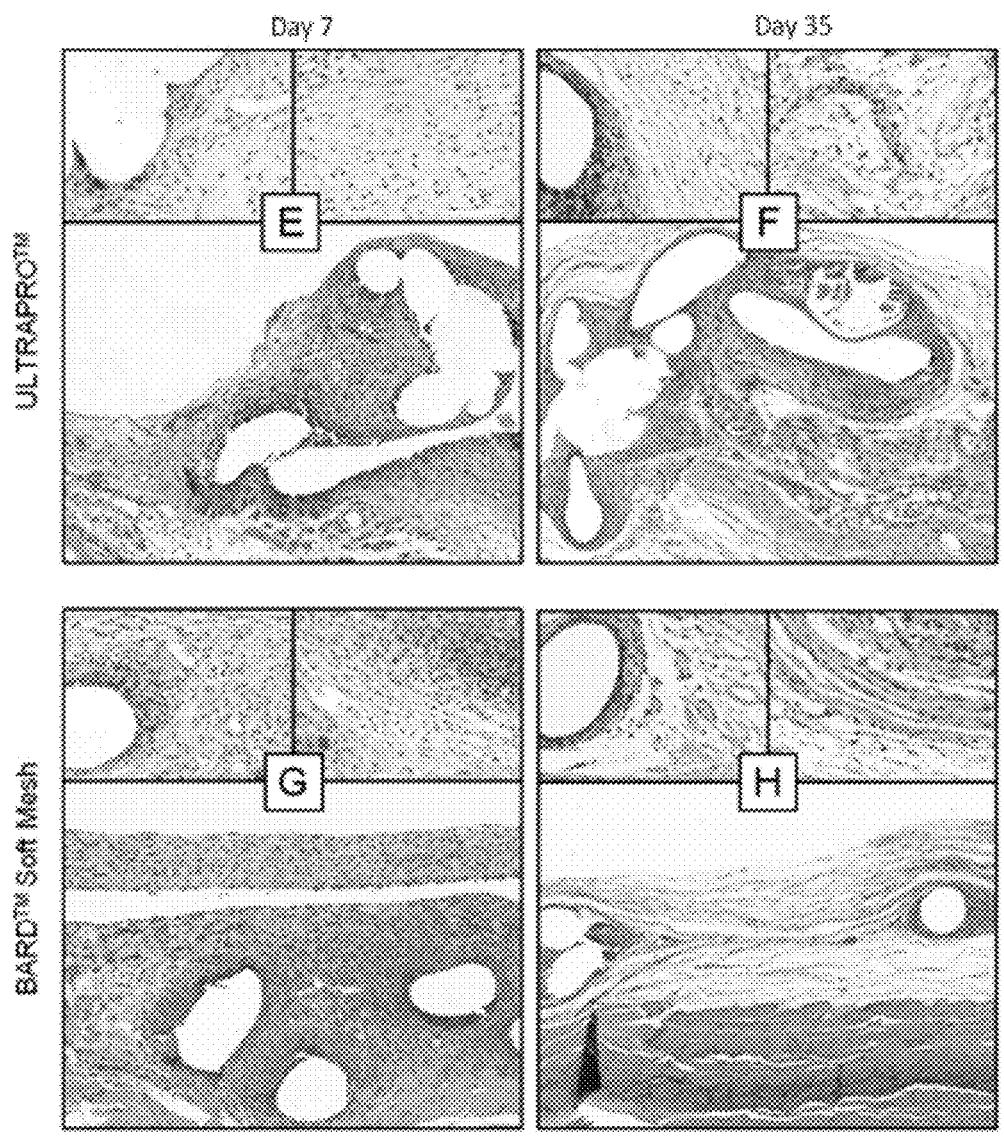
Figure 5A:
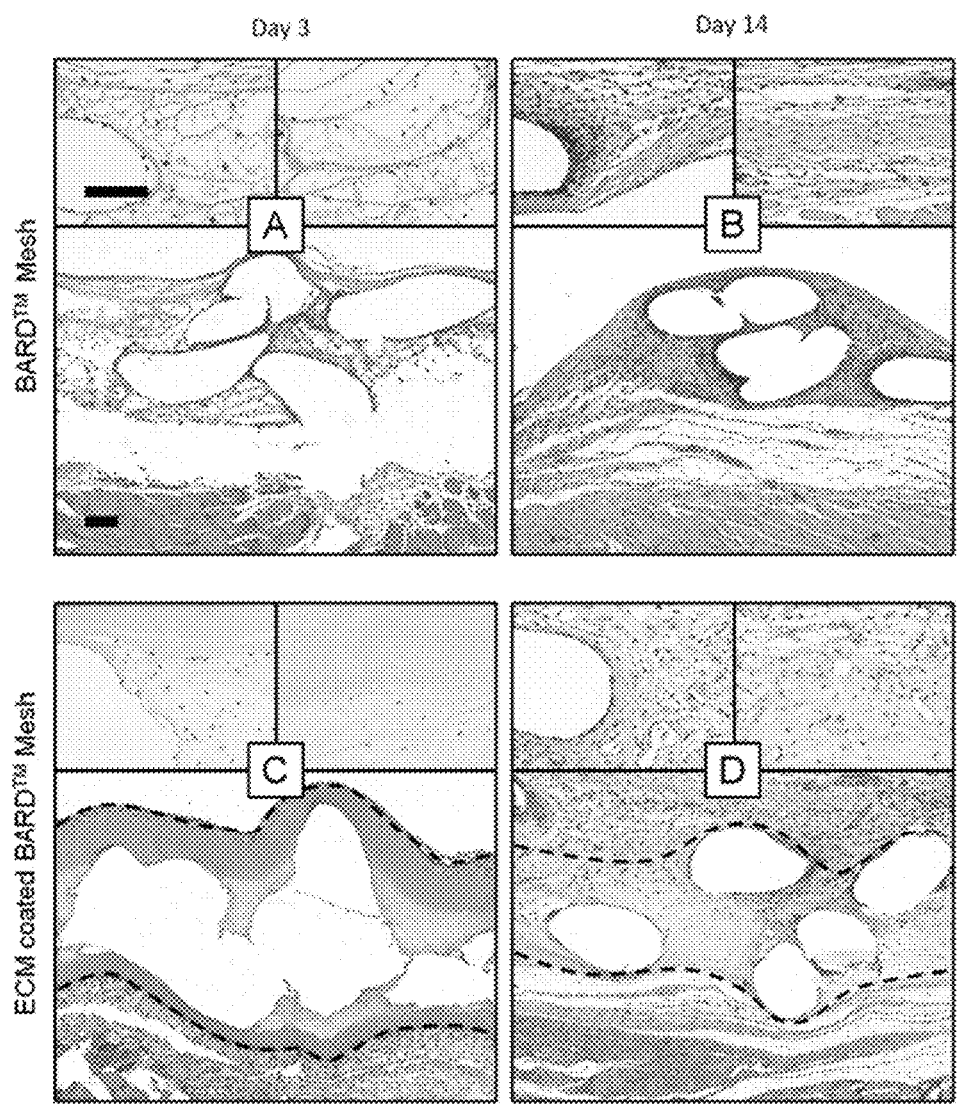
FIG. 5A-5B shows histologic appearance of mesh devices after 3 (left column) and 14 (right column) days of in vivo implantation. Representative H&E stained histologic cross sections of each mesh/time point (BARD™ Mesh (A, B), ECM-coated BARD™ Mesh (C, D), ULTRAPRO™ (E, F), and BARD™ Soft Mesh (G, H)) were imaged at 100× magnification (bottom of each figure panel). Two 400× magnification images immunolabeled for the macrophage marker CD68 (upper panels) were focused on the area adjacent to mesh fibers (top left of each panel) and the area between mesh fibers (top right of each panel). Dotted line in C and D encloses the ECM coating surrounding the mesh fibers. Scale bars represents 100 µm.
Figure 5B:
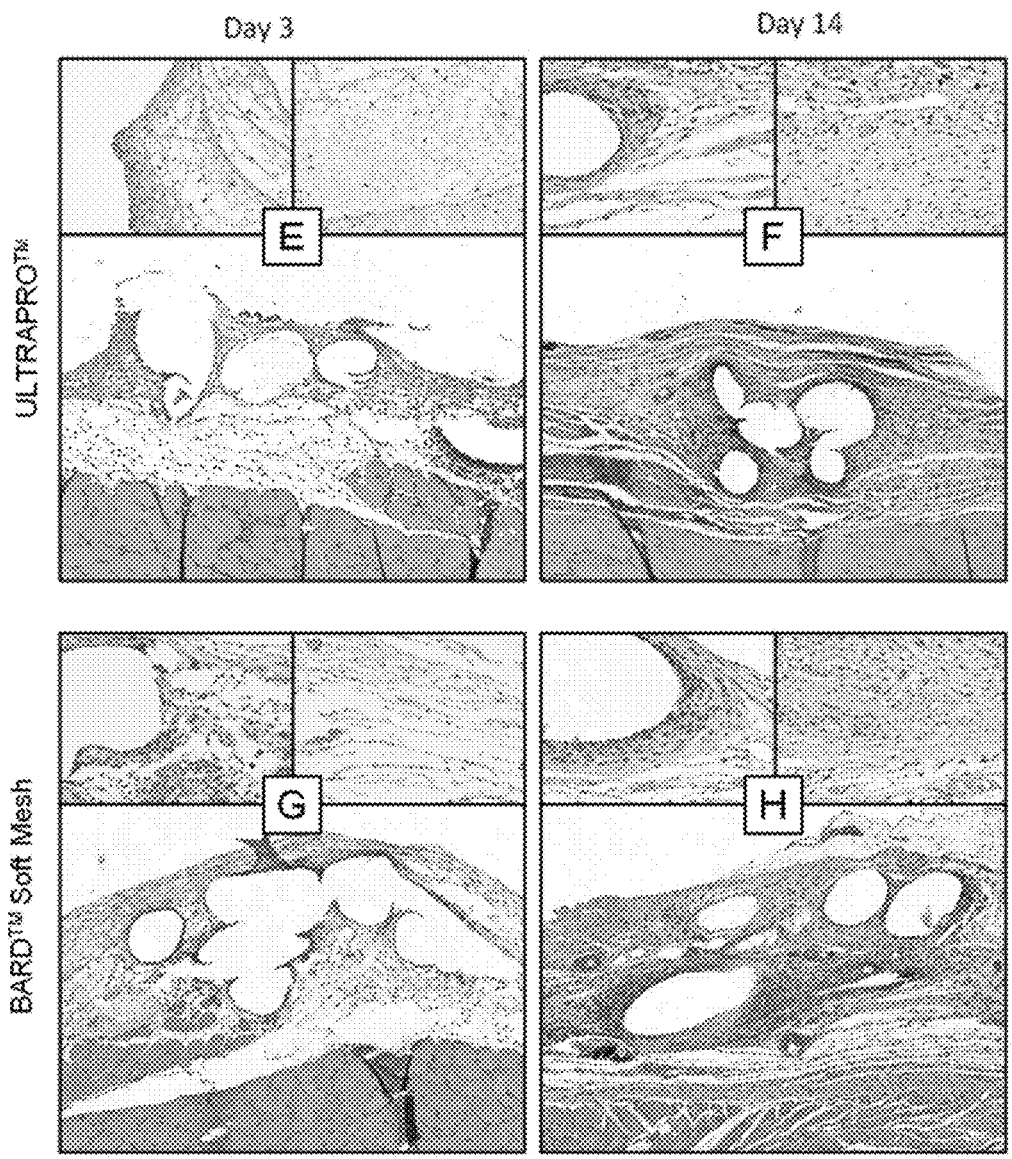

The mesh materials were implanted over a partial thickness abdominal wall defect in the rat for 3, 7, 14, and 35 days. There was macroscopic evidence of new host tissue deposition over the implanted mesh fibers as early as 3 days post-implantation, and all mesh materials were fully incorporated into the body wall by 35 days. The white ECM coating was clearly visible after 3 days, but became less defined over time, eventually becoming indistinguishable from the appearance of the non-coated mesh materials. There was no macroscopic evidence of mesh contracture at any of the time points evaluated. The histologic response to each mesh material was evaluated by blinded observers from H&E stained sections focusing upon the mesh fiber/tissue interface and the new tissue deposition between mesh fibers (FIGS. 4-5).

Figure 6A:
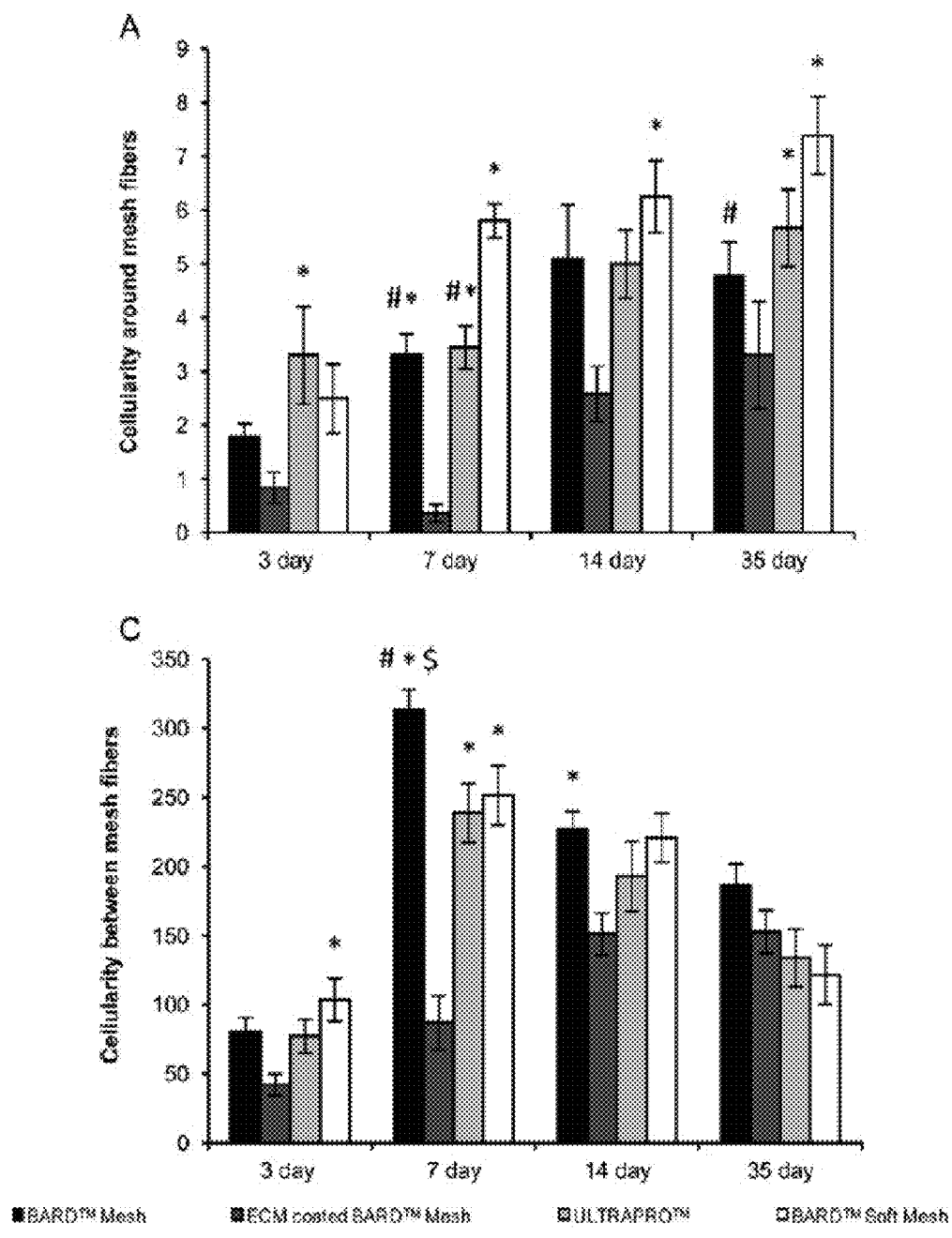
FIG. 6A-6B shows histomorphic analysis of the histologic inflammatory response to mesh fibers and tissue remodeling in the area between mesh fibers from H&E stained histologic cross sections after 3, 7, 14, and 35 days post-implantation: A. The mesh fiber cellularity; and B. number of foreign body giant cells for each device were counted to characterize the inflammatory response to mesh fibers. Tissue remodeling between mesh fibers was analyzed as: C. number of mononuclear cells; and D. number of blood vessels. Significant differences ($p<0.05$) between devices within each time point are denoted: (*) as different from the ECM coated BARD™ Mesh, ($) as different from ULTRAPRO™, and (#) as different from BARD™ Soft Mesh.
Figure 6B:
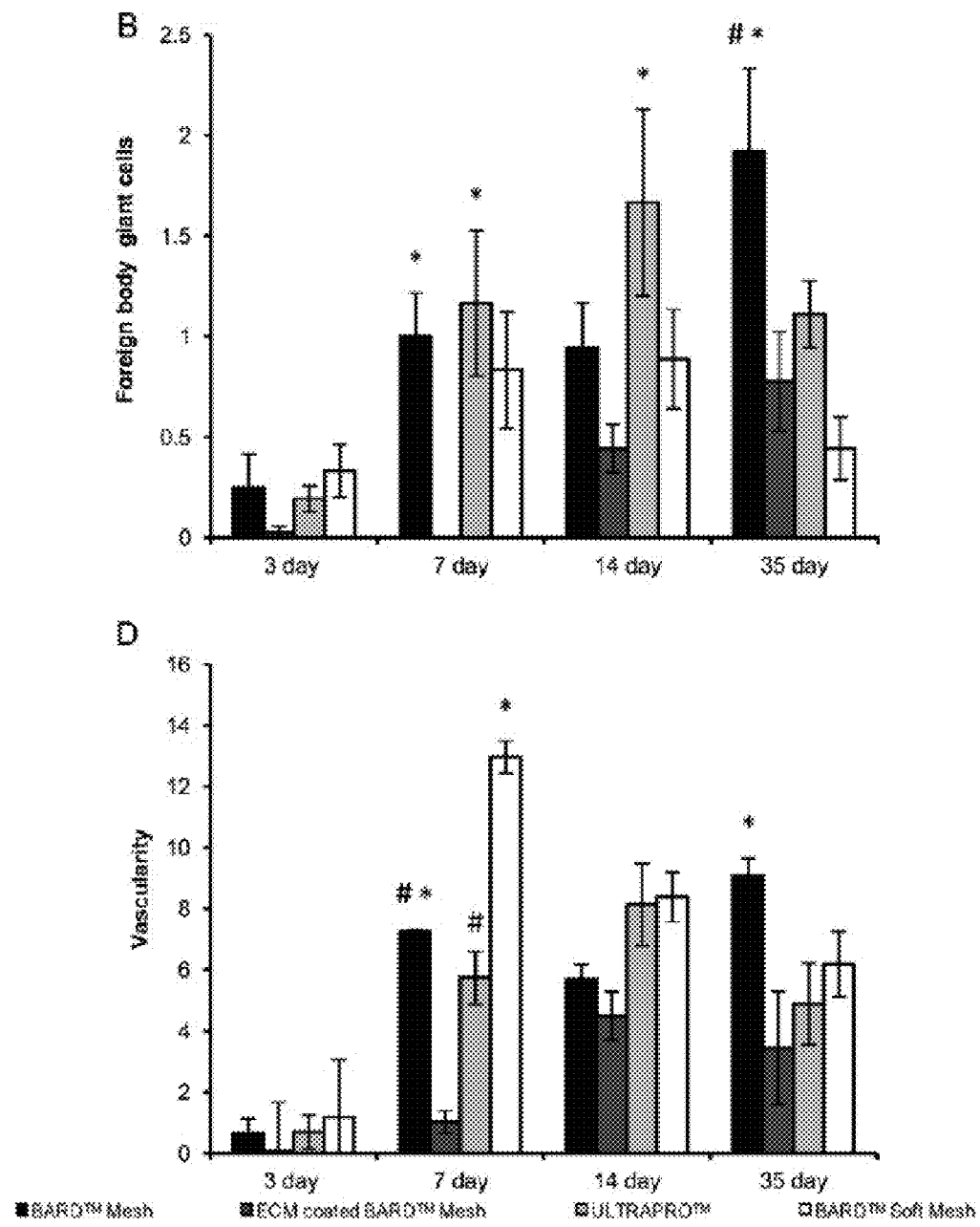
Figure 7:
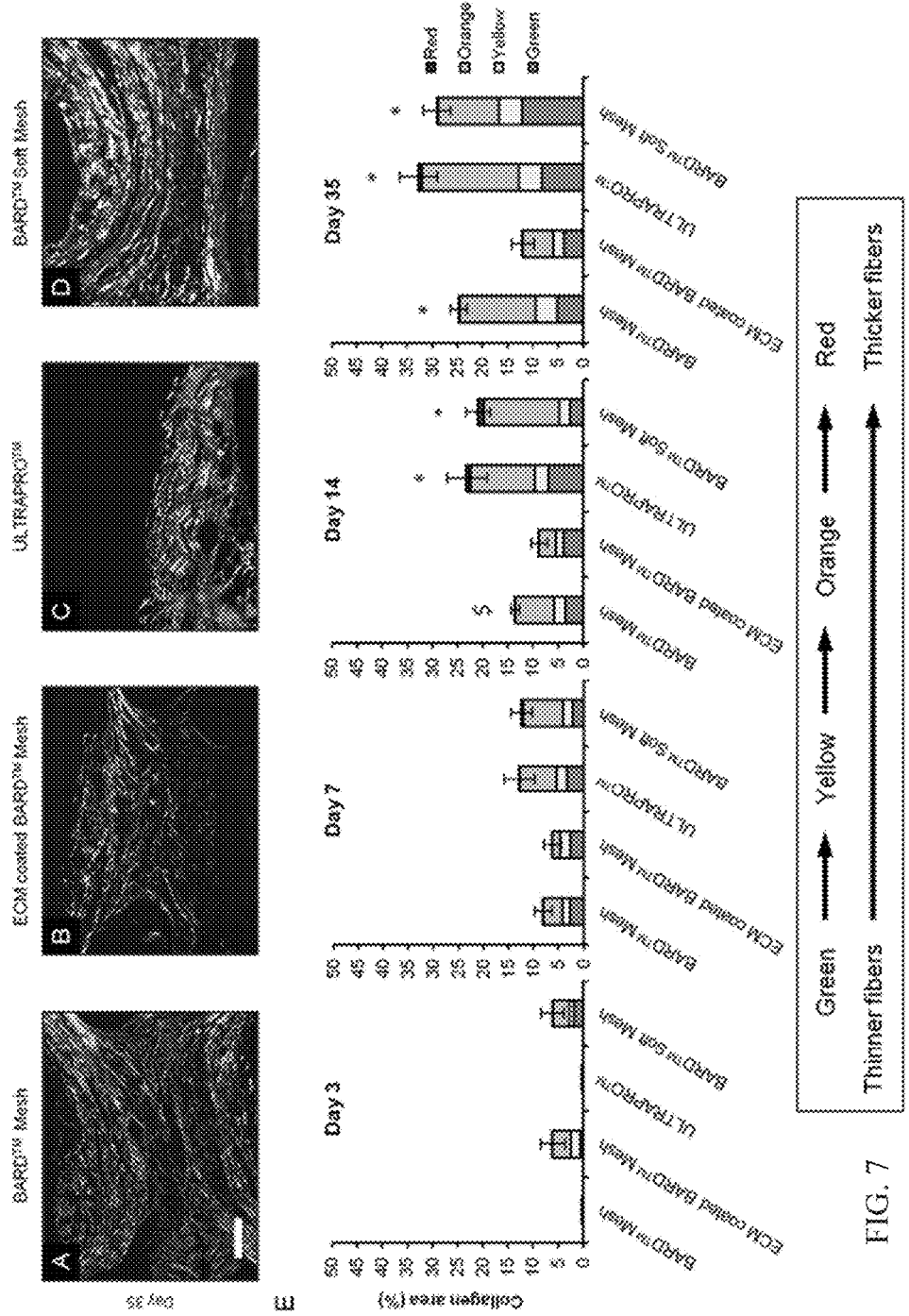
FIG. 7 shows picrosirius red staining and quantification of collagen area between mesh fibers using polarized light microscopy. Collagen fibers between the mesh fibers of each device (BARD™ Mesh (A), ECM-coated BARD™ Mesh (B), ULTRAPRO™ (C), and BARD™ Soft Mesh (D)) after 35 days. The color hue of the fibers represents the relative collagen thicknesses (in order of thinnest to thickest); E. quantification of the total area and proportion of collagen (defined by color hue) in each mesh after 3, 7, 14, and 35 days. Significant differences ($p<0.05$) in total collagen content between devices within each time point are denoted: (*) as different from the ECM coated BARD™ Mesh, ($) as different from ULTRAPRO™, and (#) as different from BARD™ Soft Mesh. Scale bar represents 100 µm.
Figure 10:
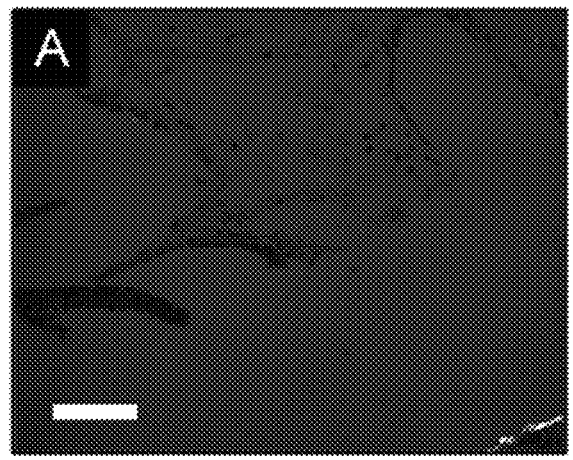
FIG. 10 shows picrosirius red staining and imaging with polarized light microscopy comparing: (A) BARD™ Mesh; and (B) ECM-coated BARD™ Mesh after 3 days of in vivo implantation. Scale bar represents 100 μm.
Figure 10:
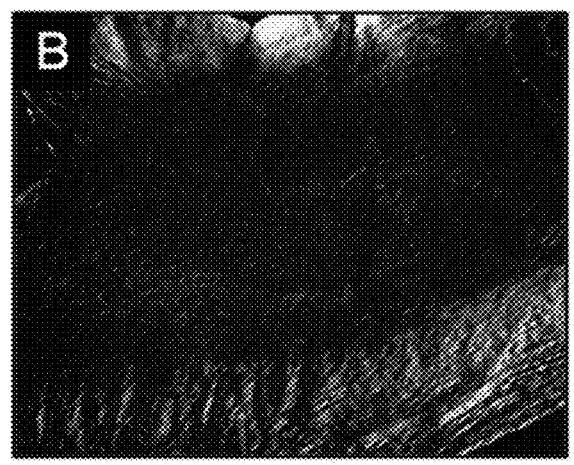

The cellularity (FIG. 6A-6B, top panels) and number of foreign body giant cells (FIG. 6A, top panel) were similar at the 3, 7, and 14 day time points for the uncoated mesh materials regardless of type, and the majority of these cells expressed the monocyte/macrophage surface marker CD68. However, by 35 days, there was an increase in the number of giant cells that had formed around the uncoated BARD™ Mesh compared to the earlier time points. In contrast, there was a negligible inflammatory cell response to the ECM coated mesh fibers until 14 days (FIG. 5A, panel D), at which point the inflammatory response was obvious but markedly reduced compared to the other materials. The histologic characteristics of the newly deposited tissue between mesh fibers varied with device type. The degree of cellularity (FIG. 6A, bottom panel) and vascularity (FIG. 6B, bottom panel) was similar for the uncoated BARD™ Mesh and the lightweight mesh devices. Although, these metrics were initially reduced for the ECM coated device compared to the heavy and light-weight devices, all devices were similar by the final time point. The ECM coating (FIG. 4A, panel C, FIG. 5A, panels C and D—ECM coating enclosed by dotted line) was not fully degraded until after the 14-day time point, after which it was replaced with loose connective tissue (FIG. 4A, panel D). The amount and fiber size of deposited collagen fibers between mesh fibers was lower for the ECM coated BARD™ Mesh compared to all other mesh devices after 35 days (FIG. 7, panels A-D) as shown with polarized light microscopy quantification (FIG. 7, panel E). However, the ECM coated mesh initially (3-day time point) had a greater collagen content than the uncoated heavy-weight mesh, which had minimally detectable amounts (FIG. 10).

Ex Vivo Mesh Biaxial Mechanical Properties

Figure 8:
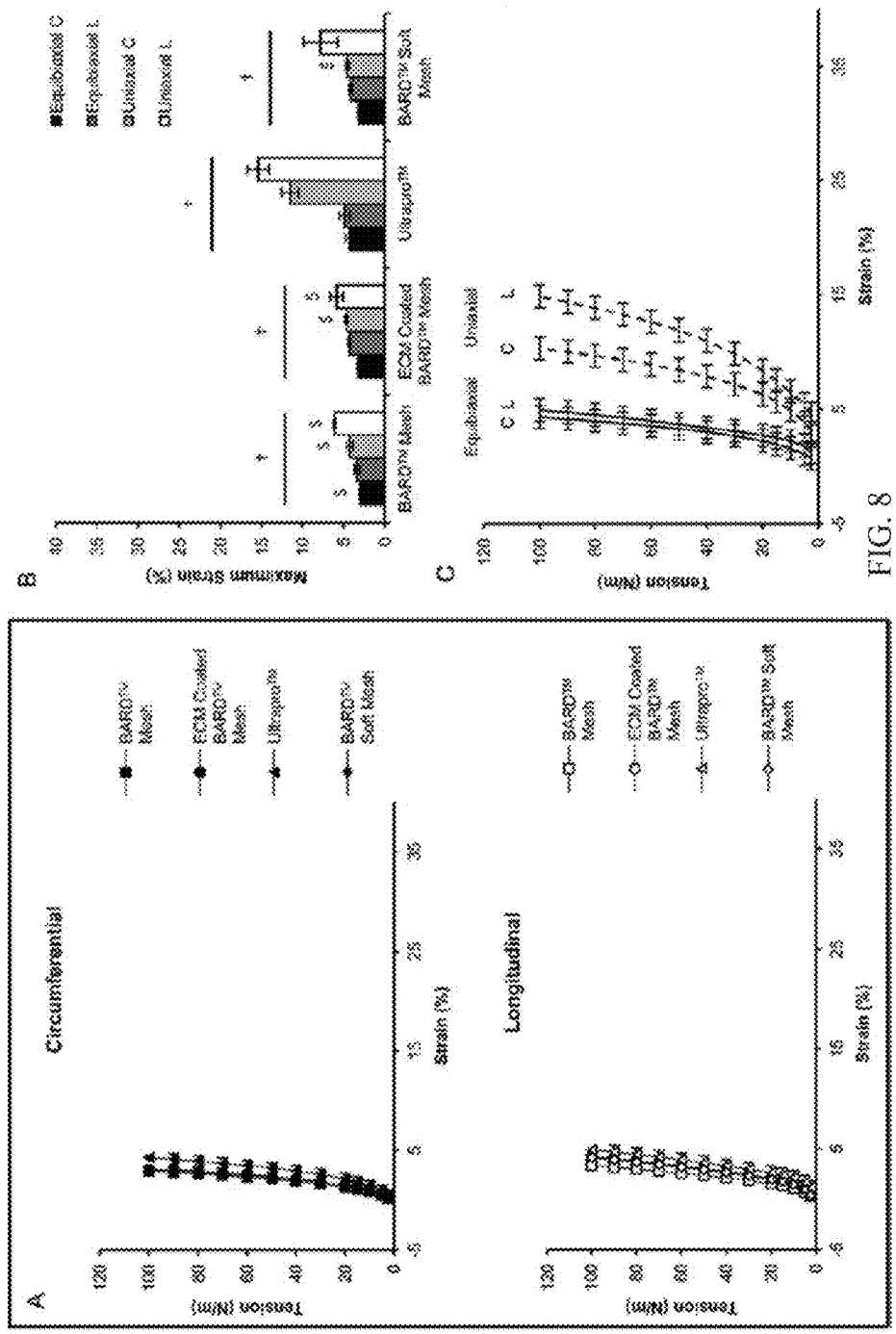
FIG. 8 shows pre-implantation mesh mechanical characterization: A. the equibiaxial tension response of mesh devices was characterized along the circumferential-C and longitudinal-L axes; B. the maximum strain defined at a tension of 100 N/m for both equibiaxial and uniaxial protocols; C. comparison of biaxial and uniaxial tension protocols for ULTRAPRO™ mesh along the circumferential-C and longitudinal-L axes. Significant differences (p<0.05) between ULTRAPRO™ and each material within the same axis and testing protocol are denoted with ($). Significant differences between equibiaxial and uniaxial testing protocols for each device are denoted with (†).
Figure 9:
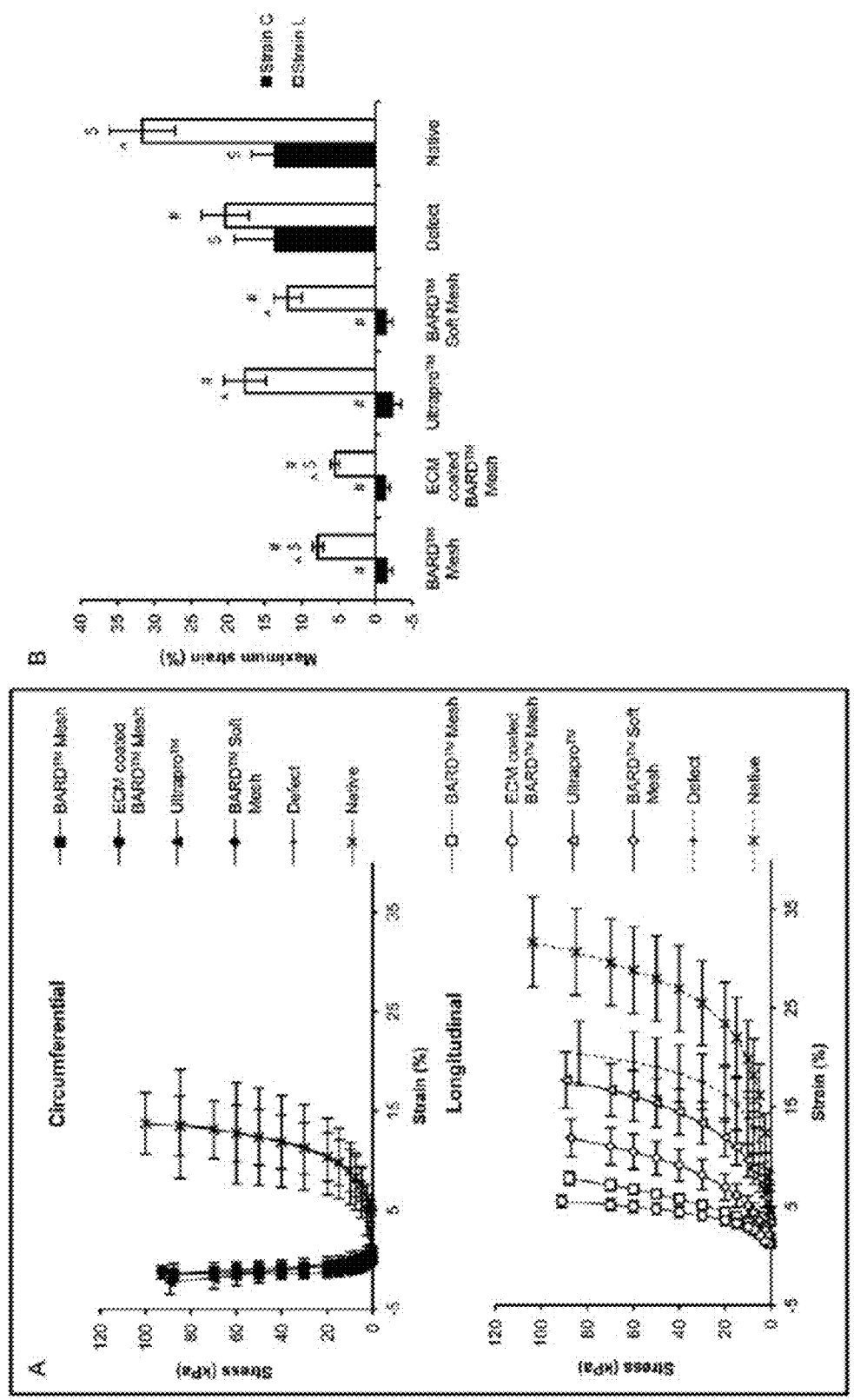
FIG. 9 shows equibixial characterization of mesh explants after 35 days: A. the equibiaxial stress response of the explanted mesh devices were characterized along the circumferential and longitudinal axes and; B. the maximum strain defined at a stress of 85 kPa for both circumferential-C and longitudinal-L axes. Significant differences (p<0.05) between the circumferential and longitudinal axes of the same sample are denoted with (^). Significant differences between samples in each axis are denoted as the following: ($) as different from ULTRAPRO™ and (#) as different from the uninjured native tissue.

All pre-implant mesh devices were stiff and isotropic under an equibiaxial stress protocol with strain less than 5% and no difference between mesh devices (p<0.05) in either axis (FIG. 8, panel A). The maximum strain of all pre-implant mesh devices was greater under a uniaxial protocol compared to an equibiaxial protocol. Maximum strain reached 16% for ULTRAPRO™ (FIG. 8, panel B), with a visible degree of anisotropy for each mesh. ULTRAPRO™ had the greatest uniaxial maximum strain and anisotropy compared to the biaxial loading protocol (FIG. 8, panel C) followed by BARD™ Soft Mesh (the light-weight mesh devices), while the pre-implant heavy-weight BARD™ Mesh and ECM coated BARD™ Mesh showed the lowest uniaxial maximum strain. The equibiaxial stress response of the native abdominal wall exhibited anisotropic behavior with a maximum strain of 14 and 32% in the circumferential and longitudinal direction, respectively (FIG. 9, panel A). The explanted unrepaired defect control had an isotropic response due to a decrease in compliance in the longitudinal direction compared to the native tissue with a 20% maximum strain. Mesh-tissue explants exhibited anisotropic behavior similar to the native tissue after 35 days, and were more compliant in the longitudinal axis compared to the circumferential axis. However, the maximum strains of all mesh-tissue explants in the circumferential direction were less than both the native and unrepaired defect controls (FIG. 9, panel B). The maximum strain in the longitudinal direction was highest for the light-weight mesh ULTRAPRO™ at 18% compared to the heavy-weight uncoated and coated BARD™ Mesh at approximately 7% strain.

The results clearly show the mitigating effect of the ECM coating upon the classic host foreign body response to polypropylene mesh material. This study also presents a detailed biaxial mechanical evaluation of mesh materials embedded within the abdominal wall tissue after 35 days. The ECM hydrogel coating was effective at markedly altering the histologic host remodeling response. The uncoated polypropylene mesh evoked a classic foreign body response, with a rapid accumulation of mononuclear cells and foreign body giant cells around mesh fibers, whereas the ECM-coated mesh attenuated the inflammatory response. During the acute phase after implantation relatively few host cells contacted the polypropylene mesh through the ECM coating, preventing the characteristic accumulation of CD68+ cells immediately adjacent to the mesh fibers. This effect persisted until at least 35 days, by which time the coating had degraded and been replaced by loose collagenous connective tissue. Direct cell contact with synthetic polymers has been shown to activate fibroblasts and macrophages in vitro to release pro-inflammatory cytokines that direct new tissue deposition and remodeling including TGF-$\beta$, IL-6, and matrix metalloproteinases. Thus the ECM coating may shield the mesh device from acute host inflammatory activation, promote filling of the pores with loose connective tissue, and facilitate the immunomodulatory effects described for implanted ECM scaffolds.

Example 17—Macrophage Polarization in Response to ECM Coated Polypropylene Mesh

Methods
Overview of Experimental Design

The temporospatial macrophage phenotype in response to a polypropylene mesh with and without an ECM hydrogel coating was evaluated in vivo. Dermal and urinary bladder tissue was decellularized to create D-ECM and UBM scaffolds, respectively, and applied as ECM hydrogel coatings (in hydrated and dried states) to a heavy-weight polypropylene mesh. Mesh devices were implanted in a partial thickness abdominal wall defect in the rat. The explanted mesh materials were immunolabeled for cell surface markers associated with M1 and M2 macrophage phenotypes at time points ranging from 3 to 35 days. All animal experiments were conducted in accordance to University of Pittsburgh Institutional Animal Care and Use Committee (IACUC) regulations and guidelines.

ECM Preparation and Mesh Coating

Dermal ECM (D-ECM) was prepared by decellularization of porcine skin as previously described (Reing J E et al. The effects of processing methods upon mechanical and biologic properties of porcine dermal extracellular matrix scaffolds. Biomaterials 2010; 31: 8626-8633; Wolf M T et al. A hydrogel derived from decellularized dermal extracellular matrix. Biomaterials 2012; 33: 7028-7038). The epidermis and subcutaneous tissue were mechanically removed to isolate the dermal layer (thickness approximately 1.5 mm), which was enzymatically and chemically decellularized in association with agitation by an orbital shaker (300 RPM). In brief, dermis was treated with 0.25% Trypsin (Sigma) for 6 hours, 70% ethanol for 10 hours, hydrogen peroxide for 15 min, 1% Triton X-100 in 0.26% EDTA/0.69% Tris-base for 6 hours followed by an additional 16 hours in fresh solution, and 0.1% peracetic acid/4% ethanol for 2 hours. All steps were performed at room temperature with extensive rinsing (3×15 min washes with deionized water) between each step and after the final step.

Urinary bladder matrix (UBM) was prepared from porcine urinary bladders via mechanical isolation of the basement membrane and tunica propria layers as described above. The tissue was rinsed in deionized water and decellularized with 0.1% PAA/4% ethanol (v/v) for 2 hours with agitation by an orbital shaker (300 RPM). The resulting UBM was rinsed extensively with PBS and deionized water.

Both D-ECM and UBM scaffolds were frozen, lyophilized, and comminuted into a particulate using a Wiley Mill passed through a 40 mesh screen. ECM powder was enzymatically digested and solubilized at an ECM concentration of 10 mg ECM (dry wt)/ml with 1 mg/ml pepsin in 0.01 M HCl. ECM pre-gel was prepared by neutralizing the partially digested ECM with 1/9 digest volume of 10×PBS, 1/10 the digest volume of 0.1 M NaOH, and dilution with 1×PBS to a final ECM concentration of 8 mg ECM (dry wt.)/ml. Heavy-weight polypropylene mesh (BARD™ Mesh, C.R. BARD Inc.) coupons (1 cm×1 cm) were embedded within molds (1.2 cm×1.2 cm) containing D-ECM or UBM pre-gel solutions and placed in a non-humidified incubator at 37° C. to initiate gelation. ECM hydrogels formed around the polypropylene mesh fibers and either remained in a hydrated form (D-ECM-wet and UBM-wet) or were further dried in a non-humidified incubator at 37° C. for 24 hours (D-ECM-dry and UBM-dry). All devices were sterilized prior to implantation with 2 Mrad gamma irradiation at room temperature.

Mesh coating efficacy was evaluated macroscopically and using scanning electron microscopy (SEM) of the uncoated and ECM coated mesh. Mesh devices were fixed with 2.5% glutaraldehyde for 1 hour and washed with PBS. Devices were then dehydrated with a graded series of ethanol (30%, 50%, 70%, 90%) for 30 minutes each, followed by an overnight wash in 100% ethanol and 2 additional 30 minute washes in ethanol. Mesh devices were then critically point dried using carbon dioxide as the transitional drying medium. Samples were sputter coated with a 3.5 nm gold palladium alloy and imaged using 10 keV accelerating voltage.

ECM Coated Mesh Implantation in an Abdominal Skeletal Muscle Injury Model

Uncoated and ECM-coated mesh devices were surgically implanted in an established abdominal wall injury model in the rat. Female rats (250-300 g, Sprague-Dawley, Charles Rivers Inc) were anesthetized with 1.5-3% isofluorane followed by bilateral paramedian skin incisions access the abdominal wall. Bilateral partial thickness skeletal muscle defects (1 cm×1 cm) were created by excision of the external and internal oblique muscles while leaving the underlying transversalis fascia intact. In the randomized mesh device groups, mesh devices were inlaid within the muscle defect and affixed to the abdominal wall with polypropylene sutures (Prolene) at each corner. Animals were allowed to recover and ambulate normally until sacrifice and mesh explantation at 3, 7, 14, or 35 days (n=5 rats per device at each time point).

Figure 11:
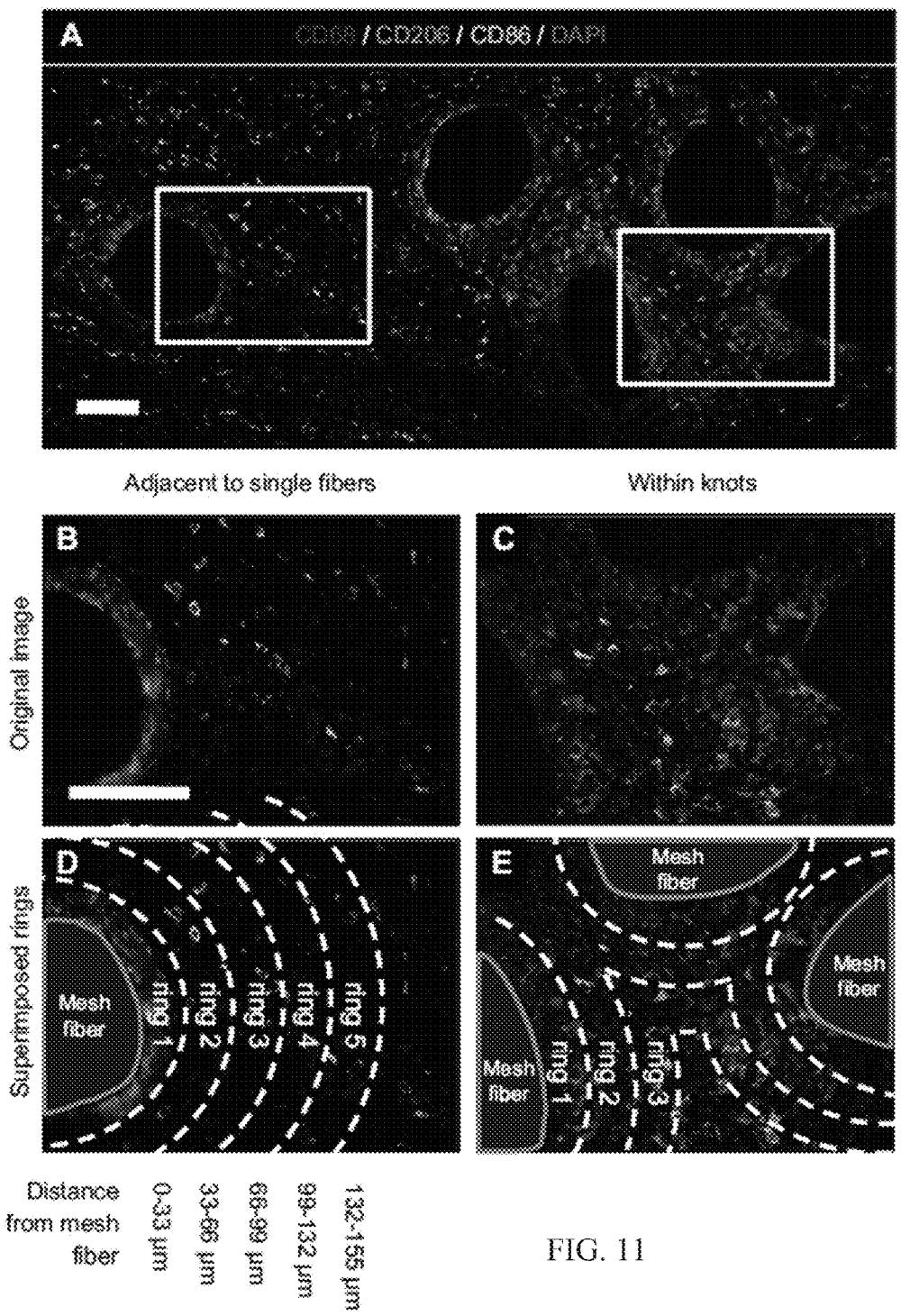
FIG. 11 shows immunofluorescent mesh imaging and spatial quantification of polarized macrophages. Representative low magnification (100×) immunofluorescent image of an uncoated polypropylene mesh (A) with white boxes indicating the regions of interest for high magnification image acquisition (400×) for macrophage quantification. Images were acquired at the edge of single mesh fibers (B) and within mesh fiber knots (C). The spatial distribution of polarized macrophages relative to the tissue-mesh fiber interface was quantified within the areas of concentric rings (dotted lines) evenly spaced around mesh fibers (D, E). Each ring represents an increased radius of 33 mm from the mesh fiber. Macrophage phenotype was identified via surface markers: CD68+pan-macrophage, CD86+M1 macrophage, and CD206+M2 macrophage co-localized with DAPI stained nuclei. Scale bars represent 100 mm.

Histologic Analysis of Macrophage Phenotype and Host Remodeling in Response to ECM Coated Mesh Implantation Explanted mesh with surrounding abdominal wall tissue was fixed with 10% neutral buffered formalin for at least 24 h, embedded in paraffin, and sectioned (5 mm). Immnofluorescent labeling was performed to characterize macrophage phenotype in response to ECM coated and uncoated polypropylene mesh test articles. Slides were deparaffinized followed by antigen retrieval in heated citrate buffer for 20 min (10 mM citrate, pH 6.0 at 95-100° C.). Non-specific antibody binding was prevented via incubation for 1 h at room temperature with a blocking solution consisting of 2% normal horse serum (Hyclone), 1% bovine serum albumin (Sigma), 0.1% Triton X-100 (Sigma), and 0.1% Tween-20 (Sigma) in PBS. Sections were decanted and incubated with primary antibodies diluted 1:150 in blocking solution overnight at 4° C. Primary antibodies against the pan-macrophage marker CD68 (mouse anti-rat CD68, clone ED1, Abd Serotec), the M1 macrophage marker CD86 (rabbit anti-human CD86, clone EP1158Y, Abcam), and the M2 macrophage marker CD206 (goat anti-human CD206, polyclonal, Santa Cruz) were used. Sections were washed and incubated with the following fluorescently conjugated secondary antibodies diluted in blocking solution for 1 h at room temperature: donkey anti-mouse Alexa Fluor-594 (1:200 dilution, Invitrogen), donkey anti-rabbit PerCPCy5.5 (1:300 dilution, Santa Cruz), and donkey anti-goat Alex Fluor-488 (1:200 dilution, Invitrogen). Nuclei were labeled with DAPI and slides coverslipped with fluorescent mounting medium (Dako). Multispectral epifluorescent images were acquired (Nuance multispectral imaging system, CRi Inc.) and spectrally unmixed to remove background autofluorescence. A total of 6 high magnification images (400×) distributed across 2 locations within the mesh device were acquired (FIG. 11, panel A, boxes). Representative fields of view were centered at both the mesh fiber pore interface adjacent to single fibers (FIG. 1B) and centered within mesh knot structures (FIG. 11, panel C). The total number of cells co-expressing CD68 and either CD86 or CD206 was automatically quantified for each image using CellProfiler software. Macrophages were defined as CD68 positive co-localized with nuclei. M1 and M2 cells were defined as macrophages co-expressing CD86 or CD206, respectively. A subpopulation of cells co-expressed both M1 and M2 markers and were subsequently denoted as "co-labeled".

Macrophage spatial distribution relative to mesh fibers was characterized by defining concentric rings around mesh fibers that were evenly spaced at 33 mm intervals as shown in FIG. 11. A total of 5 ring areas were defined around single fibers and 3 rings within fiber knots. Cells on the border of 2 rings were counted towards the inner ring and any overlapping ring areas between knots were counted only once. The total number of macrophages in each phenotypic state and the ratio of M2:M1 macrophages were determined for each device/time point/spatial location. The M2:M1 ratio was calculated as the (# of M2 macrophages+1)/(#M1 macrophages+1) to accommodate conditions in which there were no M1 and/or M2 macrophages present within the region of interest.

Histologic remodeling was evaluated from Masson's Trichrome stained sections. High powered (400×) images were acquired using the same strategy described above (at the mesh fiber pore interface and at mesh fiber knots). Each image was quantified by blinded observers for total number of multinucleate foreign body giant cells and blood vessels. Blood vessels were defined as structures possessing a lumen with red blood cells within.

All results are presented as the mean±the standard error of the mean (SEM). Statistical analysis was performed using a three-way ANOVA evaluating ECM type, ECM coating method, and spatial location for each variable (M1, M2, etc)

within each time point using SPSS software. A post-hoc test was conducted with a p-value <0.05 considered statistically significant.

Results

ECM Preparation and Mesh Coating

D-ECM and UBM were successfully prepared from porcine dermis and urinary bladder tissue, respectively, and enzymatically processed into a hydrogel form.

Figure 12:
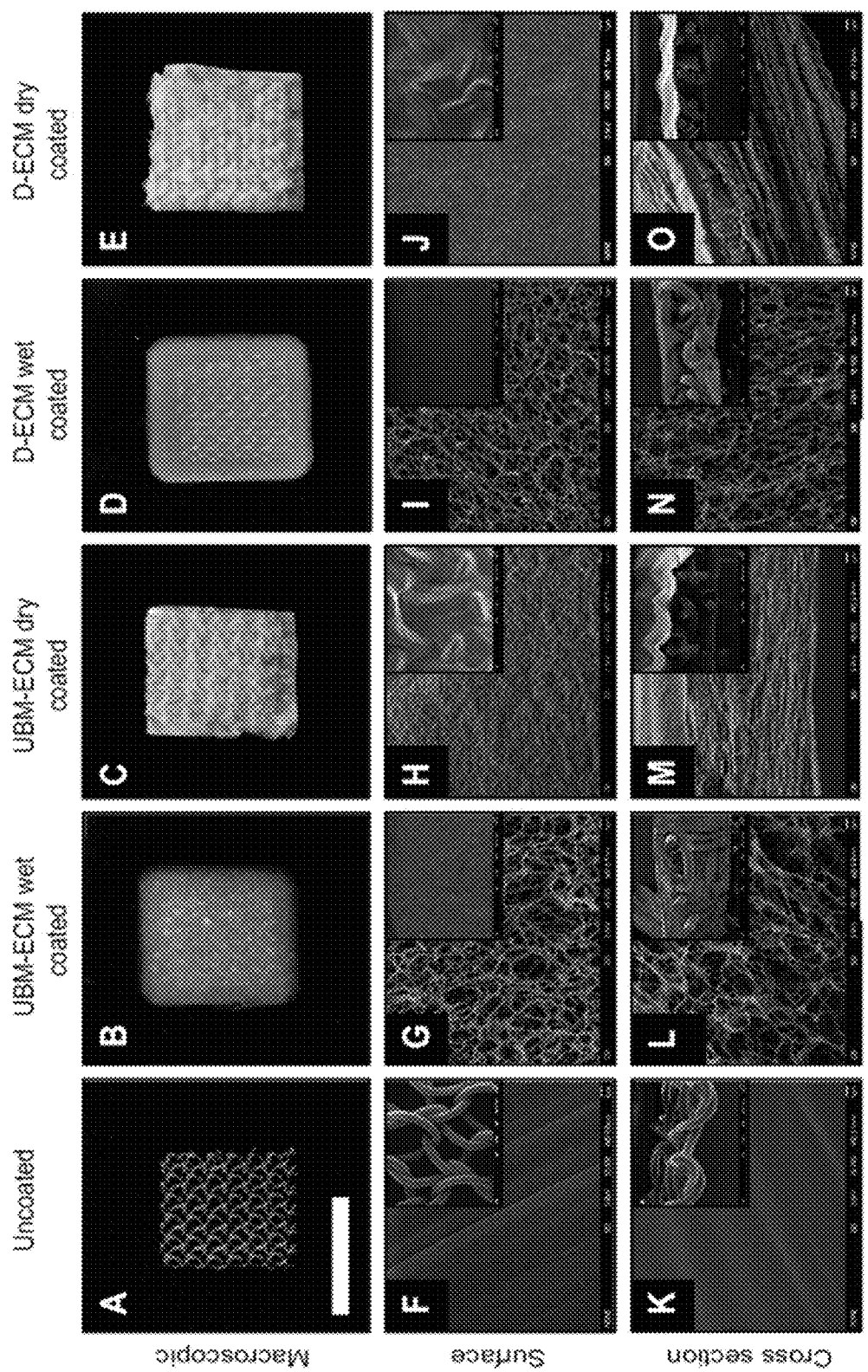
FIG. 12 shows ECM coating coverage and structure. Representative macroscopic images of an uncoated polypropylene mesh (A), UBM-ECM wet hydrogel coated mesh (B), UBM-ECM dried hydrogel coated mesh (C), D-ECM wet hydrogel coated mesh (D), and dried D-ECM hydrogel coated mesh (E). Scale bar represents 1 cm. Scanning electron micrographs of the surfaces and cross sections of an uncoated and wet/dried ECM coated hydrogel coated mesh. High magnification images of mesh structure (5000×) are provided with low magnification images of coating coverage (50×, inset).

Polypropylene mesh coupons (FIG. 12, panel A) were embedded within ECM hydrogels (FIG. 12, panels B-E). Both dried and wet ECM coatings fully covered the mesh fiber surface and filled the pores between mesh fibers, as well as within the interstices between mesh fiber knots as shown by macroscopic observation and SEM (FIG. 12, panels G-J, inserts). Ultrastructural examination showed that the smooth surface of polypropylene mesh fibers (FIG. 12, panel F) was covered with ECM hydrogels that imparted distinct structural characteristics depending upon the type of coating. Both UBM-ECM and D-ECM wet hydrogel coatings (FIG. 12, panels G-J) had a randomly oriented fibrillary structure, and the D-ECM fibril network was denser than UBM-ECM. Drying the ECM hydrogel coating induced structural changes to both UBM-ECM and D-ECM hydrogel coatings (FIG. 12, panels H and J). The dried hydrogel coatings appeared as a textured surface of randomly oriented raised patterns and indentations reminiscent of collapsed ECM fibrils.

SEM cross sections confirmed the presence of both wet and dried ECM hydrogel coating throughout the mesh pores and within mesh fiber knots. The wet ECM hydrogel coatings (FIG. 12, panels L and N, inserts) had fibrillar structural characteristics (FIG. 12, panels L and N) that were similar to the surface images. UBM-ECM and D-ECM dried hydrogel coatings were very thin compared to the wet hydrogels (FIG. 12, panels M and O, insets) and tightly conformed to the mesh fiber topography. High magnification ross sections of dried ECM coatings showed lamellar sheets with occasional fibrils crossing between layers (FIG. 12, panels M and O).

Figure 13:
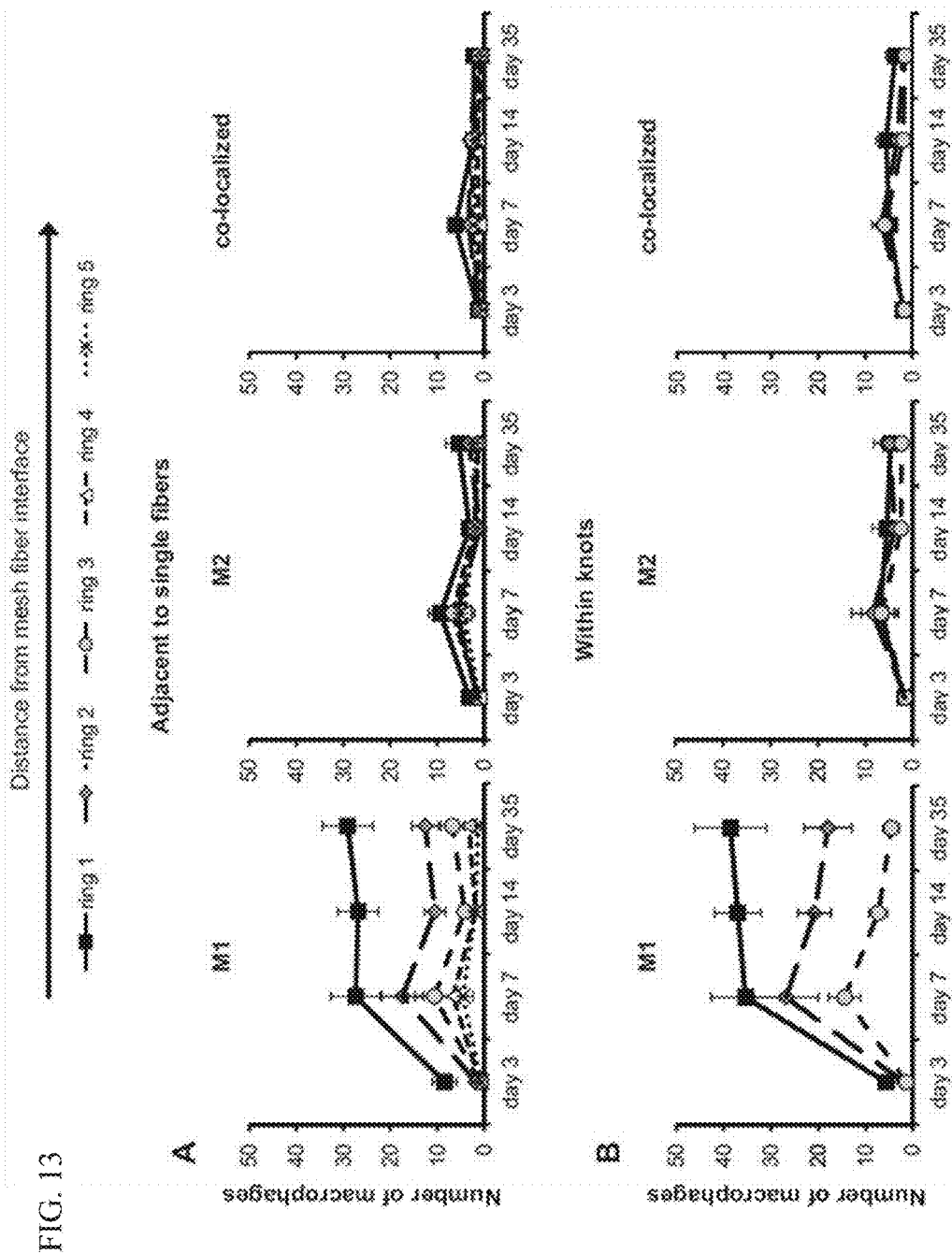
FIG. 13 shows spatiotemporal macrophage response to uncoated polypropylene mesh. The number of M1 (CD86+/CD68+), M2 (CD206+/CD68+), and co-localized (CD86+/CD206+/CD68+) macrophages adjacent to single mesh fibers (A) and within knots (B) were quantified with respect to distance from the tissue-mesh fiber interface. Each ring (1-5) represents increasing distance from the mesh fiber surface after 3, 7, 14, and 35 days post implantation.

Histologic Analysis of Macrophage Phenotype and Host Remodeling in Response to ECM Coated Mesh Implantation Macrophage phenotype was evaluated via the coexpression of the pan-macrophage cell surface marker CD68 with the M1 marker CD86 and/or the M2 marker CD206. Macrophage phenotypic expression in response to an uncoated polypropylene mesh was similar in areas both adjacent to single fibers (FIG. 13, panel A) and within fiber knots (FIG. 13, panel B) and characterized by a dominant M1 response. The number of M1 macrophages was greatest in ring 1, which was the area in closest proximity to the mesh fiber, and decreased with increased distance from the mesh fiber approaching background levels by ring 3 in areas adjacent to single fibers. The number of M2 and M1+M2 co-labeled macrophages remained at low background levels at all time points. The initial day 3 M1 response within ring 1 markedly increased by day 7, and remained approximately constant at the 14 and 35 day time points. This pattern of macrophage distribution was observed for both individual mesh fiber and at fiber knot locations.

Figure 14A:
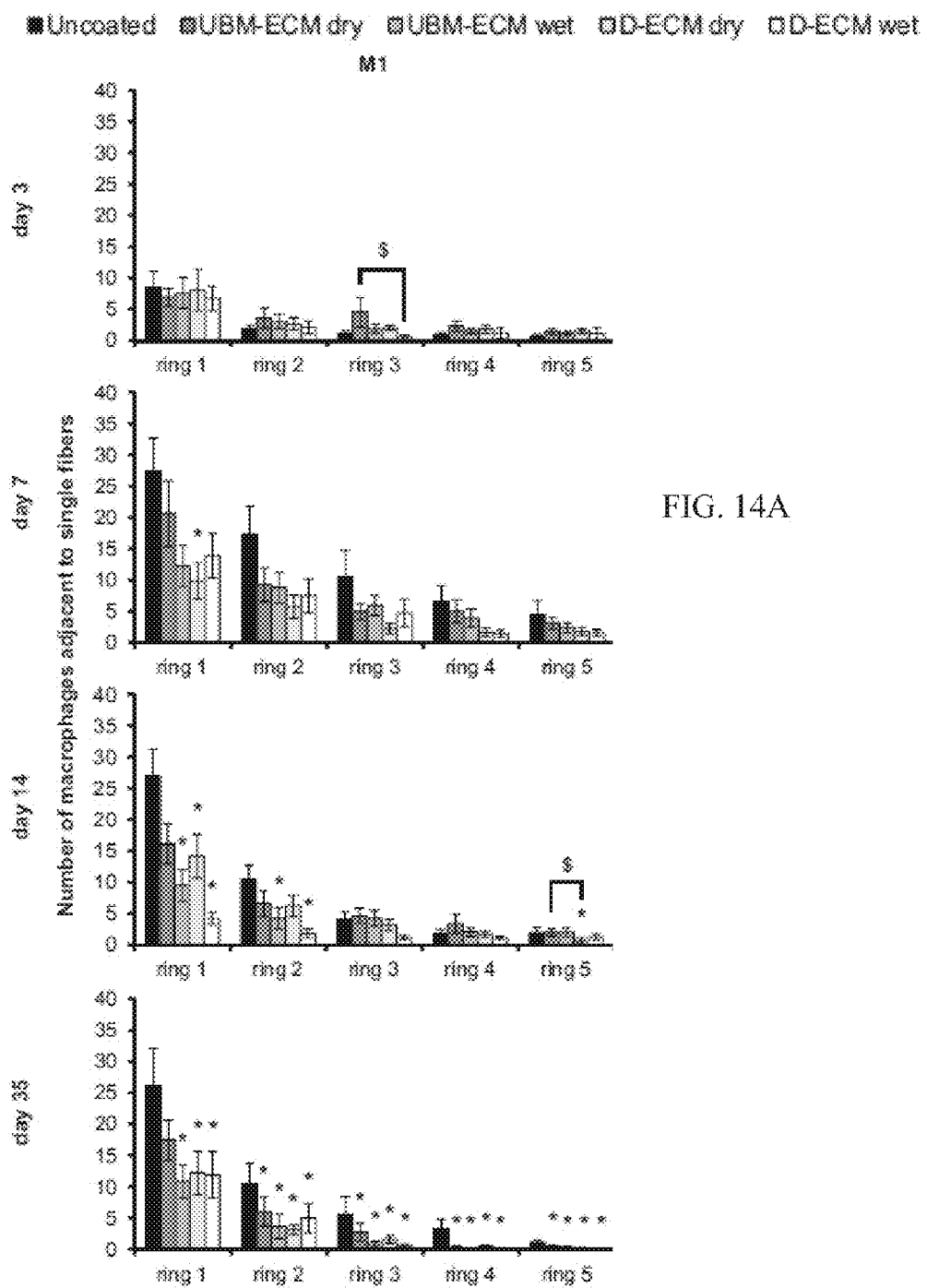
FIG. 14A-14B shows macrophage polarization adjacent to single mesh fibers in uncoated and ECM hydrogel coated mesh. The number of M1 (CD86+/CD68+) and M2 (CD206+/CD68+) macrophages in response to uncoated, UBM-ECM dry coated, UBM-ECM wet coated, D-ECM dry coated, and D-ECM wet coated polypropylene mesh were quantified from high magnification images of implanted mesh adjacent to single fibers. Total M1 and M2 macrophages were counted at each increasing distance interval from the mesh fiber surface (ring 1-5) at 3, 7, 14, and 35 day time points. Statistical significant differences were determined with ANOVA (p<0.05) and denoted with (*) as different from uncoated mesh, or ($) as different between ECM coating groups.
Figure 14B:
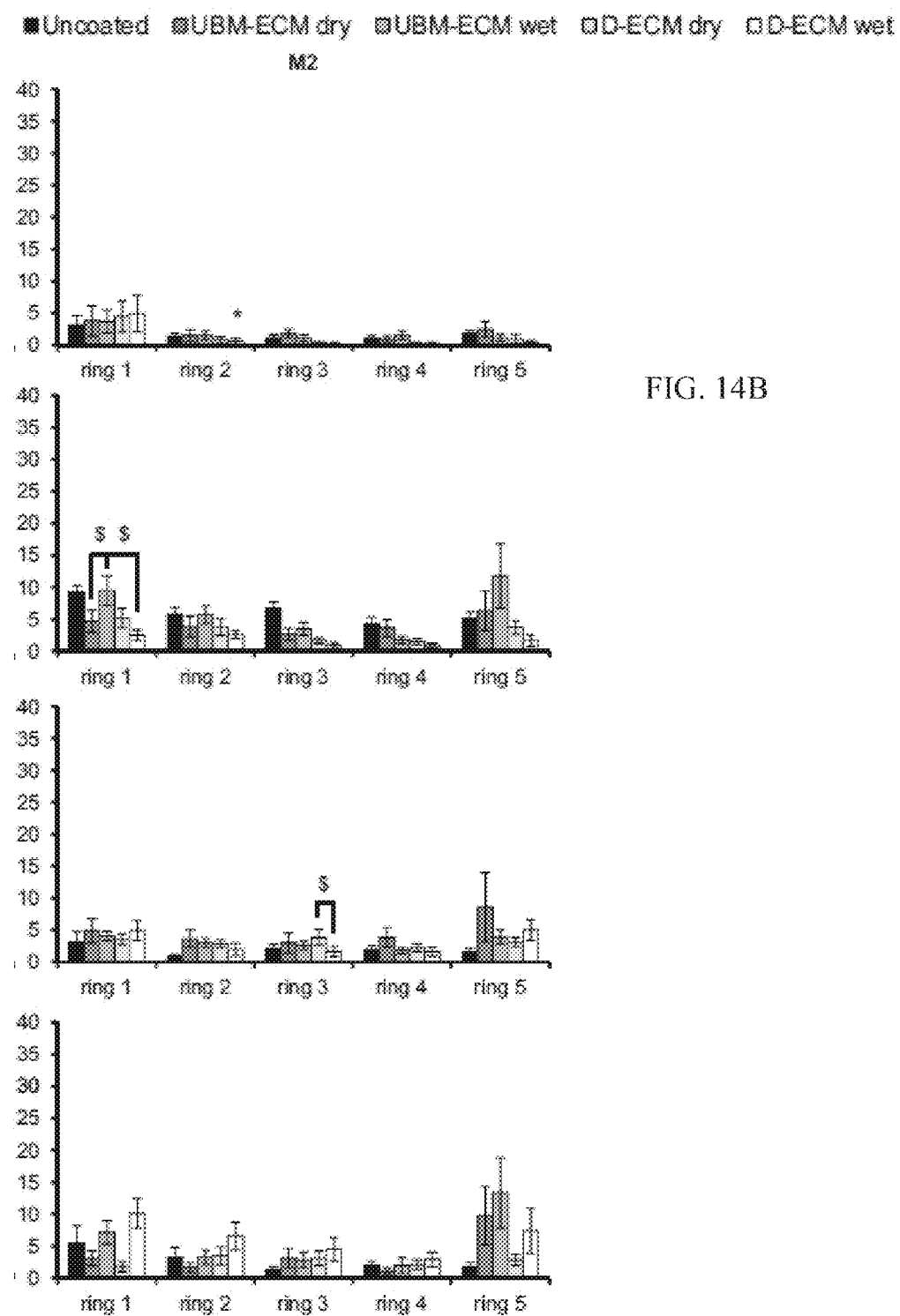
Figure 15A:
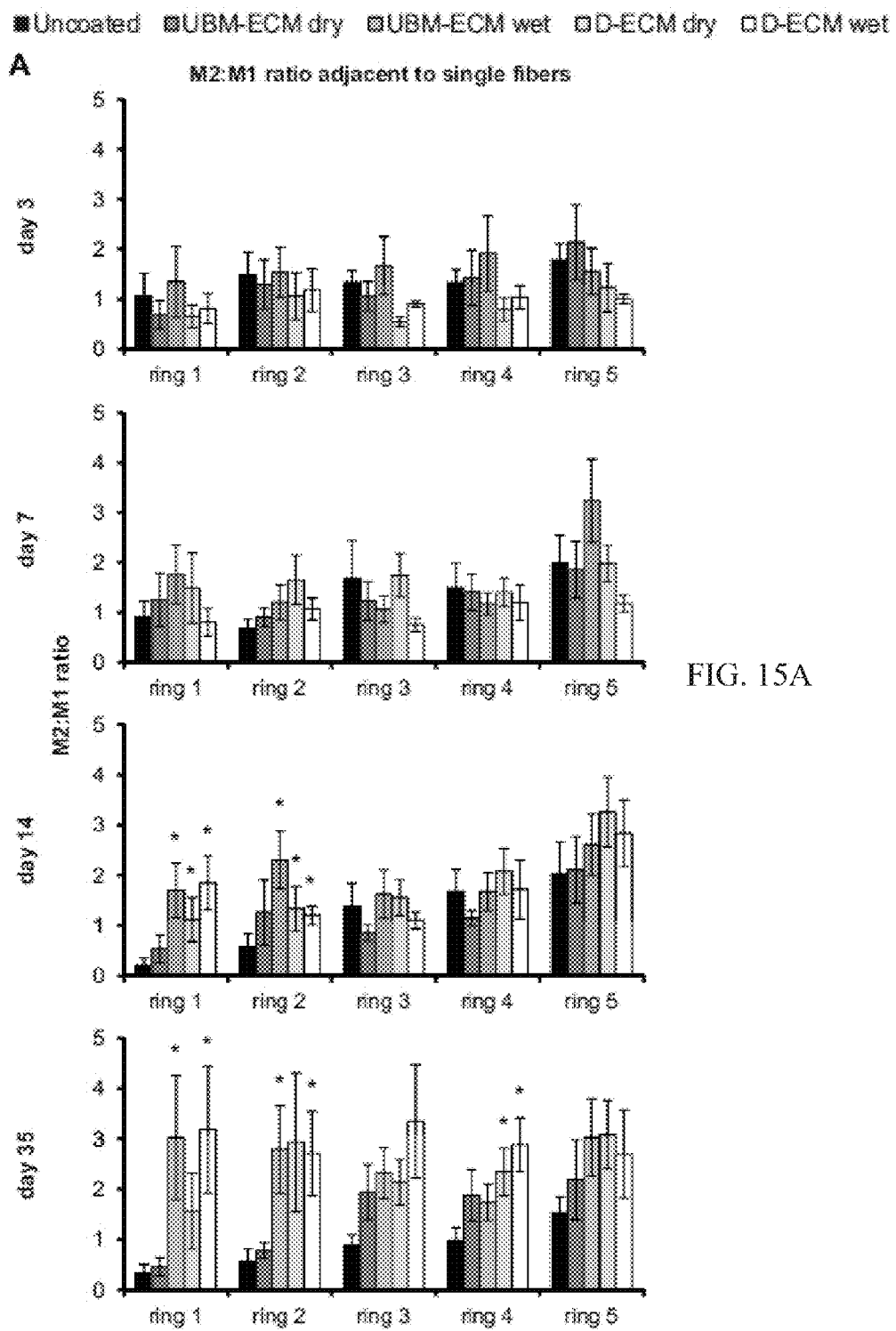
FIG. 15A-15B shows M2:M1 polarized macrophage ratio adjacent to single mesh fibers. The ratio of M2 to M1 macrophages in response to uncoated, UBM-ECM dry coated, coated UBM-ECM wet coated, D-ECM dry coated, and D-ECM wet coated polypropylene mesh was determined with distance (ring 1-5) from the mesh fiber surface at 3, 7, 14, and 35 days post implantation (A). Representative images of uncoated polypropylene mesh (B, D, F, H) and UBM-ECM wet coated mesh (C, E, G, I) are shown at each time point. Statistical significant differences were determined with ANOVA (p<0.05) and denoted with (*) as different from uncoated mesh, or ($) as different between ECM coating groups. Scale bar represents 100 mm.
Figure 15B:
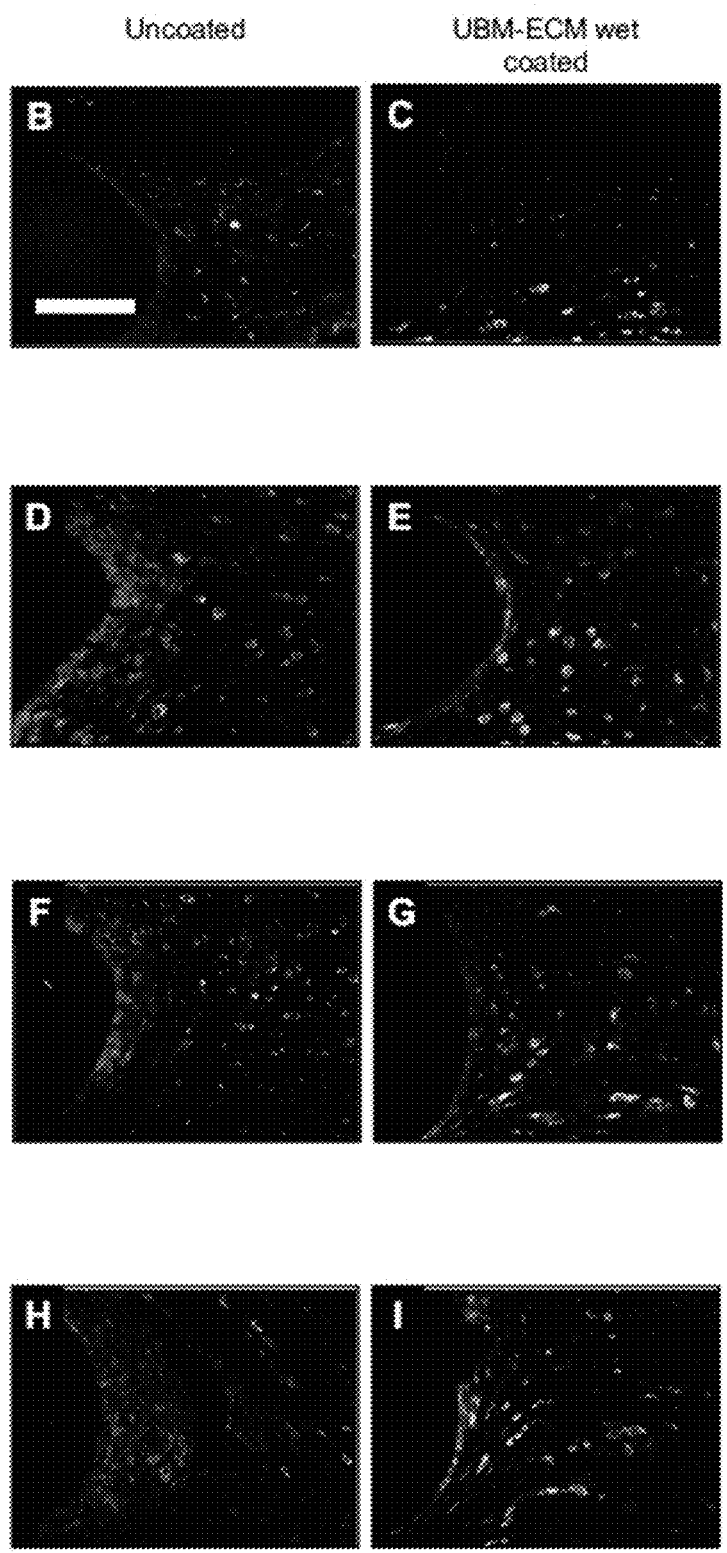

Each ECM coating type reduced the total number of macrophages present directly adjacent to single fibers compared to an uncoated mesh at the evaluated time points (FIG. 14A-14B). Similar to the uncoated mesh, the M1 accumulation was greatest in ring 1 and rapidly decreased with distance. The number of M1 macrophages around ECM coated mesh was lowest at the day 3 time point, and were not different from the uncoated mesh. Only the D-ECM dry coating affected the M1 response within ring 1 at day 7, though by day 14, each coating had reduced the M1 response, except for the UBM-ECM dry coating. The effect of the ECM coating was most pronounced by the 35 day time point, where M1 macrophage accumulation was attenuated at all distances (rings 1-5). Few differences in the number of M1 cells were observed between different ECM coating types, and none of the coating types consistently affected the number of M2 cells at any time point or distance. The effect of each ECM coating was also evaluated by calculating the ratio of M2 to M1 macrophages (FIG. 15A-15B). All ECM coatings except for the UBM-ECM dry increased the M2:M1 ratio within rings 1 and 2 adjacent to individual fibers by 14 days, but not at earlier time points. An increased M2:M1 ratio was also observed for both the UBM-ECM and D-ECM wet hydrogel coatings at 35 days.

Figure 16:
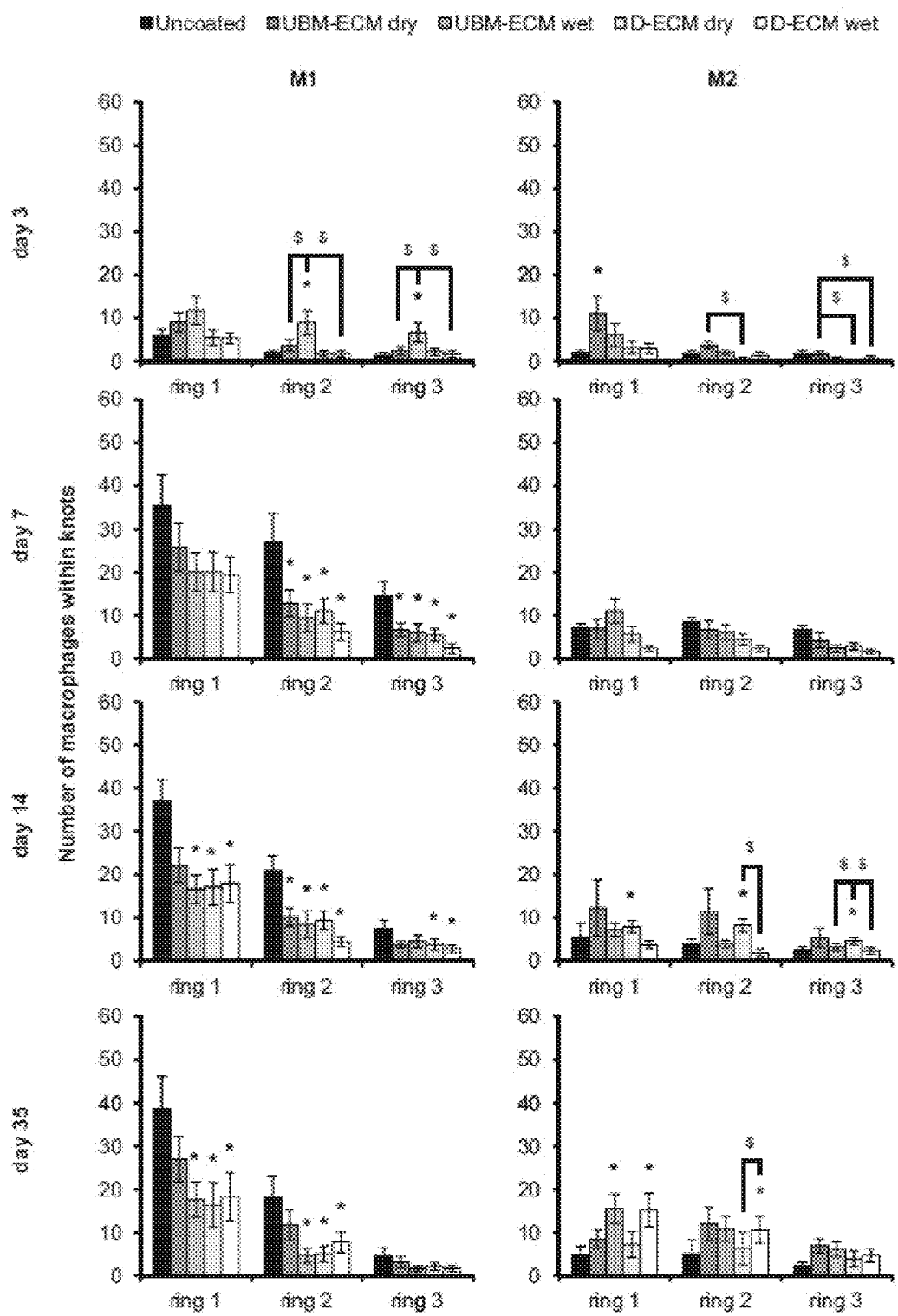
FIG. 16 shows Macrophage polarization within mesh fiber knots in uncoated and ECM hydrogel coated mesh. The number of M1 (CD86+/CD68+) and M2 (CD206+/CD68+) macrophages in response to uncoated, UBM-ECM dry coated, UBM-ECM wet coated, D-ECM dry coated, and D-ECM wet coated polypropylene mesh were quantified from high magnification images of implanted mesh within fiber knots. Total M1 and M2 macrophages were counted at each increasing distance interval from the mesh fiber surface (ring 1-3) at 3, 7, 14, and 35 day time points. Statistical significant differences were determined with ANOVA (p<0.05) and denoted with (*) as different from uncoated mesh, or ($) as different between ECM coating groups.
Figure 17A:
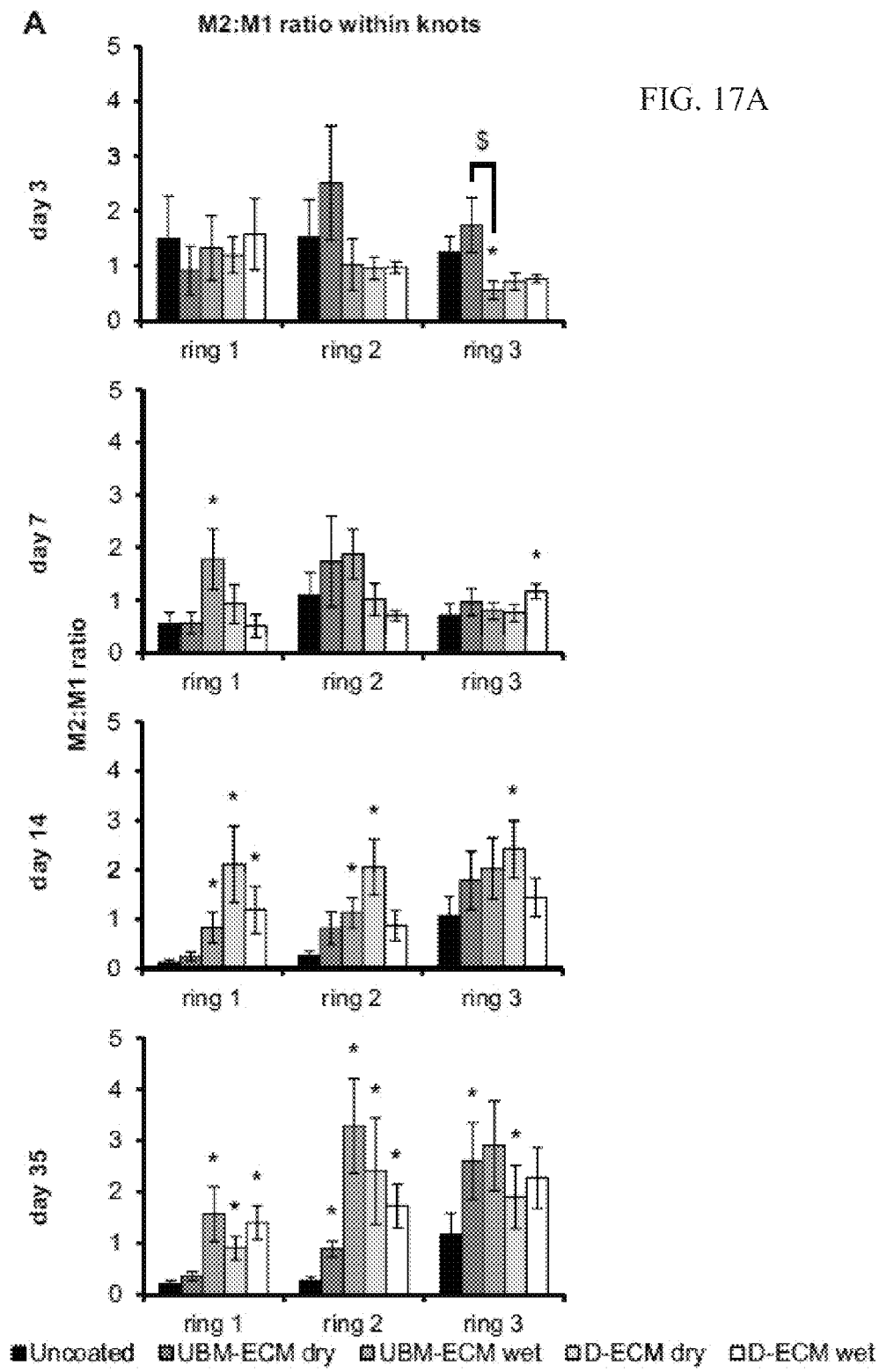
FIG. 17A-17B shows M2:M1 polarized macrophage ratio within mesh fiber knots. The ratio of M2 to M1 macrophages in response to uncoated, UBM-ECM dry coated, coated UBM-ECM wet coated, D-ECM dry coated, and D-ECM wet coated polypropylene mesh was determined for each distance (ring 1-3) from the mesh fiber surface at 3, 7, 14, and 35 days post implantation within fiber knot locations (A). Representative images of uncoated polypropylene mesh (B, D, F, H) and UBM-ECM wet coated mesh (C, E, G, I) are shown at each time point. Statistical significant differences were determined with ANOVA (p<0.05) and denoted with (*) as different from uncoated mesh, or ($) as different between ECM coating groups. Scale bar represents 100 mm.
Figure 17B:
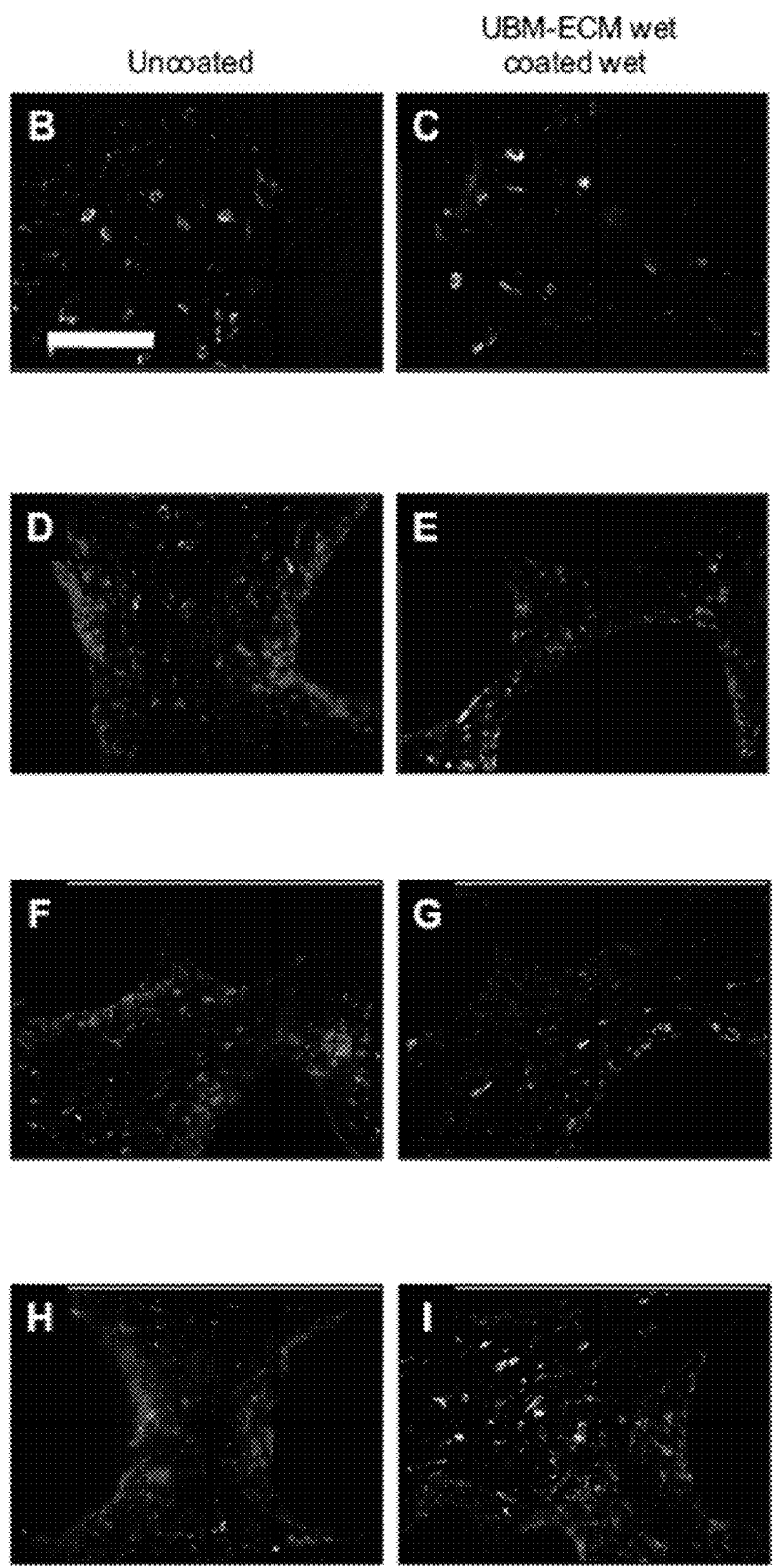

The ECM coatings had a similar effect within fiber knots; a location in which ECM coatings reduced the M1 response compared to an uncoated mesh at day 7, 14, and 35 time points (FIG. 16). Though the number of M1 cells diminished with distance from the mesh fiber, the reduction in M1 cells for all ECM coatings typically persisted through rings 1-3. All ECM coatings significantly decreased the number of M1 cells in rings 2-3 by 7 days and in most rings at day 14. All coatings except for UBM-ECM dry reduced the M1 response in rings 1-2 at day 35 with no differences by ring 3. There were no differences in the number of M1 cells between ECM coating types at any time point except at the 3 day time point where the number of M1 macrophages was greater for the UBM-ECM wet hydrogel coating. There were fewer M2 macrophages compared to M1 for all test articles, with only minor increases in number of M2 cell resulting from ECM coating. The ratio of M2:M1 macrophages within the knots of uncoated polypropylene mesh was increased by ECM coatings following the 3 day time point (FIG. 17A-17B). Only the UBM-ECM and D-ECM wet hydrogel coatings showed an increased M2:M1 ratio at the 7 day time point, and the M2:M1 ratio for all ECM coatings except for the dried UBM-ECM was increased at all distances at the 14 day time point. The increased M2:M1 ratio was observed for all ECM coatings at the 35 day time point at ring 2, and for all coatings except for dried UBM-ECM within ring 1. There were no differences in the M2:M1 ratio of different ECM coatings at any time point, except between UBM-ECM dry and wet coatings at day 3.

Figure 18A:
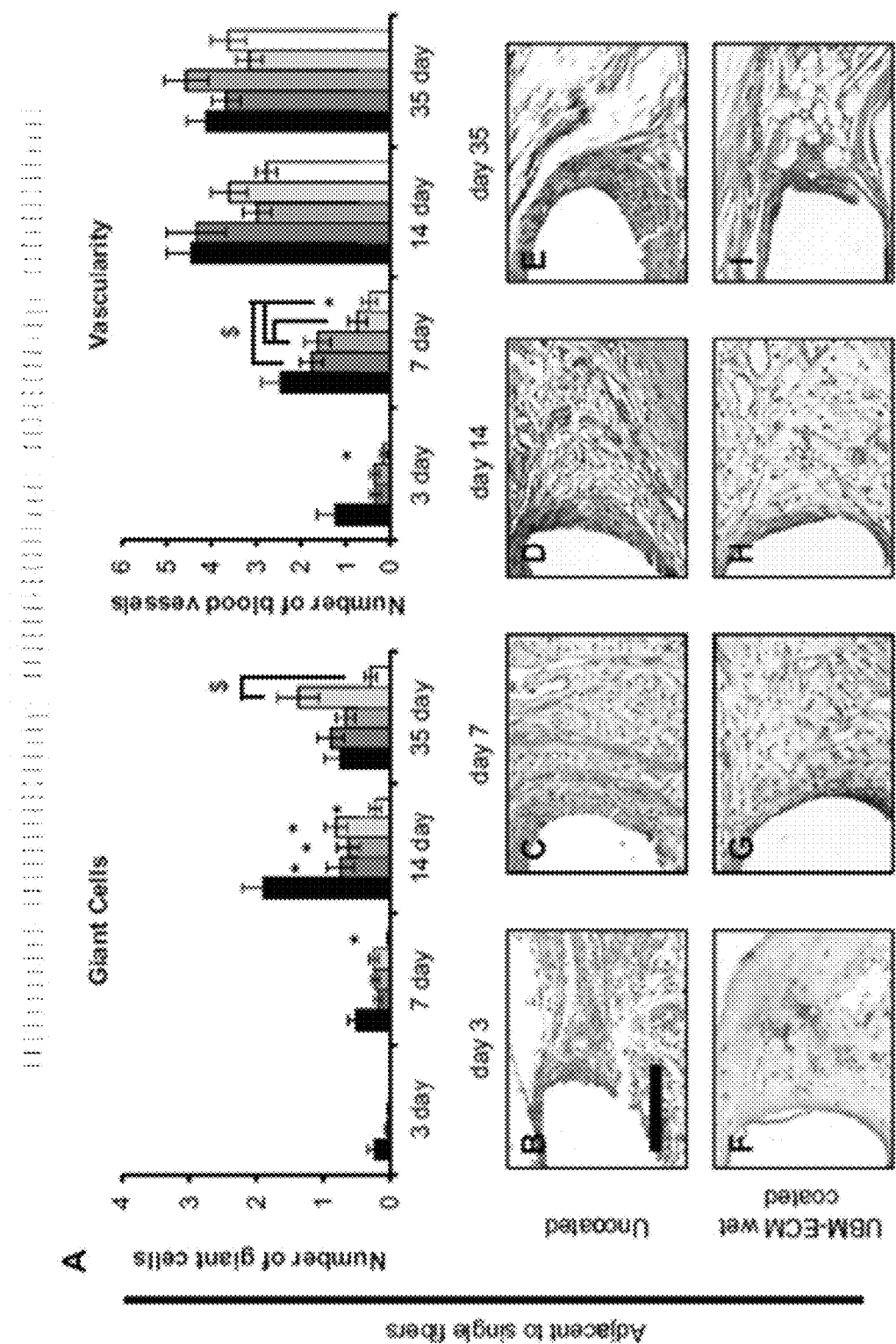
FIG. 18A-18B shows Histologic remodeling response to uncoated and ECM hydrogel coated mesh. The total number of foreign body giant cells and blood vessels was quantified from high magnification (400×) Masson's Trichrome stained images adjacent to single mesh fibers (A) and within mesh fiber knots (J) after 3, 7, 14, and 35 days post implantation. Representative images of uncoated polypropylene mesh (B-E, K-N) and UBM-ECM wet coated mesh (F-I, O-R) are shown at each time point. Statistical significant differences were determined with ANOVA (p<0.05) and denoted with (*) as different from uncoated mesh, or ($) as different between ECM coating groups. Scale bar represents 100 mm.
Figure 18B:
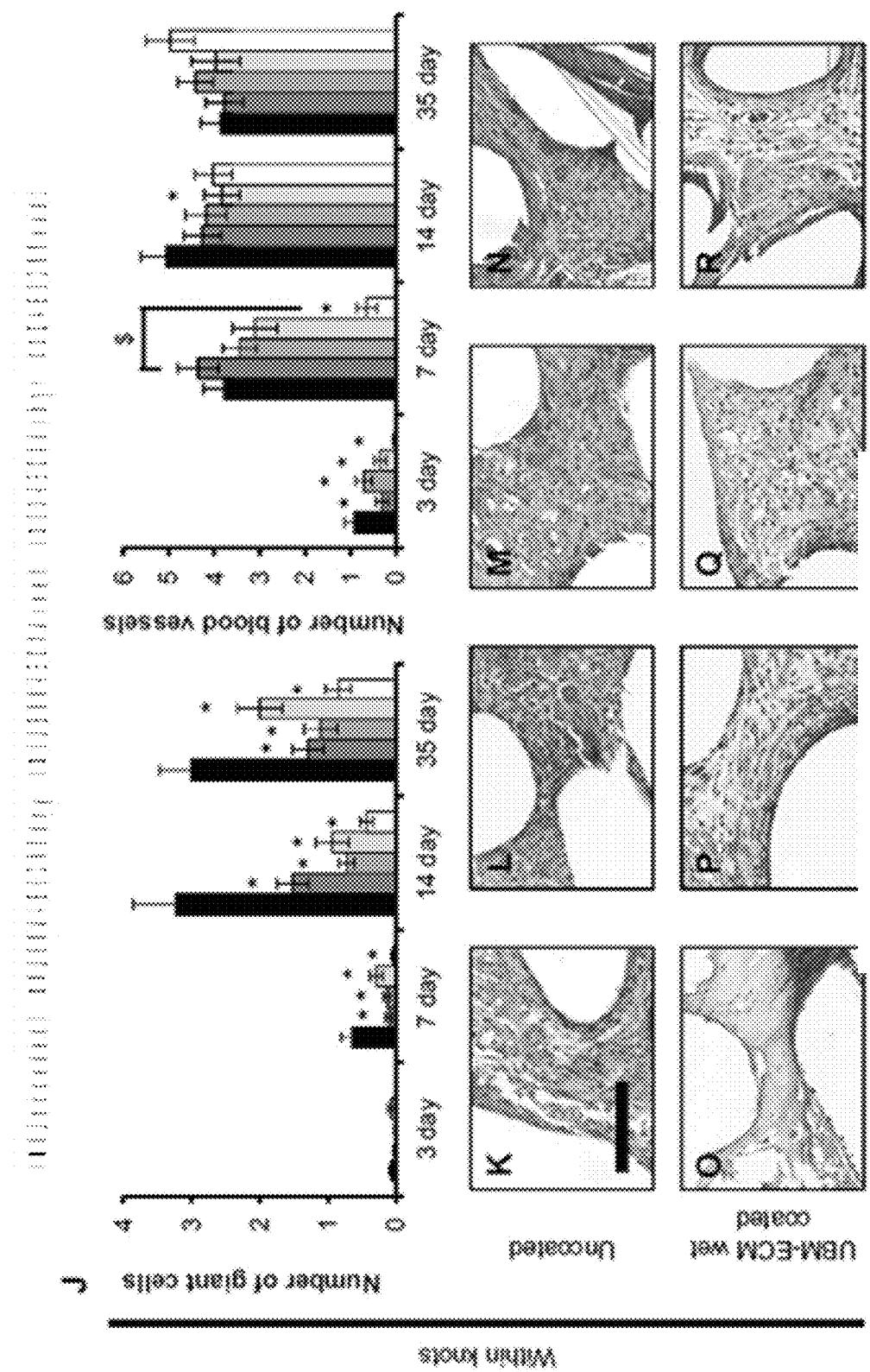

Histologic Analysis of Host Remodeling in Response to ECM Coated Mesh Implantation Histologic remodeling outcomes for uncoated and ECM coated mesh were determined from Masson's Trichrome stained images, and the number of foreign body giant cells and blood vessels were counted adjacent to single mesh fibers (FIG. 18A, panel A) and within mesh fiber knots (FIG. 18B, panel J). Foreign body giant cells adjacent to single fibers in uncoated mesh began to form by the 7 day time point, peaked by 14 days, and had declined by 35 days. Each ECM coating showed a similar reduction in the number of giant cells at the 14 day time point, though there were no differences from uncoated mesh by 35 days. The number of blood vessels adjacent to single mesh fibers increased between 3 and 14 day time points for all devices. There were fewer vessels around D-ECM coated mesh at the 7 day time point compared to uncoated and UBM coated mesh, but no differences at later time points.

Foreign body giant cell formation between mesh fiber knots was apparent by 7 days and was the greatest at the 14 and 35 day time points for all devices. A greater number of foreign body giant cells were observed between uncoated mesh fiber knots compared to ECM coated mesh at 7, 14, and 35 day time points. The number of blood vessels within knots of both uncoated and ECM coated mesh increased between 3 and 14 days. All ECM coatings reduced blood vessel formation within knots at the 3 day time point, but only the D-ECM wet and D-ECM dry coated mesh reduced vessel formation at the 7 and 14 day time points, respectively.

Conclusion

The present results show a robust accumulation of pro-inflammatory M1 macrophages at the mesh-tissue interface as early as 7 days following implantation, which persisted until the 35 day time point. Spatially, M1 accumulation was greatest directly adjacent to the mesh fibers, and rapidly diminished with distance to background levels by approximately 100 mm from the implant surface, suggesting a localized pro-inflammatory response to polypropylene. Though the M1 response was confined within close proximity to the mesh, pro-inflammatory cytokine release may still affect remodeling outcomes distal to the mesh. Conversely, there were relatively few anti-inflammatory M2 macrophages, reinforcing the assertion that a non-degradable polypropylene mesh induces a pro-inflammatory environment.

The present results show that hydrogel coatings composed of dermal or urinary bladder ECM are able to modulate the default innate immune response to heavyweight polypropylene mesh in vivo. ECM primarily attenuated the M1 response and foreign body giant cell formation around mesh devices in a specific spatial and temporal pattern, which was not dependent upon the tissue source or structure of the ECM coating. Improved remodeling response previously reported for an ECM coated polypropylene mesh compared to an uncoated mesh may be the result of macrophage polarization and consequent signaling during host remodeling. ECM hydrogel coatings are therefore a viable modification method to alleviate the chronic inflammatory response to non-degradable implanted medical devices.

Example 18—an ECM Hydrogel Coating Mitigates the Chronic Inflammatory Response to a Polypropylene Mesh Methods Test devices included uncoated and ECM coated heavyweight BARD™ polypropylene mesh (C.R. BARD), uncoated and ECM coated light-weight BARD™ Soft polypropylene mesh (C.R. BARD), and uncoated light-weight ULTRAPRO™ mesh (Ethicon.). These devices were implanted in a previously described rat partial thickness bilateral abdominal defect overlay model. The two time points investigated were 14 and 180 days. Histomorphologic scoring of the tissue remodeling response as well as macrophage phenotype characterization were performed at 14 days. Histomorphologic assessment, collagen deposition characterization, and biaxial testing were performed at 180 days post implantation. A total of 80 mesh devices were implanted, and 40 animals were used over the course of the study (i.e., bilateral implants per animal); 20 mesh devices were implanted for the 14 day time point (n-value=4 for each device), 60 mesh devices were implanted for the 180 day time point (n-value=12 for each device, 8 for biaxial testing and 4 for histology).

Dermal ECM was prepared as previously described above. Briefly, full thickness skin was harvested from market weight (~110 kg) pigs (Tissue Source, Inc., Lafayette, Ind.) and the subcutaneous fat and epidermis were removed by mechanical delamination followed by treatment with 0.25% trypsin (Thermo Fisher Scientific, Waltham, Mass.) for 6 h, 70% ethanol for 10 h, 3% $H_2O_2$ for 15 min, 1% Triton X-100 (Sigma-Aldrich, St. Louis, Mo.) in 0.26% EDTA/0.69% Tris for 6 h with a solution change for an additional 16 h, 0.1% peracetic acid/4% ethanol (Rochester Midland, Rochester, N.Y.) for 2 h. Water washes were performed between each chemical change with alternating water and phosphate buffered saline (PBS) washes following the final step. All chemical exposures were conducted under agitation on an orbital shaker at 300 rpm. Dermal ECM was then frozen, lyophilized, and comminuted into a 40 mesh powder. The dermal ECM powder was solubilized as previously described above by partial enzymatic digestion in a 1 mg/mL pepsin (Sigma-Aldrich) solution in 0.01 N HCl for 48 h at a concentration of 10 mg ECM/mL solution (dry wt/vol). Solubilized dermal ECM was brought to physiologic pH and salt concentration while on ice by adding ⅑ the digest volume of 10×PBS, ⅒ the volume of 0.1 N NaOH, and then further diluted to 8 mg ECM/mL with 1×PBS.

The neutralized dermal ECM digest was immediately added to a square plastic dish and 2 cm×3 cm pieces of pre-cut polypropylene mesh were suspended in the solution. The neutralized digest and polypropylene mesh were then placed in a non-humidified incubator at 37° C. for approximately 30-45 min until the dermal ECM digest formed a hydrogel (~4.5 mm total thickness) around the mesh and between the fibers of the polypropylene mesh. The dermal ECM hydrogel embedded mesh was then air dried at 37° C. overnight to complete the coating process. The end coating is a very thin (<1 mm) solid film around the synthetic mesh. This solid film will flake or chip if the mesh is bent at extreme angles while in a completely dry form. However, the ECM coating becomes pliable within minutes of hydration with saline or distilled water, and did not flake or chip during regular handling. All devices used for in vivo implantation were terminally sterilized with ethylene oxide.

Figure 19:
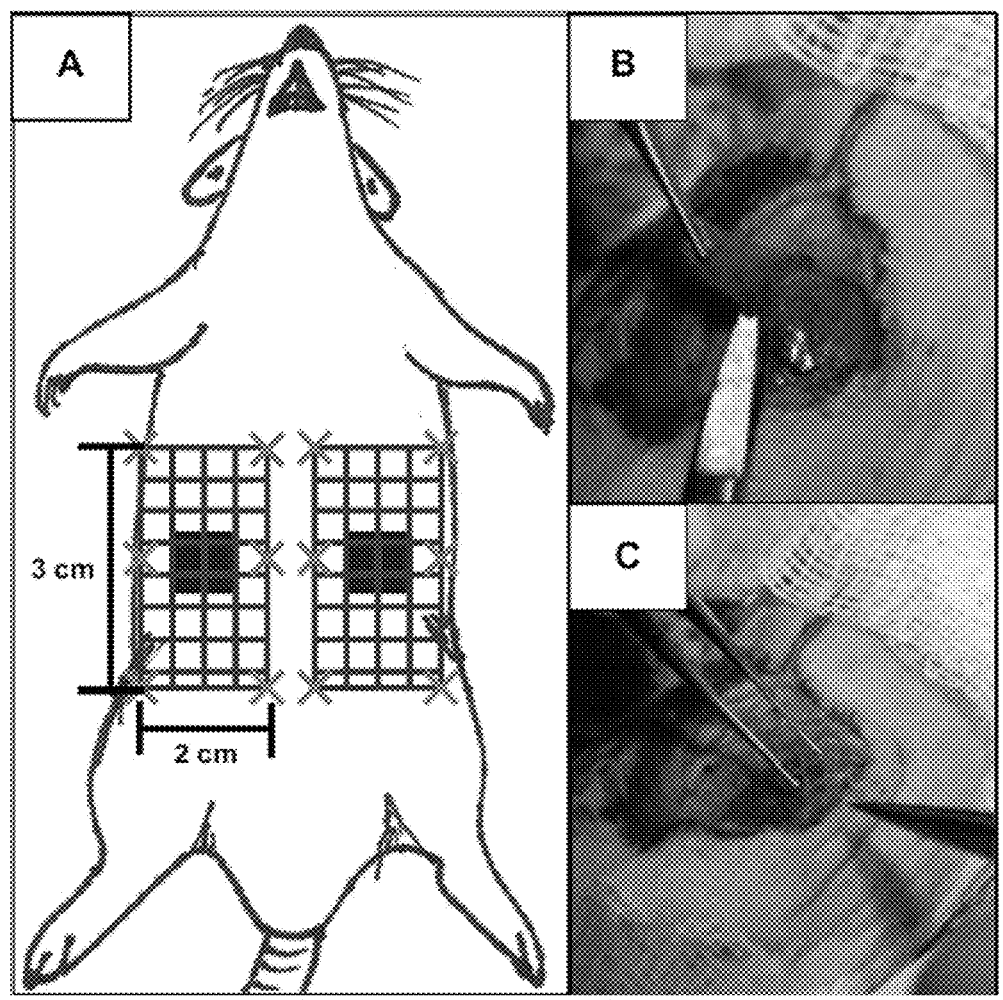
FIG. 19 shows a surgical model of mesh implantation in a rat. (A) Schematic representation of mesh placement. Two 1 cm×1 cm partial thickness abdominal wall paramedian defects were created (squares), and were repaired with 2 cm×3 cm mesh devices (patterned rectangle) using an overlay technique. Each mesh was parallel to the midline and bordered the edge of the rectus abdominus. Mesh devices were fixed to the abdominal using six single interrupted sutures (dark "X"s) along the edge of the mesh. (B) The 1 cm×1 cm partial thickness defect was created by removing the internal and external oblique, leaving the transversalis fascia and the peritoneum intact. (C) After making the defect, the 2 cm×3 cm surgical mesh test article was then fixated directly over top of the defect.

All procedures were approved by and performed according to the guidelines of the Institutional Animal Care and Use Committee at the University of Pittsburgh. Anesthesia was induced with 2.5-4% isoflurane, and surgical plane anesthesia was maintained with 0.5-4% isoflurane throughout the procedure. The ventral abdomen was prepared for aseptic survival surgery by clipping the fur over the entire abdominal region, and cleaning the operative area with three alternating scrubs of providone-iodine surgical scrub and 70% isopropyl alcohol solutions. A final preparation of 70% isopropyl alcohol was applied and allowed to dry, followed by placing sterile surgical drape(s) over the entire field. Following preparation of the ventral abdomen, a midline skin incision was made, and the skin on the right side of the abdomen was bluntly dissected from the underlying muscular tissue. A 1 cm2 partial thickness defect was created by removing the internal and external oblique, leaving the transversalis fascia and the peritoneum intact. A 2 cm×3 cm surgical mesh test article was then fixated directly over top of the defect (i.e., overlay technique) using six (6) interrupted 4-0 PROLENE™ sutures (FIG. 19). Following placement of the test article, the skin was closed with a continuous 4-0 VICRYL™ suture. A 1 cm$^2$ partial thickness defect with mesh overlay was then performed on the left side in a similar manner as the right. The animal was recovered from anesthesia, returned to its cage and allowed free access to food and water ad libitum. Rats were given Buprenex® (0.06 mg/kg subcutaneously) and Baytril® (5 mg orally) at the time of surgery and for 3 days post-surgery. Four (4) mesh devices from each group were explanted per time point to evaluate the histolomorphologic response, with an additional eight (8) mesh devices from each group explanted for 180 day biaxial mechanics testing.

At 14 days or 180 days post implantation, animals were sacrificed and test articles were excised with adjacent normal tissue. Euthanasia was achieved by $CO_2$ inhalation and subsequent cervical dislocation, which was performed in accordance with the guidelines of the American Veterinary Medical Association (AVMA) Panel of Euthanasia, and Journal of the American Veterinary Medical Association, 218(5):668-696, 2001. Following euthanasia, the skin was gently dissected, reflected, and photographs were taken of each animal and each test or control article in situ (FIG. 20A-20B). The sample was then divided in half and each half immersed in 10% Neutral Buffered Formalin (NBF) for further histological analysis.

Mesh devices were explanted 14 days post implantation, along with surrounding abdominal wall tissue. Mesh/tissue explants were fixed with 10% neutral buffered formalin for at least 24 h, embedded in paraffin, and sectioned (5 mm). Immunoflourescent labeling was performed to characterize macrophage phenotype in response to ECM coated and uncoated polypropylene mesh test articles. Slides were deparaffinized followed by antigen retrieval in heated citrate buffer for 20 min (10 mM citrate, pH 6.0 at 95-100° C.). Non-specific antibody binding was prevented by incubation for 1 h at room temperature with a blocking solution consisting of 2% normal horse serum (Hyclone), 1% bovine serum albumin (Sigma), 0.1% Triton X-100 (Sigma), and 0.1% Tween-20 (Sigma) in PBS. Sections were decanted and incubated with primary antibodies diluted 1:150 in blocking solution overnight at 4° C. Primary antibodies against the pan-macrophage marker CD68 (mouse anti-rat CD68, clone ED1, Abd Secotec), the M1 macrophage marker CD86 (rabbit anti-human CD86, clone EP 1158Y, Abcam), and the M2 macrophage marker CD 206 (goat anti-human CD206 goat anti-human CD206, polyclonal, Santa Cruz) were used. Sections were washed and incubated with the following fluorescently conjugated secondary antibodies diluted in blocking solution for 1 h at room temperature: donkey anti-mouse Alexa Fluor-594 (1:200 dilution, Invitrogen), donkey anti-rabbit PerCP-Cy5.5 (1:300 dilution, Santa Cruz), and donkey anti-goat Alexa Fluor-488 (1:200 dilution, Invitrogen). Nuclei were labeled with DAPI and slides coverslipped with fluorescent mounting medium (Dako). Multispectral epifluorescent images were acquired (Nuance) and spectrally unmixed to remove background autofluorescence. A total of 3 high magnification images (400×) were acquired at the mesh fiber pore interface adjacent to single fibers. The total number of cells co-expressing CD68 and either CD86 or CD206 was automatically quantified for each image using CellProfiler software. Macrophages were defined as CD68 positive co-localized with nuclei. M1 and M2 cells were defined as macrophages co-expressing CD86 or CD206, respectively. A subpopulation of cells co-expressed both M1 and M2 markers and were subsequently denoted as "co-labeled". Macrophage spatial distribution relative to mesh fibers was characterized by defining concentric rings around mesh fibers that were evenly spaced at 33 mm intervals. A total of 4 ring areas were defined around single fibers. Cells on the border of 2 rings were counted towards the inner ring.

A previously described quantitative histomorphometric scoring system (Wolf et al. Polypropylene surgical mesh coated with extracellular matrix mitigates the host foreign body response. J Biomed Mater Res A 2013; 102(1):234-46) was used to evaluate the host response to the implanted mesh materials 14 and 180 days post implantation as summarized in Table 2.

TABLE 2

Summary of quantitative histomorphometric analysis categories.

| Location of analysis | Analysis | Description of quantitative analysis |
| --- | --- | --- |
| Around mesh fibers | Cellularity | Number of cell layers of dense cellular accumulation immediately adjacent to fibers per field of view |
|  | Foreign body giant cells | Number of foreign body giant cell per field of view |
| Between mesh fibers | Cellularity | Number of mononuclear cells per field of view in increments of 50 cells |
|  | Vascularity | Number of blood vessels per field of view |

Fixed mesh-tissue explants were embedded in paraffin, sectioned (5 mm), mounted onto microscope slides, and stained with hematoxylin and eosin (H&E). A total of 6 high magnification images (400×) were acquired for each H&E stained section; three images of the mesh fiber/tissue interface and three images of the deposited tissue between mesh fibers. The mesh fiber/tissue interface images were positioned at the edge of mesh fiber bundles such that the inflammatory response to the mesh was visible within the field of view. The mesh fiber/tissue interface images were quantified for two criteria: the thickness of the dense cell accumulation at the fiber surface (reported as number of cell layers away from the mesh fiber) and the total number of multinucleate foreign body giant cells surrounding the mesh fiber in each image. The images of the tissue between mesh fibers were acquired at the midpoint between adjacent mesh fiber bundles and were quantified for two criteria; the total number of mononuclear cells per image (rounded to the nearest 50) and the total number of blood vessels (with identifiable lumen and red blood cells). All quantitative analysis was conducted by five (5) independent blinded observers.

The area of collagen fibers as a function of their color hue was quantified from tissue sections stained with picrosirius red and imaged with circularly polarized light microscopy (200× magnifications), as previously described (Wolf et al. Polypropylene surgical mesh coated with extracellular matrix mitigates the host foreign body response. J Biomed Mater Res A 2013; 102(1):234-46). The color hue corresponds to relative fiber thickness from thin fibers to increasingly thick fibers. Following a previously published protocol [29,30] custom algorithm was constructed with Matlab software (The Mathworks, Natick, Mass.) that: (1) cropped each image to only connective tissue directly between mesh fibers removing all subcutaneous connective and underlying muscle tissue; (2) transformed each image from the RGB to the HSV color model; (3) separated each color component as a function of hue; (4) applied a threshold to remove noise from an average of a global threshold using Otsu's method (intensity value of 50/256); and (5) expressed the collagen content for each color component as a percentage of the area of each image.

Planar biaxial mechanical testing was performed as previously described (Wolf et al. Polypropylene surgical mesh coated with extracellular matrix mitigates the host foreign body response. J Biomed Mater Res A 2013; 102(1):234-46). Briefly, a 15 mm×15 mm sample was acquired from each explant centered on the muscle defect. Thickness was measured from the center of each explant using a Sterret® caliper model 1010. Four (4) fiducial markers were placed in the center of the square on the anterior surface after the removal of excess loose connective tissue and fat. Deformations were measured optically by tracking this four marker array. Two loops of suture of equal length were attached to each side of the specimens with four stainless steel hooks, and 500 g Model 31 load cells (Honeywell) were used to acquire load values. Biaxial testing was conducted with the circumferential and longitudinal specimen axes aligned with the device axis and submerged in a bath at room temperature. The biaxial testing system was automated, allowing the marker locations and axial forces to be continuously recorded with custom marker tracking and data acquisition software (Billiar K L et al. Biaxial mechanical properties of the natural and glutaraldehyde treated aortic valve cusp-Part I: experimental results. J Biomech Eng 2000; 122(1):23-30).

Specimens were first preconditioned by cyclically loading the specimens to the desired maximum equibiaxial stress of 85 kPA for ten cycles using a cycle time of 30 s per cycle to quantify the quasi-static response. Immediately following the preconditioning cycles, the specimen was completely unloaded and imaged in its post-preconditioned free-floating configuration. The stress-stretch plot reported in this study start from a 0.5 g preload that is referenced to the post-precondition free float state, which was used to ensure test response repeatability. The response of the eight explants was averaged after a three point linear interpolation at representative stress values and reported with standard error. Native abdominal walls were also tested for comparison. The maximum strain for each sample was then defined as the strain at the maximum tested stress of 85 kPa.

The histomorphometric data, total number of macrophages, collagen deposition, and maximum strain values are presented as the mean±the standard error of the mean. Statistical analysis was performed using a one-way ANOVA evaluating each variable (M1, M2, blood vessels, etc.) within each time point using SPSS software. A post-hoc Tukey test was conducted with a p-value <0.05 considered statistically significant. Data normality was determined using the Kolmgorov-Smirnov test, and natural logarithm transformation applied when normality was violated.

Results

After 14 days, fewer cells were present directly adjacent to and between mesh fibers in the ECM coated devices compared to the uncoated mesh devices (FIGS. 21 and 22). In addition, the ECM coating resulted in a decreased number of pro-inflammatory M1 macrophages directly around the mesh fibers in comparison to the uncoated mesh devices (FIG. 23A-23B). Histomorphologic analysis at 180 days showed the ECM coating reduced the total cellularity as well as the number of foreign body giant cells around mesh fibers for the heavy-weight BARD™ mesh (FIG. 22A-22B). The ECM coating decreased the density and size of collagen deposited between mesh fibers when compared to the uncoated mesh devices (FIG. 24) at 180 days. Lastly, biaxial testing showed the ECM coating did not affect longitudinal or circumferential strain (FIG. 25A-25B).

Cellular accumulation and number of foreign body giant cells around mesh fibers were quantified for each mesh device 14 and 180 days post implantation (FIGS. 22A and 22B, top panels). The ECM coating decreased the cellular accumulation around mesh fibers at both 14 and 180 days post implantation for the BARD™ and BARD™ Soft meshes. Furthermore, the ECM coating decreased the number of foreign body giant cells around the mesh fibers at 180 days post implantation for the BARD™ heavy-weight mesh. The ULTRAPRO™ Mesh had a greater cellular accumulation around mesh fibers than the ECM coated BARD™ and BARD™ Soft meshes at both 14 and 180 days. The ULTRAPRO™ mesh also had more foreign body giant cells around mesh fibers than the ECM coated BARD™ and ECM coated BARD™ Soft meshes at 14 days post implantation.

Cellularity and vascularity between mesh fibers were quantified for all mesh groups 14 and 180 days post implantation (FIGS. 22A and 22B, bottom panels). The ECM coating decreased cellularity between mesh fibers when compared to the uncoated BARD™ and BARD™ Soft mesh devices at 14 days post implantation. No difference in cellularity between groups was observed at the 180 day time point. The uncoated BARD™ heavy-weight mesh had a greater amount of vascularity between mesh fibers than the other mesh devices 14 days post implantation. At 180 days the uncoated BARD™ heavy-weight and ECM coated BARD™ heavy-weight had more vascularity between fibers than the three light-weight mesh devices.

The effect of an ECM coating on macrophage polarization was investigated using immunolabeling of CD68+pan macrophages (M0), CD86+pro inflammatory macrophages (M1), and CD206+constructive remodeling macrophages (M2) (FIG. 23A-23B). The ECM coating markedly reduced the number of M1 pro-inflammatory cells directly adjacent to PP mesh fibers (within 100 microns of the mesh fiber) when compared to the uncoated polypropylene meshes. These results are in agreement with those of Example 16 above.

The total amount of collagen deposition was quantified for each mesh group at 180 days post implantation (FIG. 24). The ECM coating resulting in less overall collagen deposition (addition of all colors) when compared to the uncoated BARD™ and BARD™ Soft meshes. Both ECM coated meshes had more deposition of thin collagen fibers compared to the uncoated BARD™ heavy-weight mesh. The ECM coated meshes also had less deposition of thick collagen fibers compared to the uncoated BARD™ and BARD™ Soft Meshes.

Stress-strain curves were generated for all explants at 180 days, including native controls (FIG. 25A). The maximum strain defined at a stress of 85 kPa for both circumferential and longitudinal axis was performed for all mesh explant groups and compared to native tissue (FIG. 25B). No difference was observed between any of the mesh explant groups for both the longitudinal and circumferential maximum strains (FIG. 25B). All mesh explant groups were less compliant than native abdominal wall tissue in both circumferential and longitudinal axis.

Conclusions

The present study showed a clear and distinct long term effect upon the host response to a PP mesh when an ECM hydrogel coating was applied. The most notable changes were the decrease in M1 pro-inflammatory macrophages around mesh fibers shortly after implantation, the decreased density of collagen, and the thinner collagen fiber type deposited between mesh fibers 180 days post implantation. The ECM hydrogel coating also decreased cellular accumulation around polypropylene mesh fibers and decreased the number of foreign body giant cells around the BARD™ heavy-weight mesh. Planar biaxial mechanical testing showed the ECM coating did not affect mesh/tissue strength at six months. These results are consistent with those from Example 16 above, which showed an ECM coating for a PP mesh can modulate the acute (35 day) response. The present results extend the findings of the downstream remodeling outcome to 180 days following implantation of an ECM coated PP mesh in an abdominal wall defect model.

The promising findings of the present study allow speculation regarding the extension of an ECM coating to other biomaterial and therapeutic applications. For example, applying an ECM coating to synthetic materials used as cardiovascular stents could mitigate the subsequent intimal hyperplasia and chronic inflammatory response.

Although the present invention has been described with references to specific details of certain embodiments thereof, it is not intended that such details should be regarded as limitations upon the scope of the invention except in so far as they are included in the claims.

We claim:

1. A surgical mesh comprising a non-degradable synthetic polymer mesh embedded within a reverse-gelling hydrogel comprising intact ECM prepared from decellularized tissue, wherein the non-degradable synthetic polymer mesh comprises a non-degradable polymer selected from the group consisting of polytetrafluoroethylene, polyethylene terephthalate, polypropylene, and mixtures thereof.

2. The surgical mesh of claim 1, wherein the non-degradable synthetic polymer mesh is polypropylene.

3. The surgical mesh of claim 1, wherein the hydrogel forms a gel when the temperature of the gel is raised above 10° C.

4. The surgical mesh of claim 1, wherein the ECM is derived from warm-blooded mammalian tissue.

5. The surgical mesh of claim 4, wherein the warm-blooded mammalian tissue is derived from a pig, cow, monkey, or human.

6. The surgical mesh of claim 4, wherein the warm-blooded mammalian tissue is derived from one or more of urinary bladder, spleen, liver, heart, pancreas, ovary, small intestine, or dermis.

7. The surgical mesh of claim 4, wherein the ECM is derived from dermis.

8. The surgical mesh of claim 1, wherein the ECM is not dialyzed.

9. The surgical mesh of claim 1, wherein the ECM contains less than 50 ng/mg DNA.

10. The surgical mesh of claim 1, wherein the ECM contains less than 750 nmol phospholipids/g ECM.

11. The surgical mesh of claim 1, wherein the mesh is a cylindrical mesh having a lumen therethrough.

12. A method of repairing a defect in a body, comprising the step of integrating the surgical mesh of claim 1 at a site of a defect in a patient in need thereof.

13. The method of claim 12, wherein the defect is a hernia.

14. The method of claim 12, wherein the defect is a pelvic floor defect.

15. The method of claim 12, wherein the defect is in breast tissue.

16. The method of claim 12, wherein the defect is a wound.

* * * * *